(12) United States Patent
Reed et al.

(10) Patent No.: US 10,258,805 B2
(45) Date of Patent: *Apr. 16, 2019

(54) SURGICAL METHOD FOR IMPLANTABLE HEAD MOUNTED NEUROSTIMULATION SYSTEM FOR HEAD PAIN

(71) Applicant: SYNTILLA MEDICAL LLC, Southlake, TX (US)

(72) Inventors: Kenneth Lyle Reed, Dallas, TX (US); Robert Raymond Bulger, Dallas, TX (US); Michael Steven Colvin, Newbury Park, CA (US)

(73) Assignee: SYNTILLA MEDICAL, LLC, Southlake, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/599,206

(22) Filed: May 18, 2017

(65) Prior Publication Data

US 2017/0252568 A1    Sep. 7, 2017

Related U.S. Application Data

(63) Continuation-in-part of application No. 14/879,943, filed on Oct. 9, 2015, now Pat. No. 9,884,190, which
(Continued)

(51) Int. Cl.
*A61N 1/378* (2006.01)
*A61N 1/375* (2006.01)
(Continued)

(52) U.S. Cl.
CPC ......... *A61N 1/3787* (2013.01); *A61N 1/0526* (2013.01); *A61N 1/0551* (2013.01);
(Continued)

(58) Field of Classification Search
CPC .... A61N 1/3787; A61N 1/375; A61N 1/0526; A61N 1/0551; A61N 1/37211;
(Continued)

(56) References Cited

U.S. PATENT DOCUMENTS

| | | |
|---|---|---|
| 3,727,616 A | 4/1973 | Lenzkes |
| 4,612,934 A | 9/1986 | Borkan |

(Continued)

FOREIGN PATENT DOCUMENTS

| | | |
|---|---|---|
| CA | 2734775 | 2/2015 |
| EP | 0007157 | 1/1980 |
| WO | 2009158389 | 12/2009 |

OTHER PUBLICATIONS

PCT: International Search Report and Written Opinion of PCT/US2014/51235; dated Feb. 19, 2015; 24 pages. Feb. 19, 2015.
(Continued)

*Primary Examiner* — Catherine M Voorhees
(74) *Attorney, Agent, or Firm* — Gregory M. Howison

(57) ABSTRACT

A method for subcutaneously treating pain in a patient includes first providing a neurostimulator with an IPG body and at least a primary, a secondary, and a tertiary integral lead with electrodes disposed thereon. A primary incision is opened to expose the subcutaneous region below the dermis in a selected portion of the body. A pocket is then opened for the IPG through the primary incision and the integral leads are inserted through the primary incision and routed subcutaneously to desired nerve regions along desired paths. The IPG is disposed in the pocket through the primary incision. The primary incision is then closed and the IPG and the electrodes activated to provide localized stimulation to the desired nerve regions and at least three of the nerves associated therewith to achieve a desired pain reduction response from the patient.

20 Claims, 62 Drawing Sheets

Related U.S. Application Data is a continuation-in-part of application No. 14/717,912, filed on May 20, 2015, now Pat. No. 9,974,968, which is a continuation of application No. 14/460,139, filed on Aug. 14, 2014, now Pat. No. 9,042,991.

(60) Provisional application No. 61/894,795, filed on Oct. 23, 2013.

(51) Int. Cl.
  *A61N 1/372* (2006.01)
  *A61N 1/36* (2006.01)
  *A61N 1/05* (2006.01)

(52) U.S. Cl.
  CPC .......... *A61N 1/36075* (2013.01); *A61N 1/375* (2013.01); *A61N 1/37211* (2013.01); *A61N 1/37229* (2013.01); *A61N 1/0504* (2013.01); *A61N 1/3758* (2013.01); *A61N 1/37247* (2013.01); *A61N 1/37514* (2017.08)

(58) Field of Classification Search
  CPC ............ A61N 1/36075; A61N 1/37229; A61N 1/37247; A61N 1/3758; A61N 1/37514; A61N 1/0504
  See application file for complete search history.

(56) References Cited

U.S. PATENT DOCUMENTS

| | | |
|---|---|---|
| 4,793,353 A | 12/1988 | Borkan |
| 4,819,647 A | 4/1989 | Byers |
| 5,000,194 A | 3/1991 | Van Den Honert et al. |
| 5,037,497 A | 8/1991 | Stypulkowski |
| 5,215,086 A | 6/1993 | Terry, Jr. et al. |
| 5,279,292 A | 1/1994 | Baumann et al. |
| 5,545,219 A | 8/1996 | Kuzma |
| 5,733,313 A | 3/1998 | Barreras, Sr. |
| 5,876,425 A | 3/1999 | Gord et al. |
| 6,016,449 A | 1/2000 | Fischell et al. |
| 6,088,619 A | 7/2000 | Hein et al. |
| 6,178,353 B1 | 1/2001 | Griffith et al. |
| 6,236,892 B1 | 5/2001 | Feler |
| 6,246,911 B1 | 6/2001 | Seligman |
| 6,516,227 B1 | 2/2003 | Meadows |
| 6,529,774 B1 | 3/2003 | Greene |
| 6,597,954 B1 | 7/2003 | Pless et al. |
| 6,606,521 B2 | 8/2003 | Paspa et al. |
| 6,618,623 B1 | 9/2003 | Pless et al. |
| 6,895,283 B2 | 5/2005 | Erickson et al. |
| 6,920,359 B2 | 7/2005 | Meadows et al. |
| 7,127,298 B1 | 10/2006 | He et al. |
| 7,319,906 B2 | 1/2008 | Kuzma et al. |
| 7,437,197 B2 | 10/2008 | Harris et al. |
| 7,499,755 B2 | 3/2009 | Cross, Jr. |
| 7,676,273 B2 | 3/2010 | Goetz et al. |
| 7,729,781 B2 | 6/2010 | Swoyer et al. |
| 7,769,461 B2 | 8/2010 | Whitehurst et al. |
| 7,894,905 B2 | 2/2011 | Pless et al. |
| 8,027,735 B1 | 9/2011 | Tziviskos et al. |
| 8,030,798 B2 | 10/2011 | Seligman |
| 8,140,152 B2 | 3/2012 | John et al. |
| 8,165,678 B2 | 4/2012 | Forsberg |
| 8,412,334 B2 | 4/2013 | Whitehurst et al. |
| 8,504,163 B1 | 8/2013 | Meadows |
| 8,509,876 B2 | 8/2013 | Karmarkar |
| 8,538,545 B2 | 9/2013 | Meskens |
| 8,543,212 B2 | 9/2013 | Merfeld et al. |
| 8,634,909 B2 | 1/2014 | Zimmerling et al. |
| 8,639,344 B2 | 1/2014 | Greenberg et al. |
| 8,639,391 B1 | 1/2014 | Alberth et al. |
| 8,649,880 B1 | 2/2014 | Parker |
| 8,718,779 B2 | 5/2014 | Whitehurst et al. |
| 8,774,924 B2 | 7/2014 | Weiner |
| 8,958,880 B2 | 2/2015 | De Giorgio |
| 8,972,015 B2 | 3/2015 | Stack et al. |
| 9,020,589 B2 | 4/2015 | Torgerson |
| 9,031,662 B2 | 5/2015 | Leigh et al. |
| 9,095,699 B2 | 8/2015 | Rosenberg et al. |
| 9,101,732 B2 | 8/2015 | Dadd et al. |
| 9,119,957 B2 | 9/2015 | Gantz et al. |
| 9,421,387 B2 | 8/2016 | Hazard et al. |
| 9,884,190 B2 * | 2/2018 | Reed .................. A61N 1/36075 |
| 2002/0116042 A1 | 8/2002 | Boling |
| 2005/0027192 A1 | 2/2005 | Govari et al. |
| 2005/0102006 A1 | 5/2005 | Whitehurst et al. |
| 2005/0182470 A1 | 8/2005 | Cross |
| 2005/0209667 A1 | 9/2005 | Erickson et al. |
| 2006/0241717 A1 | 10/2006 | Whitehurst et al. |
| 2006/0247754 A1 | 11/2006 | Greenberg et al. |
| 2006/0293723 A1 | 12/2006 | Whitehurst et al. |
| 2007/0049988 A1 * | 3/2007 | Carbunaru ........... A61N 1/0551 607/59 |
| 2007/0073357 A1 | 3/2007 | Rooney et al. |
| 2007/0112404 A1 | 5/2007 | Mann et al. |
| 2007/0203545 A1 | 8/2007 | Stone et al. |
| 2008/0039916 A1 | 2/2008 | Colliou et al. |
| 2008/0183253 A1 | 7/2008 | Bly |
| 2008/0269716 A1 | 10/2008 | Bonde |
| 2008/0300657 A1 | 12/2008 | Stultz |
| 2009/0018619 A1 | 1/2009 | Skelton et al. |
| 2009/0210028 A1 | 8/2009 | Rigaux |
| 2009/0216324 A1 | 8/2009 | Leigh et al. |
| 2009/0312769 A1 | 12/2009 | Dadd |
| 2010/0110741 A1 | 5/2010 | Lin et al. |
| 2010/0114249 A1 | 5/2010 | Wahlstrand et al. |
| 2010/0161004 A1 | 6/2010 | Najafi |
| 2010/0274313 A1 | 10/2010 | Boling et al. |
| 2010/0331922 A1 | 12/2010 | Digiore et al. |
| 2011/0009925 A1 | 1/2011 | Leigh et al. |
| 2011/0093047 A1 | 4/2011 | Davis et al. |
| 2011/0112603 A1 | 5/2011 | Degiorgio et al. |
| 2011/0172736 A1 | 7/2011 | Gefen et al. |
| 2012/0078327 A1 | 3/2012 | Sloan et al. |
| 2012/0078337 A1 | 3/2012 | Darley et al. |
| 2012/0078338 A1 | 3/2012 | Darley et al. |
| 2012/0112556 A1 | 5/2012 | Forsell |
| 2012/0215218 A1 | 8/2012 | Lipani |
| 2012/0274270 A1 | 11/2012 | Dinsmoor |
| 2012/0277823 A1 | 11/2012 | Gerber et al. |
| 2013/0057364 A1 | 3/2013 | Kesler et al. |
| 2013/0085542 A1 | 4/2013 | Mashiach |
| 2013/0085561 A1 | 4/2013 | Mashiach |
| 2013/0165996 A1 | 6/2013 | Meadows et al. |
| 2013/0197613 A1 | 8/2013 | Kelly |
| 2013/0198531 A1 | 8/2013 | Hansen |
| 2013/0238067 A1 | 9/2013 | Baudino |
| 2013/0282086 A1 | 10/2013 | McDonald et al. |
| 2013/0333918 A1 | 12/2013 | Lotfi |
| 2014/0012349 A1 | 1/2014 | Zimmerling et al. |
| 2014/0142669 A1 | 5/2014 | Cook et al. |
| 2014/0148883 A1 | 5/2014 | Stack et al. |
| 2014/0222125 A1 | 8/2014 | Glenn et al. |
| 2014/0303685 A1 | 10/2014 | Rosenberg et al. |
| 2014/0343626 A1 | 11/2014 | Thenuwara et al. |
| 2015/0025613 A1 | 1/2015 | Nyberg, II et al. |
| 2015/0087892 A1 | 3/2015 | Tourrel et al. |
| 2015/0157862 A1 | 6/2015 | Greenberg et al. |
| 2015/0280444 A1 | 10/2015 | Smith |
| 2015/0303806 A1 | 10/2015 | Madsen et al. |
| 2016/0036244 A1 | 2/2016 | Griffith |
| 2016/0235993 A1 | 8/2016 | Cryer et al. |
| 2016/0242685 A1 | 8/2016 | De Hennis |
| 2017/0056646 A1 | 3/2017 | Sibary et al. |

OTHER PUBLICATIONS

PCT: International Search Report and Written Opinion of PCT/US14/51235 (related application); dated Feb. 19, 2015; 24 pages. Feb. 19, 2015.

Weiner RL and Reed KL. Peripheral neurostimulation for control of intractable occipital neuralgia. Neuromodulation: journal of the

(56) References Cited

OTHER PUBLICATIONS

International Neuromodulation Society. 1999; 2: 217-21 Jan. 1, 1999.
Goadsby PJ and Spencer T. Current practice and future directions in the prevention and acute management of migraine. The Lancet Neurology. 2010; 9: 285-98. Jan. 1, 2010.
Dodick DW. Occipital nerve stimulation for chronic cluster headache. Advanced Studies in Medicine. 2003; 3: S569-S71. Jan. 1, 2003.
Saper JR, Dodick DW, Silberstein SD, McCarville S, Sun M and Goadsby PJ. Occipital nerve stimulation for the treatment of intractable chronic migraine headache: ONSTIM feasibility study. Cephalalgia: an international journal of headache. 2011; 31:271-85. Jan. 1, 2011.
Silberstein S, Dodick DW, Reed KL, et al. Safety and efficacy of peripheral nerve stimulation of the occiptial nerves for the management of chronic migraine. Cephalalgia: an international journal of headache. 2012. Jan. 1, 2012.
Slavin KV, Colpan ME, Munawar N, Wess C and Nersesyan H. Trigeminal and occipital peripheral nerve stimulation for craniofacial pain: a single-institution experience and review of the literature. Neurosurgical focus. 2006; 21: E5. Jan. 1, 2006.
Schwedt TJ, Dodick DW, Hentz J, Trentman TL and Zimmerman RS. Occipital nerve stimulation for chronic headache—long-term safety and efficacy. Cephalalgia: an international journal of headache. 2007; 27: 153-7. Jan. 1, 2007.
Reed KL, Black Sb, Banta CJ, 2nd and Will KR. Combined occipital and supraorbital neurostimulation for the treatment of chronic migraine headaches: initial experience. Cephalalgia: an international journal of headache. 2010; 30: 260-71. Jan. 1, 2010.
Reed KL, Will KR, Chapman J and Richter E. Combined occipital and supraorbital neurostimulation for chronic migraine headaches [abst]. 15th Congress of the International Headache Society. Berlin, Germany: Cephalalgia, 2011, p. 98-9. Jan. 1, 2011.
Lipton RB, Goadsby PJ, Cady RK, et al. PRISM study: occipital nerve stimulation for treatment-refractory migraine (p abs). Cephalalgia: an international journal of headache. 2009; 29: 30. Jan. 1, 2009.
Reed KL. Peripheral neuromodulation and headaches: history, clinical approach, and considerations on underlying mechanisms. Current pain and headache reports. 2012; 17: 25-35. Jan. 1, 2012.
Mueller OM, Gaul C, Katsarava Z, Diener HC, Sure U and Gasser T. Occipital nerve stimulation for the treatment of chronic cluster headache—lessons learned from 18 months experience. Central European neurosurgery. 2011; 72: 84-9. Jan. 1, 2011.
Medtronic, Inc. Peripheral Nerve Stimulation: Percutaneous Lead Implantation Guide for Treatment of Chronic Pain Jan. 1, 1999.
Redl, Richard. Fundamental Considerations for Very High Frequency Power Conversion. Electronic Feasibility Investigations. 2008. Jan. 1, 2008.
Sreelakshmi V, Menon R, Sheela G. An RF-FC Converter with Wide Dynamic Range Input Matching for Power Recovery Applications. International Journal of Advanced Research in Electrical, Electronics and Instrumentation Engineering. Dec. 2014. Dec 1, 2014.
Rooij M. eGaN FET based Wireless Energy Transfer Topology Performance Comparisons. 2015. Jan. 1, 2015.
InTech; Ramakrishnan, S.; Modern Speech Recognition Approaches with Case Studies; Chapter 10; Nov. 28, 2012. Nov. 28, 2012.
European Patent Office, Extended European Search Report, No. EP 14 85 5587, dated May 24, 2017; Lins, Stephanie; 7 pages.

* cited by examiner

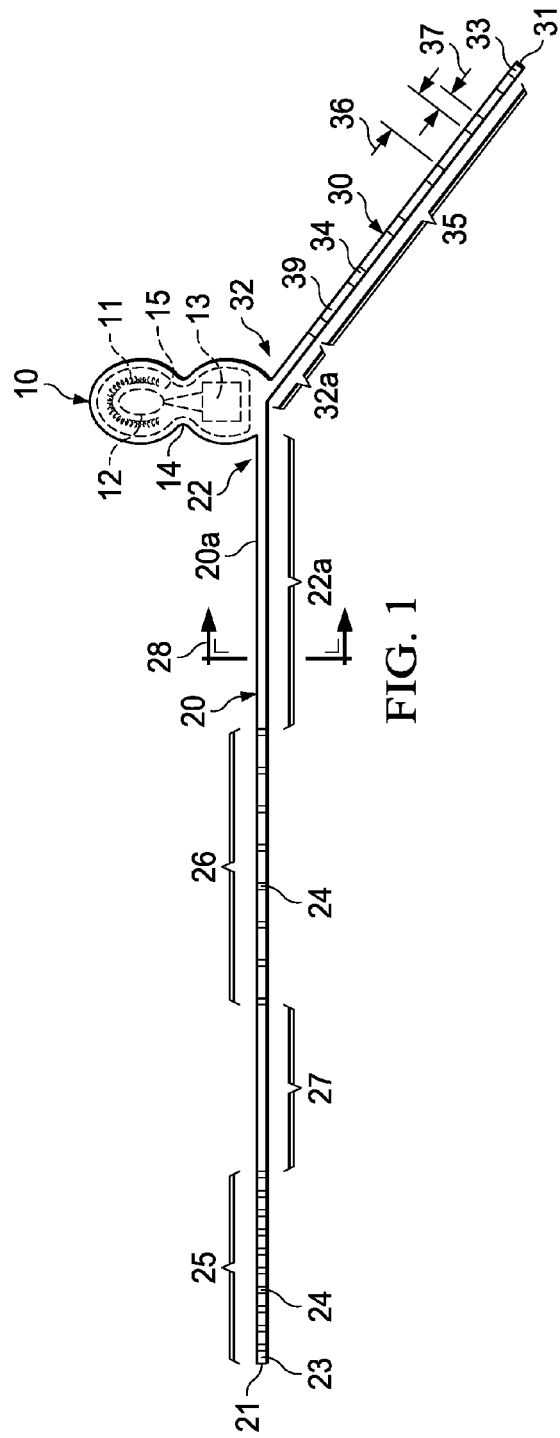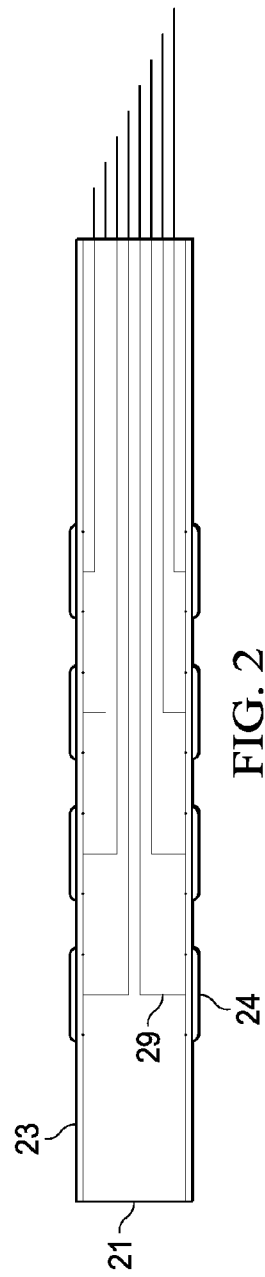

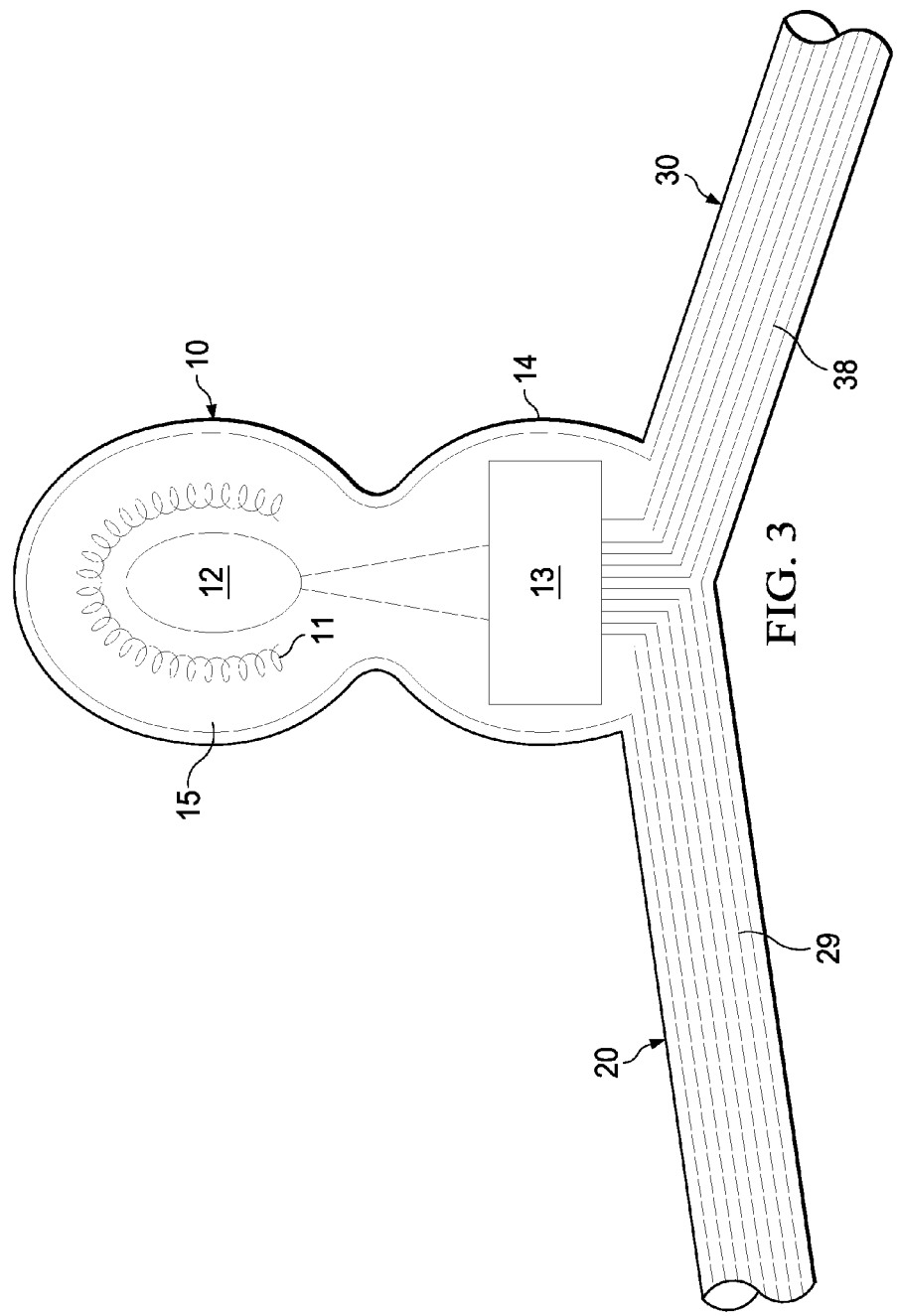

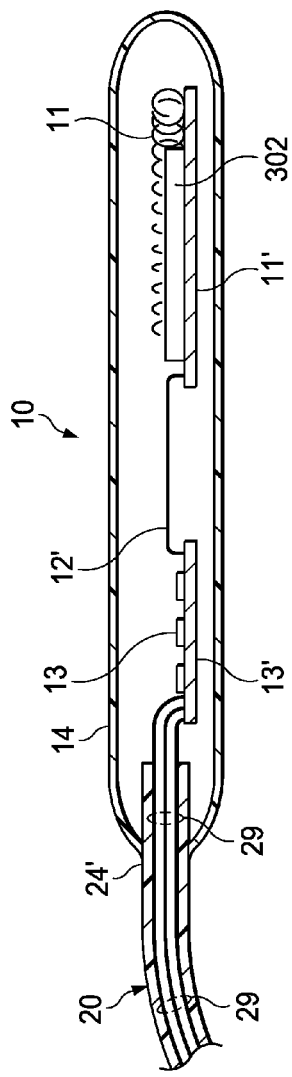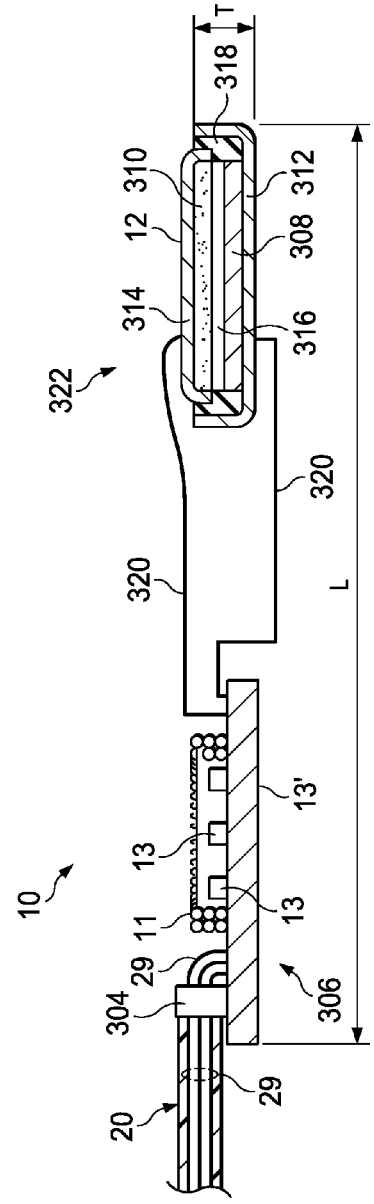

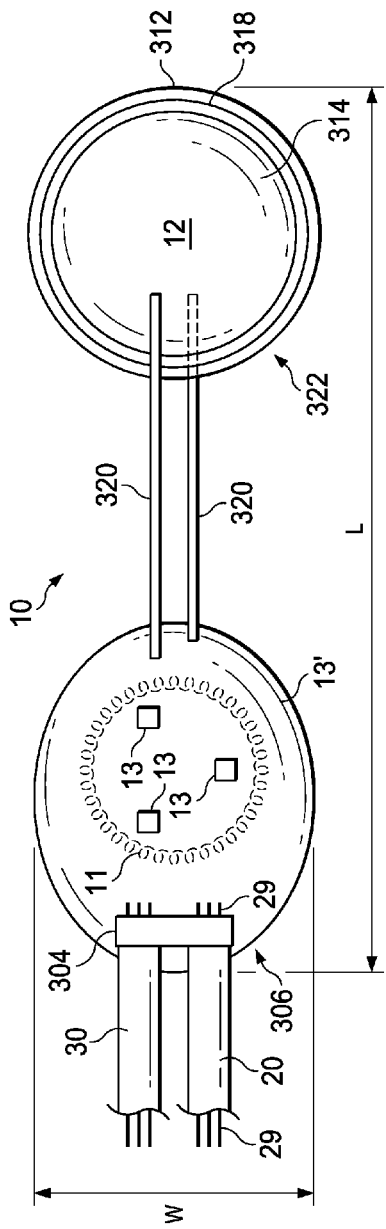
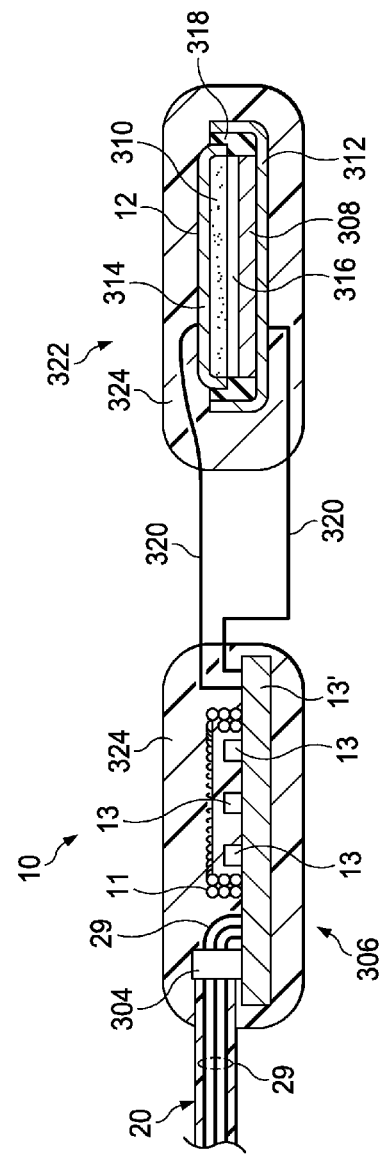
FIG. 3C
FIG. 3D

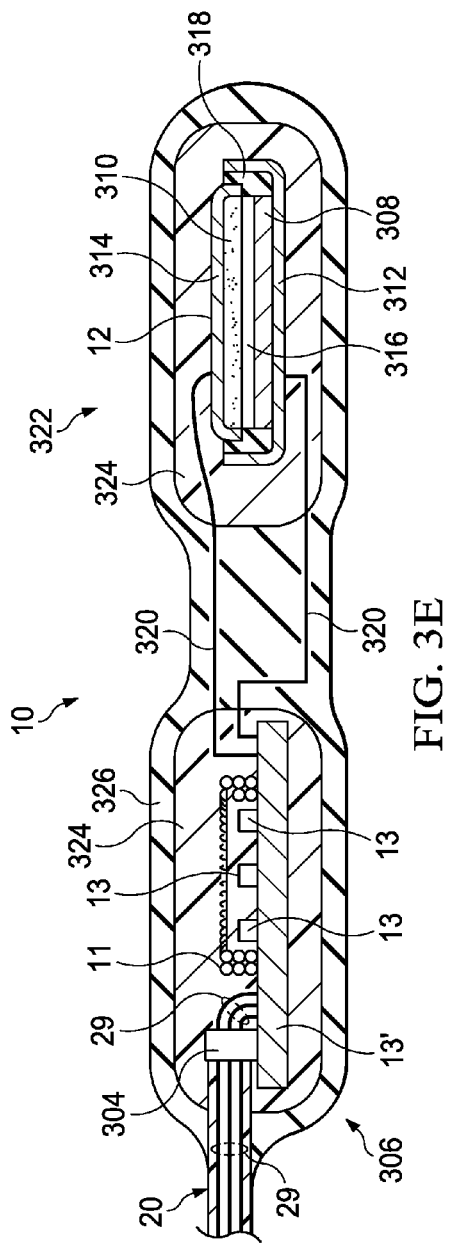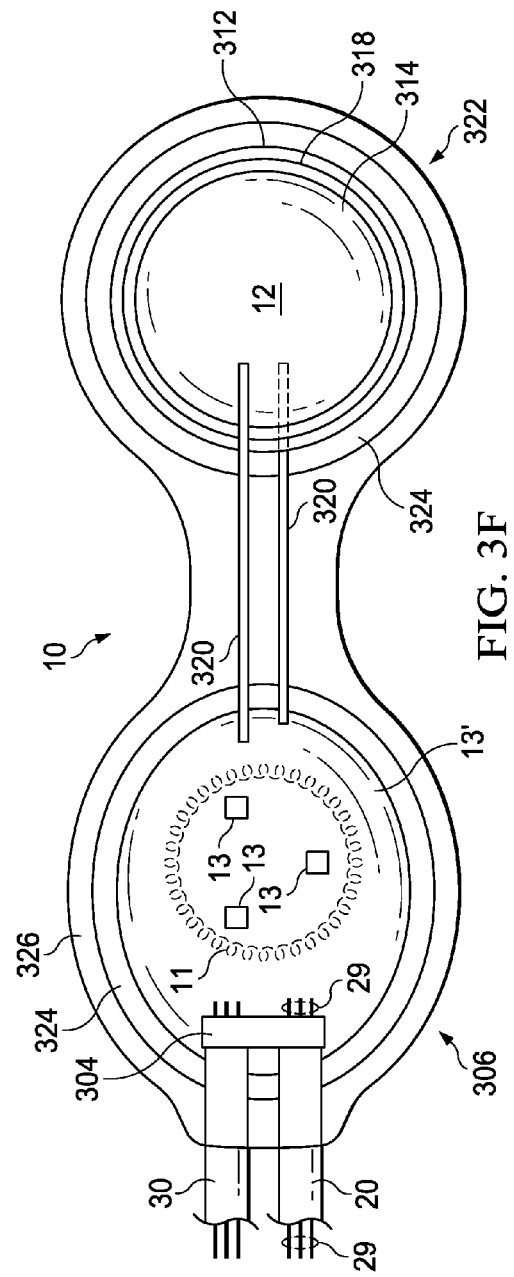

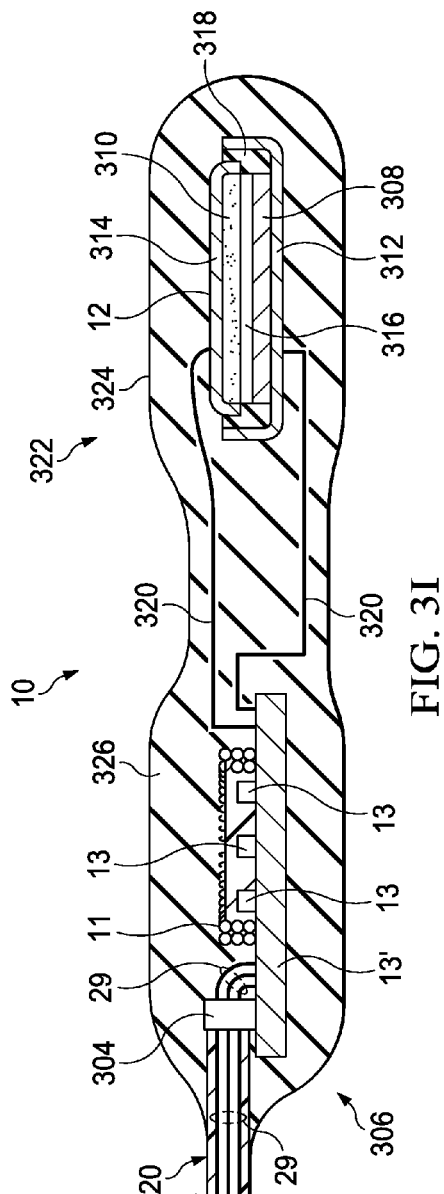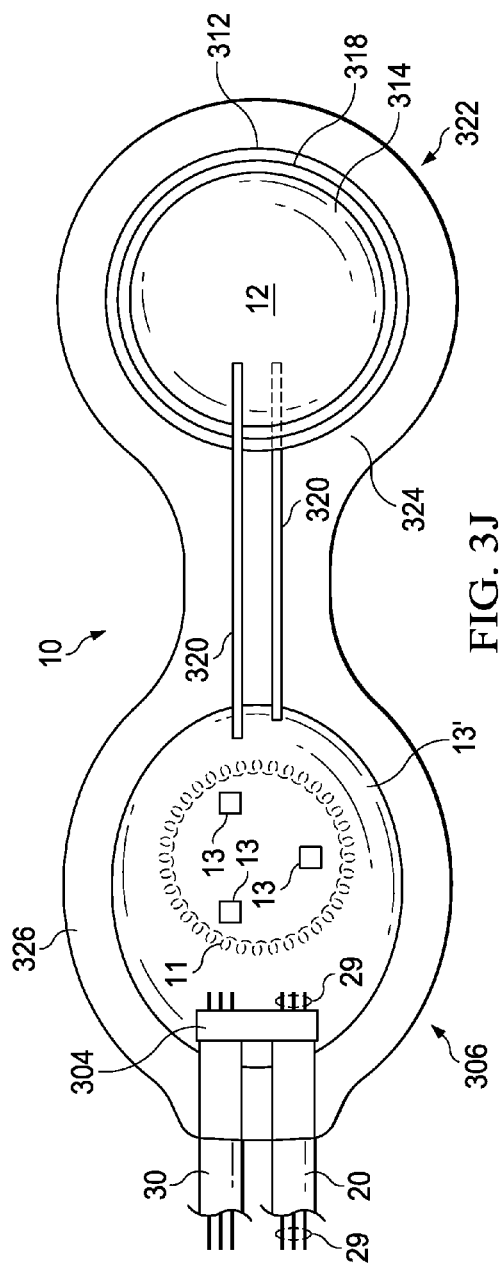
FIG. 3I
FIG. 3J

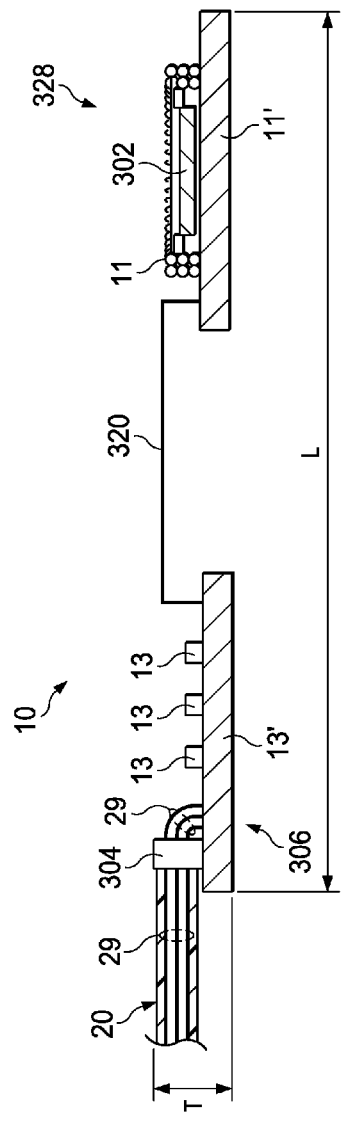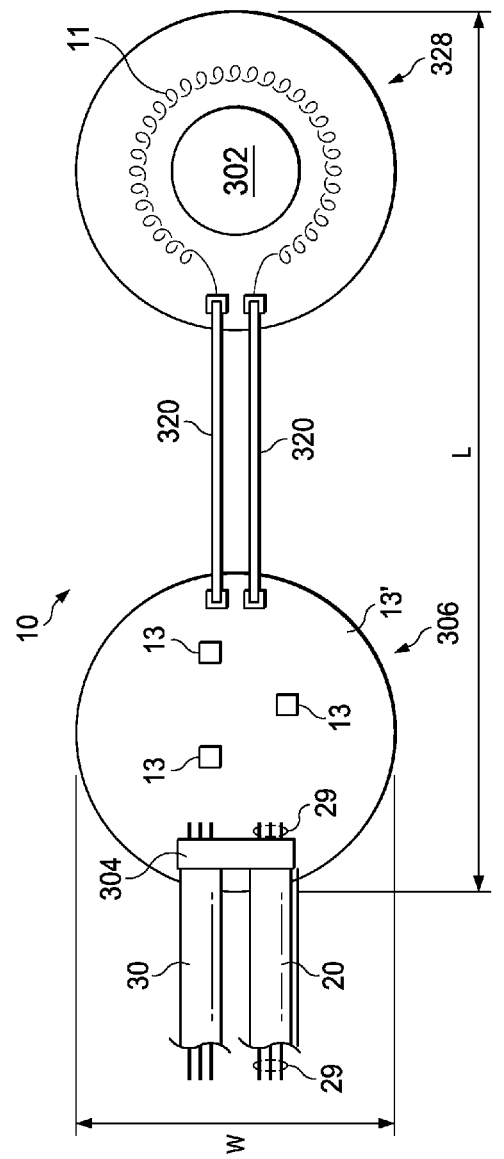

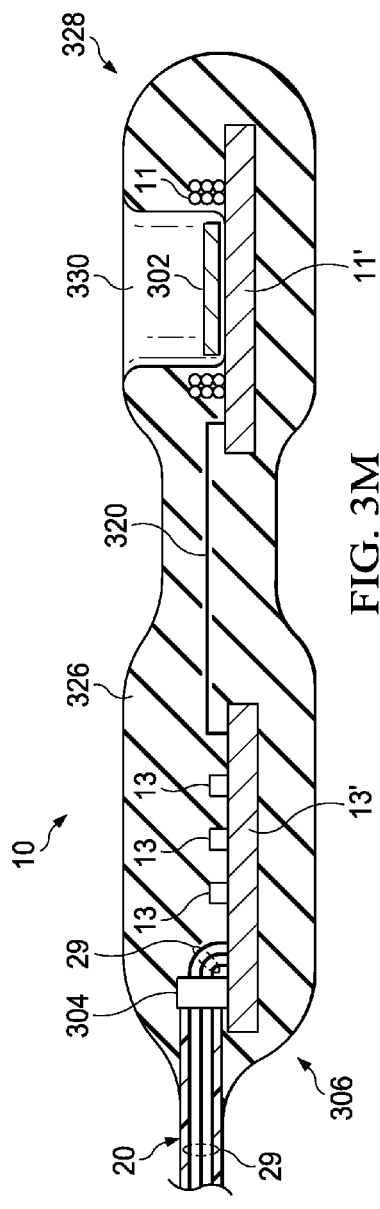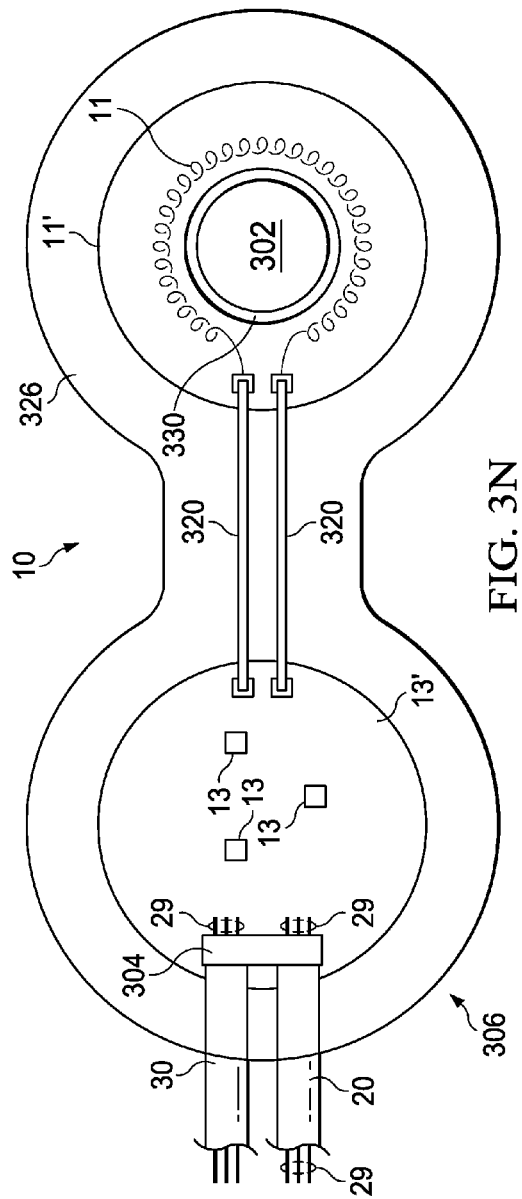
FIG. 3M
FIG. 3N

SURGICAL METHOD FOR IMPLANTABLE HEAD MOUNTED NEUROSTIMULATION SYSTEM FOR HEAD PAIN

CROSS-REFERENCE TO RELATED APPLICATIONS

This application is a continuation-in-part of U.S. patent application Ser. No. 14/879,943, filed on Oct. 9, 2015, entitled SURGICAL METHOD FOR IMPLANTABLE HEAD MOUNTED NEUROSTIMULATION SYSTEM FOR HEAD PAIN, which published on Feb. 4, 2016 as U.S. Application Publication No. 2016-0030746. U.S. patent application Ser. No. 14/879,943 is a continuation-in-part of U.S. patent application Ser. No. 14/717,912, filed May 20, 2015, entitled IMPLANTABLE HEAD MOUNTED NEUROSTIMULATION SYSTEM FOR HEAD PAIN, which is a continuation of U.S. patent application Ser. No. 14/460,139, filed Aug. 14, 2014, published on Apr. 23, 2015 as U.S. Patent Application Publication No. 2015-0112406, now U.S. Pat. No. 9,042,991, issued on May 26, 2015, which claims benefit of U.S. Provisional Application No. 61/894,795, filed Oct. 23, 2013, entitled IMPLANTABLE HEAD MOUNTED NEUROSTIMULATION SYSTEM FOR HEAD PAIN. U.S. application Ser. Nos. 14/879,943, 14/717,912, 14/460,139 and 61/894,795, U.S. Patent Application Publication Nos. 2016-0030746, 2015-0112406, and U.S. Pat. No. 9,042,991 are incorporated by reference herein in their entirety.

This application is related to U.S. patent application Ser. No. 14/460,111, filed Aug. 14, 2014, published on Feb. 19, 2015 as U.S. Patent Application Publication No. 2015-0051678, entitled IMPLANTABLE NEUROSTIMULATION LEAD FOR HEAD PAIN, which claims benefit of U.S. Provisional Application No. 61/865,893, filed Aug. 14, 2013. U.S. application Ser. Nos. 14/460,111 and 61/865,893 and U.S. Patent Application Publication No. 2015-0051678 are incorporated by reference herein in their entirety.

TECHNICAL FIELD

The present disclosure relates generally to a head located implantable neurostimulation system and, specifically, to methods of implanting a fully head located cranial and peripheral neurostimulator system that is utilized for the purpose of treating chronic head pain.

BACKGROUND

Neurostimulation systems comprising implantable neurostimulation leads are used to treat chronic pain. Conventional implantable peripheral neurostimulation leads are designed for placement in the spinal canal as part of a spinal cord stimulation system, and for the therapeutic purpose of treating various forms of chronic back and extremity pain.

Until the present invention, implantable neurostimulator systems for head pain essentially involved deep brain stimulators, where leads were positioned in the substance of the brain itself; traditional spinal cord stimulator systems that were adopted and adapted for the treatment of head pain; or implantable systems for neurostimulation of the vagus nerve or sphenopalatine ganglion.

Historically, the most common case involves the adaption of spinal cord stimulators for the purpose of peripheral nerve stimulation, such that all publically available implantable neurostimulation systems utilized for the treatment of chronic head pain have been originally designed specifically as spinal cord stimulator systems for the therapeutic purpose of treating chronic back and extremity pain. As these systems were developed for implantation in the back, their design did not contemplate the anatomic and physiologic features unique to the head and chronic head pain, which are so significantly different from the anatomy of the spinal canal, and pathophysiology of chronic back pain, that when spinal cord stimulators were utilized for cranial implants, the clinical problems associated with these differences ultimately manifested themselves.

These well-documented and clinically significant problems relate to issues of patient safety and satisfaction, including the risk of an inadequate, or suboptimal, therapeutic response; issues with patient comfort and cosmetics; and an increased risk of surgical complications and technical problems. Several specific inherent deficiencies in device design and method of implant underlie these deficiencies and problems. Likely the most common methodological deficiency is the fact that the implantable pulse generator (IPG) must necessarily be implanted at a considerable anatomic distance for the cranial lead implants. Indeed, the leads must pass from their distal cranial implant positions across the cervical region and upper back to the IPG implant location, which are most commonly in the lower back, lower abdomen, or gluteal region. The related problems are due the fact that the leads must cross multiple anatomic motion segments (neck and back). Here, the simple motions of normal daily life produce adverse tension and torque forces on the leads across these motion segments, which in turn increase the risk of technical problems, including lead migration and/or lead fracture. A second problem relates to the relatively large size of the IPG, which contributes to local discomfort, cosmetic concerns, and the fact that should the IPG pocket become infected, the related clinical problem parallels the relatively large size of the IPG; that is, the larger the IPG, the larger the pocket, and the larger and more problematic any complicating infection. Additional inherent problems include the added risks, especially infection, wound dehiscence, discomfort, and cosmetic problems associated with the multiple additional incisions that are necessary to pass the leads from the IPG to their terminal positions in the head.

SUMMARY

In various implementations, an implantable head-located, unibody peripheral nerve stimulation system may be configured for implantation of substantially all electronics, including an on-site battery, at or near the implanted electrodes on the skull. The system may include an implantable pulse generator (IPG) from which two neurostimulating leads may extend to a length sufficient to provide therapeutic neurostimulation unilaterally over the frontal, parietal and occipital regions of the hemicranium. The system may be operable to provide medically acceptable therapeutic neurostimulation to multiple regions of the head, including the frontal, parietal and occipital regions of the hemicranium, substantially simultaneously.

Each of the leads may include an extended lead body; a plurality of surface metal electrodes disposed along the lead body, which may be divided into two or more electrode arrays; and a plurality of internal electrically conducting metal wires running along at least a portion of the length of the lead body and individually connecting an internal circuit of the IPG to individual surface metal electrodes. The extended lead body may comprise a medical grade plastic. The IPG may include a rechargeable battery, an antenna coil, and an application specific integrated circuit (ASIC). The IPG may be configured for functionally connecting with an external radiofrequency unit. The external radiofrequency unit may be operable to perform various functions including recharging the rechargeable battery, diagnostically evaluating the IPG, and programming the IPG.

Implementations may include one or more of the following features. The IPG may be of proper aspect ratio with respect to the specific site of intended implantation in the head, such as an area posterior to and/or superior to the ear. There may be an external portable programming unit that is capable of achieving a radiofrequency couple to the implanted IPG. The IPG may have a rechargeable battery as a power source. The rechargeable battery may be inductively recharged through the skin.

Implementations may include one or more of the following features. A neurostimulating lead may not include a central channel for a stylet. A neurostimulating lead may have a smaller diameter than conventional leads.

Implementations may include one or more of the following features. The system may include the disposition of a sufficient plurality of surface electrodes over a sufficient linear distance along the neurostimulating leads to enable medically adequate therapeutic stimulation across multiple regions of the head, including the frontal, parietal, and occipital region of the hemicranium substantially simultaneously. The extended array of surface electrodes may be divided into two or more discrete terminal surface electrode arrays. The linear layout of the multiple surface electrode arrays may include at least one array positioned over the frontal region, at least one array positioned over the parietal region, and at least one array positioned over the occipital region.

Specific intra-array design features may include variations in the specific number of electrodes allotted to each group; the shape of the electrodes, e.g., whether the electrodes are cylindrical or flattened; the width of each electrode within each array, and the linear distance intervals of separation of the electrodes within each array.

Various implementations may include a plurality of connection ports that can be connected with a plurality of leads and thus allow for attaching additional leads.

In various implementations, methods of treating chronic pain may include methods of treating chronic head and/or face pain of multiple etiologies, including migraine headaches; and other primary headaches, including cluster headaches, hemicrania continua headaches, tension type headaches, chronic daily headaches; further including secondary headaches, such as cervicogenic headaches and other secondary musculoskeletal headaches.

In various implementations, methods of treating chronic pain may include methods of treating head and/or face pain of multiple etiologies, including neuropathic head and/or face pain, nociceptive head and/or face pain, and/or sympathetic related head and/or face pain.

In various implementations, methods of treating chronic pain may include methods of treating head and/or face pain of multiple etiologies, including greater occipital neuralgia, as well as the other various occipital neuralgias, supraorbital neuralgia, auriculo-temporal neuralgia, infraorbital neuralgia, and other trigeminal neuralgias, and other head and face neuralgias.

In various implementations the unibody neurostimulation system with two leads, including one with multiple arrays, is fully implanted with all components positioned within the subcutaneous layer of the skin and without the requirement of sutures, anchors, or other fixation devices to fix the systems, or portions thereof in position.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which:

FIG. 1 depicts a side view of a head-located, unibody neurostimulator system for migraine and other head pain. The system features an implantable pulse generator (IPG) from which two neurostimulating leads extend—a Fronto-Parietal Lead (FPL) and an Occipital Lead (OL). Each lead includes a plurality of electrodes in a distribution and over a length to allow full unilateral coverage of the frontal, parietal, and occipital portions of the head;

FIG. 2 depicts a side view of a Frontal Electrode Array (FEA) with Internal Wires. The FEA is disposed over the distal portion (such as 8-10 cm) of the FPL, which anatomically places it over the frontal region, and specifically over the supraorbital nerve and other adjacent nerves of the region. In general the layout, disposition and connections of the Internal Wires and Surface Electrodes disposed over the Parietal Electrode Array (PEA) and the Occipital Electrode Array (OEA) are the same as that depicted for the FEA;

INDEX OF ELEMENTS

Figure 3G:
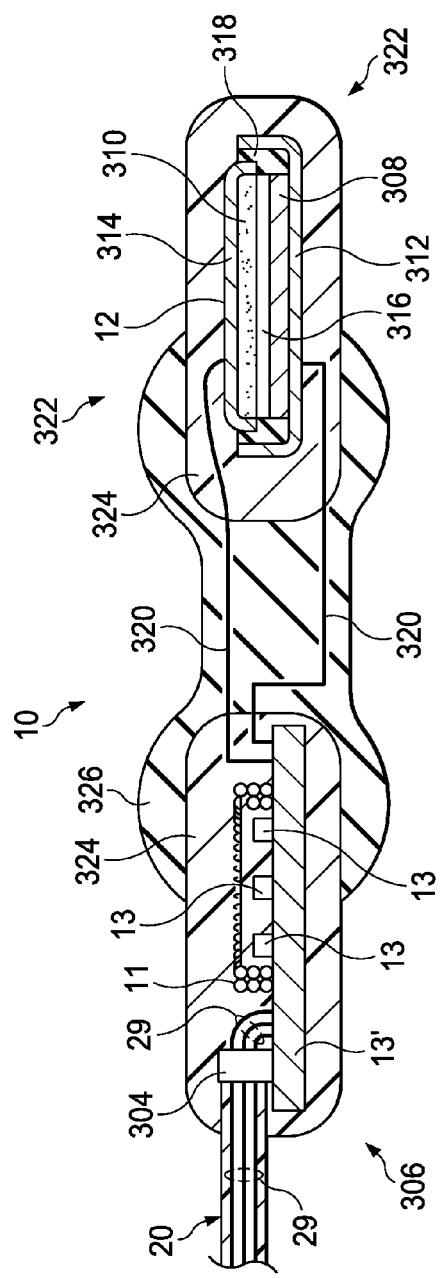
FIG. 3 depicts a side view of the Internal Wires exiting from the IPG's Internal Circuit enroute to the Surface Electrodes disposed over the FPL and the OL.
FIGS. 3A-3N illustrate embodiments of the IPG.

10: Implantable Pulse Generator
10a: Implantable Pulse Generator Passed Subcutaneously
11: Antenna
302: Battery
13: Application Specific Integrated Circuit
14: Medical Plastic Cover
20: Fronto-Parietal Lead
20a: Plastic Body Member
20b: Fronto-Parietal Lead Passed Subcutaneously
21 Distal End
22: Proximal End
22a: Proximal Lead Segment
22b: Proximal Lead Segment Passed Subcutaneously
23: Distal Non-Stimulating Tip
24: Surface Metal Electrode
25: Frontal Electrode Array
26: Parietal Electrode Array
27: Inter-Array Interval
28 Point of Cross Section FIG. 4
28a: Distal Lead Segment Passed Subcutaneously
29 Lead Internal Wire
30 Occipital Lead
30b: Occipital Lead Passed Subcutaneously
31 Distal End
32 Proximal End
32a Proximal Lead Segment
33 Distal Non-Stimulating Tip
34 Surface Metal Electrode
35 Occipital Electrode Array
36 Interelectrode Distance
37 Surface Electrode Width
38 Lead Internal Wire
39 Plastic Body Member
40: Portable Programmer
41: Liquid Crystal Display
42: Remote Charge Status
43: IPG Charge Status
44: Program Running Icon
44a: LCD Head Graphic
45: Right & left Toggle Buttons
46: Increase & Decrease Buttons
47: Confirm/Enter Button
48: On/Off Button
49: Top View with Lock Button
50 Occipital Region of Head
51a: Cross Section of Greater Occipital Nerve
51 Greater Occipital Nerve
52 Lesser Occipital Nerve
53 Third Occipital Nerve
60 Parietal Region of Head
61 Auriculo-temporal Nerve
62: Zygomaticotemporal Nerve
63: Apex of Pinna
64: Vertical Pre-Pinna Line
65: Vertical Mid-Pinna Line
66: Vertical Post-Pinna Line
67: Horizontal Supra-Pinna Line
68: Supra-auricular Subcutaneous Incision
68a: Lower Point of Supra-auricular Subcutaneous Incision
68b: Blowup of Supra-auricular Subcutaneous Incision
69: Temple Subcutaneous Incision
69a: Lower point of Temple Subcutaneous Incision
70 Frontal Region of Head
71 Supraorbital Nerve
72: Supratrochlear Nerve
80: Cross Section of Scalp
81: Dermis
82: Subcutaneous Tissue Layer
83: Fascia
84: Muscle Layer
85: Aponeurosis
86: Boney Skull
87: Arrow Indicating Direction of Fronto-Parietal Lead
88: Skin Incision Depth to Subcutaneous Layer
90: Tubular Metal Introducer
91: Scalpel
92: Local Anesthetic Infiltrated in Skin
93: Syringe
94: Step Dilator
95: Peel-Away Introducer
96: Flex Elevator
96a: Flex Elevator Handle
96b: Flex Elevator Tissue Spatula

DETAILED DESCRIPTION

Referring now to the drawings, wherein like reference numbers are used herein to designate like elements throughout, the various views and embodiments of implantable head located neurostimulation system for head pain are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

A. Introduction

The present disclosure provides a fully head located implantable peripheral neurostimulation system designed for the treatment of chronic head pain. It incorporates multiple elements and features that take into account the unique anatomic, physiologic, and other related challenges of treating head pain with implantable neurostimulation, thereby greatly improving on therapeutic response, patient safety, medical risk, and medical costs, which combine to improve overall patient satisfaction.

Prior implantable peripheral neurostimulation systems and components, including leads and pulse generators, have been designed and developed specifically as spinal cord stimulator systems and for the specific therapeutic purpose of treating chronic back and extremity pain. Over the years, these spinal cord stimulators were ultimately adopted and adapted for use as implantable peripheral nerve stimulators for the treatment of migraine headaches, and other forms of chronic head pain; however, they were so utilized with full recognition of the inherent risks and limitations given that they were developed only to address, and accommodate to, the unique anatomic and physiologic features of the back and chronic back pain.

U.S. Provisional Patent Application Ser. No. 61/865,893 describes the manifold problems associated with the application of spinal cord stimulators for head pain as fundamentally due to design flaws associated with, and inherent to, the use of an implantable therapeutic device in an area of the body that it was not designed for.

Indeed, the anatomy of the head, and the pathophysiology of headaches, and other forms of head pain, are so significantly different from the anatomy of the spinal canal, and pathophysiology of chronic back pain, that when spinal cord stimulators are utilized for cranial implants, the clinical problems associated with these differences manifest themselves. Importantly, these well-documented problems are clinically very significant and include issues of patient safety and satisfaction, the risk of an inadequate, or suboptimal, therapeutic response; and issues with patient comfort and cosmetics; as well as a recognized increased risk of surgical complications and technical problems.

These medical issues stem from the design of conventional leads and the IPG. Conventional lead designs include a relatively large diameter, a cylindrical shape, (often) inadequate length and the necessity of implanting the IPG in the torso and distant from the distal leads, and a number and disposition of the surface electrodes and active lead arrays that do not match the requirements. A cylindrical lead of relatively large diameter results in increased pressure on, and manifest tenting of, the overlying skin, particularly of the forehead. Because conventional leads are of inadequate length to extend from the head to the IPG implant site, commonly in the lower back, abdomen, or gluteal region, lead extensions are often employed, and there are attendant risks of infection, local discomfort, and cosmetic concerns.

With respect to prior leads: 1) There is only a single array of electrodes, with common lead options including 4, 8, or 16 electrodes disposed over that single array; 2) The array is relatively short with most leads having an array of from 5-12 cm in length; 3) Within this single array, the individual electrodes are disposed uniformly with constant, equal inter-electrode distances. This results in the need to implant multiple (often four or more) of the conventional leads to adequately cover the painful regions of the head.

There are several practical clinical outcomes that result from the use of prior leads for the treatment of chronic head pain. First, since they comprise a single, relatively short active array, the currently available leads provide therapeutic stimulation to only a single region of the head; that is, they can provide stimulation to only the frontal region, or a portion of the parietal region, or a portion of the occipital region. Therefore, if a patient has pain that extends over multiple regions, then multiple separate lead implants are required—basically one lead implant is required for each unilateral region. A great majority of patients with chronic headaches experience holocephalic pain; that is they experience pain over the frontal and parietal and occipital regions bilaterally. Therefore, commonly these patients will need 4 to 7 leads implanted to achieve adequate therapeutic results (2 or 3 leads on each side).

Second, the need for multiple leads includes considerable added expense, and more importantly, added medical risk associated with adverse events attendant to the multiple surgical procedures. Such adverse events include an increased risk of infection, bleeding, and technical issues with the leads, e.g., lead fracture, lead migration, and local irritation.

Third, as the clinical database discloses, the inter-electrode spacing may be of central therapeutic significance. That is, for example, whereas commonly pain over the occipital region is consistently effectively treated by quadripolar leads (leads with four evenly spaced electrodes) that have the electrodes relatively widely spaced apart (approximately a cm or more apart), clinically it is often found that electrodes configurations that are more narrowly spaced may be more effective over the supraorbital nerve and regions. Thus, a quadripolar lead that has the electrodes only 1-2 mm apart may be more effective in this region, as it allows for more precise control of the delivered electrical pulse wave delivery.

Inter-electrode spacing is also of therapeutic significance. For example, whereas pain over the occipital region is commonly treated effectively by systems incorporating relatively widely-spaced quadripolar leads (four electrodes at approximately 1 cm or more intervals), more narrowly spaced contacts are often more effective over the supraorbital region.

When an IPG implant designed for spinal cord stimulation systems is employed as a peripheral nerve stimulator for head pain, several outcomes result. First, the IPG is implanted at a considerable anatomic distance for the cranial lead implants. Indeed, the leads must pass from their distal cranial implant positions across the cervical region and upper back to the IPG implant location, which are most commonly in the lower back, lower abdomen, or gluteal region. The leads must cross multiple anatomic motion segments, including the neck and upper back and/or chest at a minimum, and commonly include the mid back, lower back and waist segments, as well. The simple motions of normal daily life produce adverse tension and torque forces on the leads across these motion segments, which in turn increases the risk of various outcomes, including lead migration and/or lead fracture. In addition, the relatively large size of a spinal cord stimulator IPG contributes to local discomfort, cosmetic concerns, and increased risk of infection that may become larger and harder to treat in proportion to the size of the IPG pocket.

The present disclosure is directed to an implantable head-located unibody peripheral neurostimulation system that includes an IPG from which two neurostimulating leads extend to a length sufficient to allow for therapeutic neurostimulation unilaterally over the frontal, parietal and occipital regions of the head.

The present disclosure addresses and effectively solves problems attendant to publically available leads. The most important of these is the fact that current leads can only adequately stimulate a single region of the head due to design element flaws associated with terminal surface electrode number and disposition. The disclosure additionally addresses and solves other problems inherent with the currently available leads, including problems with cosmetics and patient comfort, particularly over the frontal regions, due the uncomfortable pressure placed on the skin of the forehead, due the cylindrical shape and relatively large diameter of the distal portion of the lead. Finally, the lead of the present disclosure solves the currently available leads' problem of inadequate lead length to reach a gluteal location of the implantable pulse generator, which therefore necessitates the additional risk and expense of further surgery to implant lead extensions.

In one aspect, the implantable, head-located, neurostimulation system for head pain is operable for subcutaneous implantation in the head, and to provide neurostimulation therapy for chronic head pain, including chronic head pain caused by migraine and other headaches, as well as chronic head pain due other etiologies. The peripheral neurostimulator system disclosed herein takes into account unique anatomic features of the human head, as well as the unique, or singular, features of the various pathologies that give rise to head pain, including migraine and other headaches, as well as other forms of chronic head pain. This lead design for implantation in the head for chronic head pain recognizes that thus far all commercially available systems that have been clinically utilized for implantation as a peripheral neurostimulator system were actually originally designed specifically for placement in the epidural space, as part of a spinal cord stimulation system, for the therapeutic purpose of treating chronic back and/or extremity pain. Thus, there are currently no commercially available leads or full system that have designs in the public domain, that have been designed and developed for use in the head and for head pain.

In another aspect, the implantable, head-located, neurostimulation system for head pain comprises multiple design features, including disposition of a sufficient plurality of surface electrodes over a sufficient linear distance along the distal lead, such as will result in a lead that, as a single lead, is capable of providing medically adequate therapeutic stimulation over the entire hemicranium; that is, over the frontal, parietal, and occipital region substantially simultaneously. Currently available systems, which were designed specifically for epidural placement for chronic back pain, are capable of only providing stimulation over a single region; that is over either the frontal region alone, or the parietal region alone, or the occipital region alone.

Currently available leads, which were designed specifically for epidural placement for chronic back pain, are capable of only providing stimulation over a single region; that is over either the frontal region alone, or the parietal region alone, or the occipital region alone.

In yet another aspect, the implantable, head-located, neurostimulation system for head pain comprises multiple design features, including the physical grouping of the extended array of surface electrodes into three or more discrete terminal surface electrode arrays. The linear layout of these two or more (preferably three or more) surface electrodes arrays is designed such that following implantation there would be at least one array positioned over the frontal region, at least one array positioned over the parietal region, and at least one array positioned over the occipital region. This feature further improves upon therapeutic effectiveness of the extended terminal surface electrode array sufficient for hemicranial stimulation by allowing for more precise control of the therapeutic neurostimulation parameters.

In still another aspect, the implantable, head-located, neurostimulation system for head pain comprises multiple design features, including incorporating individual design features within each of the three or more individual surface electrode arrays; examples of such intra-array design features would include the specific number of electrodes allotted to each group; whether the electrodes are cylindrical or flattened; the width of each electrode within each array, and the linear distance intervals of separation of the electrodes within each array. This feature further improves upon therapeutic effectiveness of the extended terminal surface electrode array sufficient for hemicranial stimulation, and the grouping of these electrodes into three or more separate surface electrode arrays, by providing each specific array location with a unique intra-array design that takes into account, and thereby seeks to optimize, design elements that are known to be possibly or likely beneficial to the therapeutic end result, given the anticipated post-implant anatomic location of that array.

In yet another aspect, the implantable, head-located, neurostimulation system for head pain comprises multiple design features, including incorporating individual design features into a single lead design and thereby achieving additive benefits.

In still another aspect, an implantable, head-located, neurostimulation system for head pain results in a marked decrease in the number of separate lead implants required to adequately treat a single patient. A single implant will provide the same therapeutic anatomic coverage that it would take the implantation of three or four of the currently available leads; that is, instead of the current implant, which often calls for three or more leads to be implanted to provide adequate hemicranial coverage, the same anatomic region may be covered with a single stimulator lead implant. The lead can provide extended coverage over the full hemicranium; that is achieving medically acceptable neurostimulation unilaterally over the frontal, parietal, and occipital regions simultaneously. In contrast, publically known leads are able to consistently provide medically acceptable neurostimulation therapy only over a single region; meaning that it would require three separate surgically placed lead implants to achieve the same therapeutic coverage of a single implant of a lead of the present disclosure. This will decrease the total number of surgeries required, as well as the extent of each individual surgery, for many patients.

In another aspect, the present disclosure is directed to a system that is fully localized to the head, which obviates the requirement of currently available systems of having long leads and extensions extending across the neck and back to IPG locations commonly in the low back and gluteal region, and thereby decreases the risk of problems attendant to such long leads and extensions, including discomfort, infection, technical extension issues such as fracture, and other morbidities. This ultimately results in a decreased number of surgeries required by a patient.

In other aspects the system may include one or more of the following features. A neurostimulating lead may not require a central channel for a stylet, which would be necessary to secure the lead against migration. A neurostimulating lead may have a smaller diameter than currently available leads.

In other aspects the system may include one or more of the following features. The system may include the disposition of a sufficient plurality of surface electrodes over a sufficient linear distance along the system's leads to enable medically adequate therapeutic stimulation across multiple regions of the head, and preferably the entire hemicranium; that is, over the frontal, parietal, and occipital region simultaneously. The extended array of surface electrodes may be divided into two or more discrete terminal surface electrode arrays, each capable of being designed for the particular associated region to be stimulated. The preferred linear layout of these multiple surface electrode arrays includes at least one array positioned over the frontal region, at least one array positioned over the parietal region, and at least one array positioned over the occipital region.

In other aspects, intra-array design features may include variations in the specific number of electrodes allotted to each group; the shape of the electrodes, e.g., whether the electrodes are cylindrical or flattened; the width of each electrode within each array, and the linear distance intervals of separation of the electrodes within each array.

In other aspects, the system may include a plurality of connection ports that can be connected with a plurality of leads and thus allow for attaching additional leads should they later be required.

In another aspect, an implantable, head-located, neurostimulation system for head pain comprises multiple design features; including features aimed at improving patient safety by improving the incidence of adverse events, including the risk of infection, as well as the risk and incidence of known technical problems associated with implanted leads, including lead migration and lead fracture, amongst others. The lead may comprise two or more (i.e. three or more) surface electrode arrays, each uniquely designed, that are disposed over a sufficient lead length to allow for medically acceptable therapeutic neurostimulator coverage of at least regions within the supraorbital, parietal, and occipital cranial regions. To achieve the same clinical coverage from a prior art implant, it would require three or more separately surgically implanted leads that are first implanted, followed by waking the patient up and activating the electrodes to determine if they are properly placed, and once the surgeon is satisfied, the leads are connected to an IPG and the IPG disposed in a pocket somewhere in the body, typically in the lower torso. Therefore, by reducing the number of surgical incisions, as well as the number of surgically implanted leads, the associated risks of adverse events are proportionally diminished.

In yet another aspect, an implantable, head-located, neurostimulation system for head pain may treat chronic head and/or face pain of multiple etiologies, including migraine headaches; and other primary headaches, including cluster headaches, hemicrania continua headaches, tension type headaches, chronic daily headaches, transformed migraine headaches; further including secondary headaches, such as cervicogenic headaches and other secondary musculoskeletal headaches; including neuropathic head and/or face pain, nociceptive head and/or face pain, and/or sympathetic related head and/or face pain; including greater occipital neuralgia, as well as the other various occipital neuralgias, supraorbital neuralgia, auriculotemporal neuralgia, infraorbital neuralgia, and other trigeminal neuralgias, and other head and face neuralgias.

In other aspects, an implantable, head-located, neurostimulation system for head pain may not require a central channel for stylet placement over its distal (frontal) portions. The lead may improve patient comfort and cosmetics by virtue of its relatively small diameter over the distal portions of the lead, partially due the lack of a central stylet channel, as well as due to a progressive decrease in the number of internal wires continuing after each terminal electrode. The lead may further improve cosmetic appearance and patient comfort by incorporating a flattened lead design for that portion of the lead expected to be over the frontal portion of the head. The lead may be compatible with currently available implantable pulse generators. The lead may incorporate an electrode array design that is capable as a single lead of providing medically acceptable neurostimulation coverage over the supraorbital, auriculotemporal, and occipital nerves unilaterally. The lead may be of sufficient length to adequately reach all common pulse generator locations, thereby potentially obviating the need for lead extensions and in turn decreasing the risk of problems attendant to such extensions, including discomfort, infection, technical extension issues such as fracture, and other morbidities. The single lead may be operable to provide medically acceptable neurostimulation coverage that treats head pain over the frontal, lateral, and posterior regions. The single lead may be operable to provide medically acceptable therapeutic neurostimulation coverage that would otherwise often require unilateral leads (six total leads if, as is common, the pain is global/holocephalic), thereby resulting in a decrease in the number of patients that require more than one associated Implantable Pulse Generator (IPG). Currently available IPGs are capable of accepting a maximum of four leads, each having the ability to cover only one anatomic region, as each lead only has one active array. The lead may include a progressively tapering diameter over the lead segment containing t three active arrays, a feature serving clinical improvements in patient comfort and cosmetics. The lead may further comprise a distal array disposed over a thin, flattened terminal portion of the lead, which is the portion intended to be positioned over the supraorbital (frontal) region, a feature serving clinical improvements in patient comfort and cosmetics.

Thus the present disclosure provides for a peripheral neurostimulation lead that is uniquely designed for subcutaneous implantation in the head as a therapy for chronic head pain, and is designed to solve the known design issues associated with current leads, as the lead of the present disclosure seeks to optimize the therapeutic response, improve patient comfort, improve cosmetics, reduce the number of surgical leads required, reduce medical risk, and reduce medical costs.

B. Overview

Turning now to the drawings, which depict the system and several of its components in various aspects and views, and in which similar reference numerals denote similar elements. The drawings illustrate an IPG from which two neurostimulating leads may extend to a length sufficient to allow for therapeutic neurostimulation unilaterally over the frontal, parietal and occipital regions. The leads include an extended plastic lead body; a plurality of surface metal electrodes disposed along the lead, which may be divided into two or more electrode arrays; a plurality of internal electrically conducting metal wires running along at least a portion of its length and individually connecting the IPG's internal circuit to individual surface metal electrodes. The implantable pulse generator includes a rechargeable battery, an antenna coil, and ASIC. The system may be operable to provide medically acceptable therapeutic neurostimulation to multiple regions of the head, including the frontal, parietal and occipital regions simultaneously, and three figures demonstrate various views of this feature as the lead is depicted in-situ.

C. Full Head-Located Neurostimulator System

FIG. 1 depicts a side view of a full neurostimulator system, which consists of an implantable pulse generator (IPG) 10 along with two unibody plastic lead extensions a Fronto-Parietal Lead (FPL) 20 and an Occipital Lead (OL) 30 of adequate length to extend to roughly the midline of the forehead and to the midline at the cervico-cranial junction, respectively. Arrows 28 indicate the point of cross section of FIG. 4.

Figure 5:
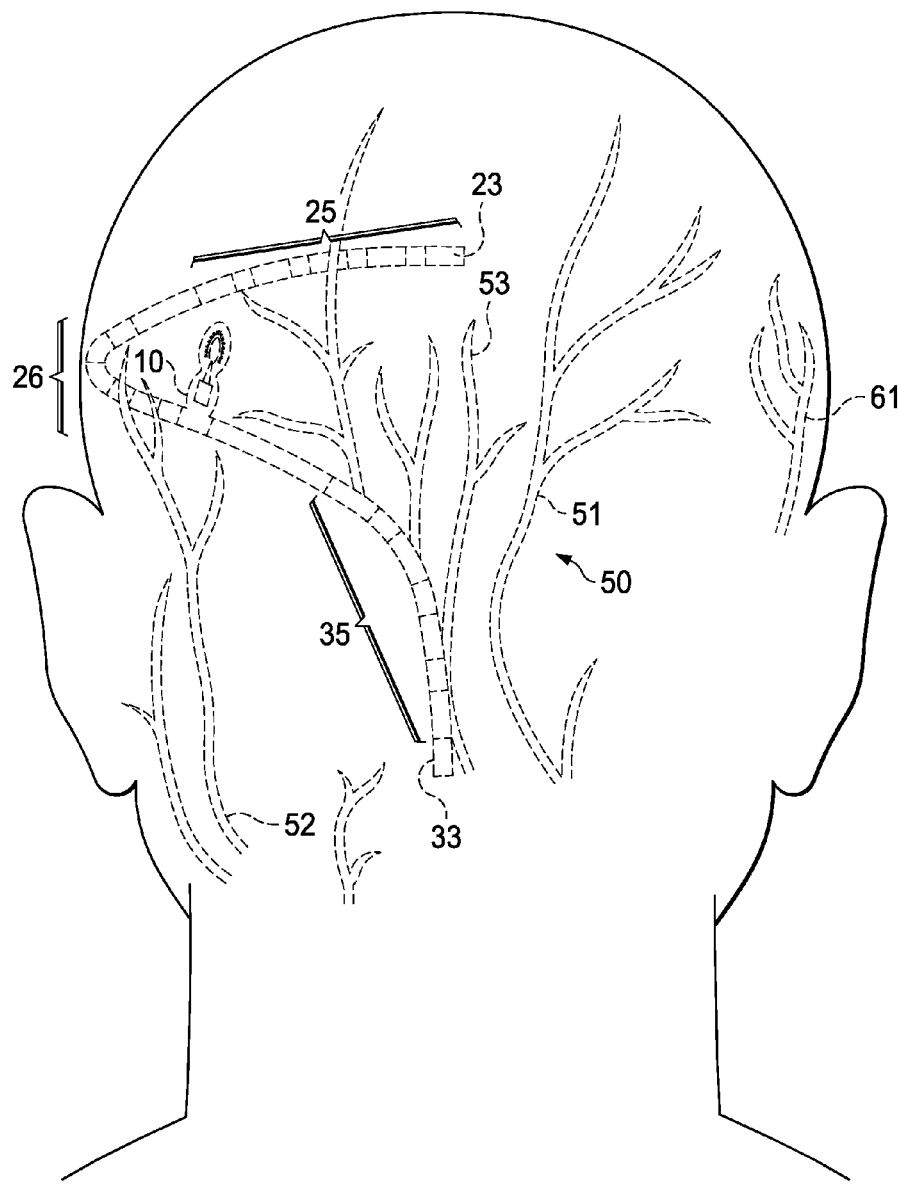
FIG. 5 depicts a rear view of a Head with a full Head-Mounted Neurostimulator System In-Situ. Prominent here is the OL depicted passing from the IPG caudally and medially across the occipital region, whereby the OEA is disposed in a fashion to cross over and cover the major associated nerves—primarily the greater occipital nerve, but typically including the lessor and/or third occipital nerve as well. Also depicted are the PEA and the FEA of the FPL as they cross and cover the primary nerves of the Parietal Region, including the auriculo-temporal nerve, and the Frontal Region, including the supraorbital nerve.
Figure 6:
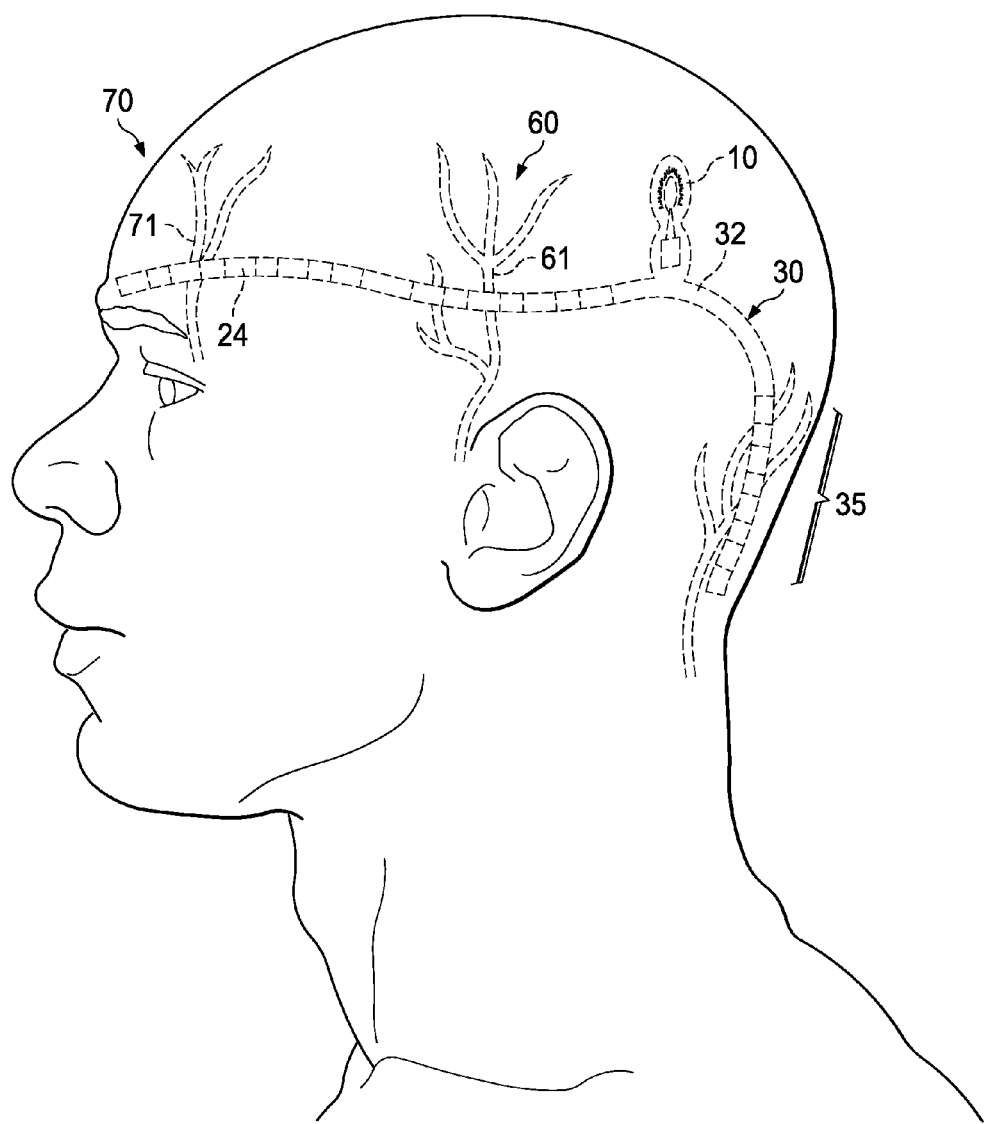
FIG. 6 depicts a side view of a Head with a full Head-Located Neurostimulator System In-Situ. Prominent here is the PEA, as it covers a portion of the Parietal Region and the major associated nerves, including the auriculo-temporal nerve, as well as adjacent cutaneous nerves. Also depicted are the courses of the distal portion of the FPL and the OL, as they pass over and cover the associated nerves of the Frontal (Supraorbital) and Occipital Regions.
Figure 7:
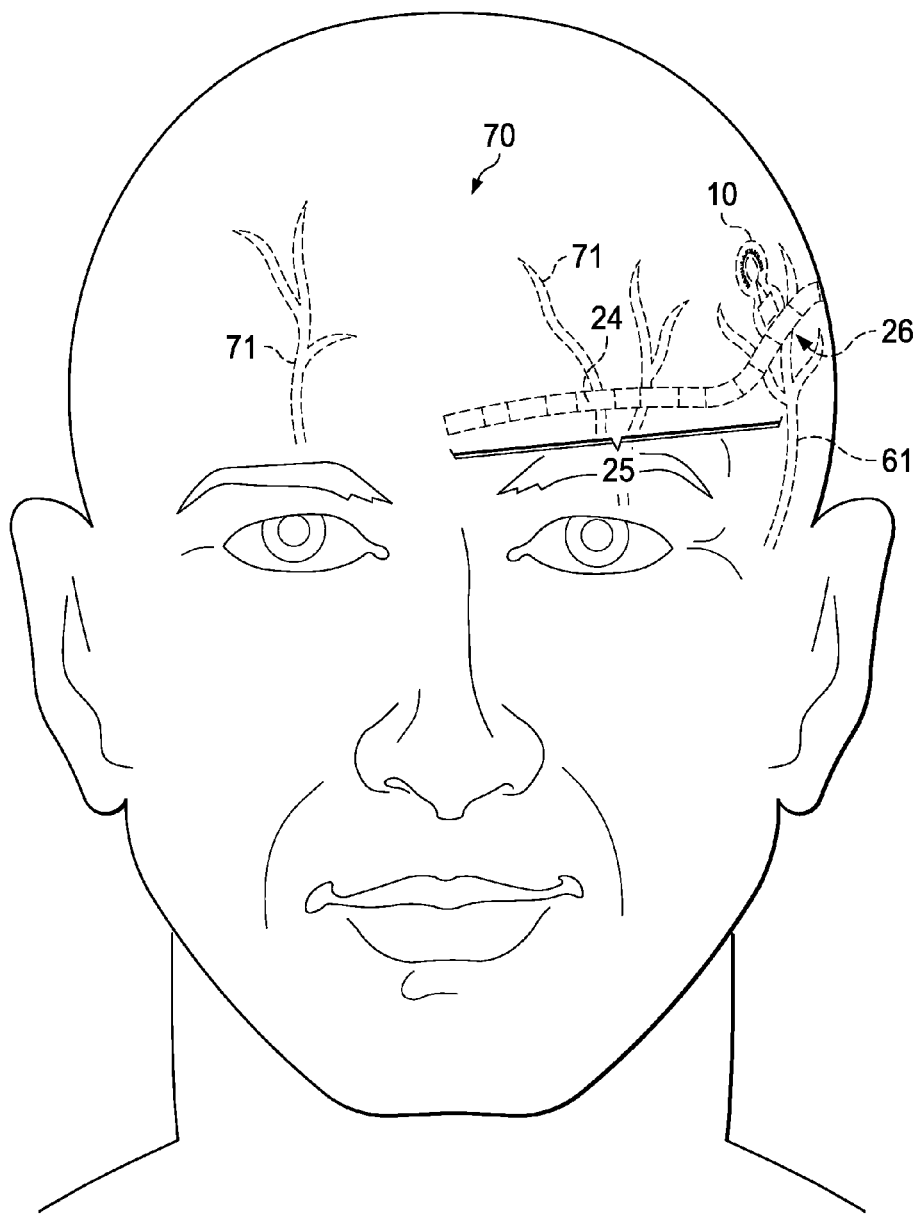
FIG. 7 depicts a front view of a Head with a full Head-Located Neurostimualtor System In-Situ. Prominent here is the FEA, as it covers a portion of the Frontal (Supraorbital) Region and the major associated nerves—primarily the supraorbital nerve, but also commonly the greater trochlear nerve, as well as adjacent nerves. Also depicted is the course of the parietal portion of the FL.

FIGS. 5, 6 and 7 depict posterior, lateral and frontal views of the system in-situ. The unit is demonstrated in an implant position where the IPG 10 is posterior and cephalad to the pinna of the ear. The drawings demonstrate the complete neurostimulator system implant subcutaneously with the FPL 20 passing over the parietal 60 and frontal 70 regions of the head in a manner that places the FEA over the supraorbital nerve 71 and the PEA over the auriculotemporal nerve 61. The OL 30 is shown passing caudally and medially over the occipital region of the head 50 such that the OEA 35 cross over the greater occipital nerve 51 and the lesser occipital nerve 52, and the third occipital nerve 53.

D. Fronto-Parietal Lead

Continuing with FIG. 1, the FPL 20 as part of the unibody construction, is connected to and extends from the IPG. The FPL 20 comprises a plastic body member 20a and a set of internal conducting wires 29.

The plastic body member 20a is an elongated, cylindrical, flexible member, which may be formed of a medical grade plastic polymer. It has a proximal end 22, a distal end 21, and may be conceptually divided into five segments along its linear dimension. Progressing from the proximal end 22, these segments sequentially include a proximal lead segment (PLS) 22a, a parietal electrode array (PEA) 26, an inter-array interval 27, a frontal electrode array (FEA) 25, and a distal non-stimulating tip 23.

Figure 4:
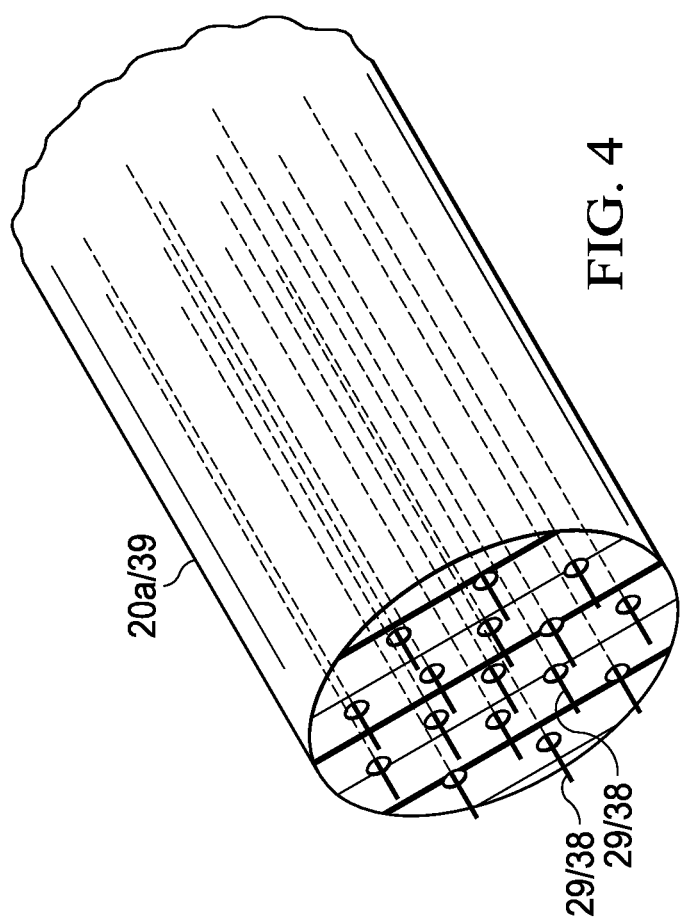
FIG. 4 depicts a cross-sectional view of a Lead Central Body comprising a Cylindrical Lead Body (with Internal Wires) between the IPG Internal Circuit and the Lead Surface Electrodes.

The lead internal wires 29 pass along the interior of the plastic body member as depicted in FIG. 4.

E. Frontal Electrode Array

Continuing with FIG. 1, the FEA 25 is disposed at the distal end of the FPL 20 and consists of a plurality of surface metal electrodes (SMEs) 24 uniformly disposed over a portion of the distal aspect of the FPL 20. Lead internal wires 29 connect to the SME 24 as depicted in FIG. 2, which represents the distal four SMEs 24 of the lead. The distal four SMEs 24 associated with the array 25 have an interelectrode spacing and design that is specific to stimulating the frontal region. Also, the number of electrodes required for the array will be a function of the particular region, the frontal region, that is being treated. As will be described hereinbelow, each of these electrodes can be designated as an anode or a cathode and any combination can be designated to be energized in a set up procedure performed by a clinician. This provides a configuration that can be adapted to a particular patient at a particular placement of the FEA 25.

F. Parietal Electrode Array

Returning to FIG. 1, the PEA 26 consists of a plurality of SMEs 24 uniformly disposed along a linear portion of the FPL. The PEA 26 is separated along the FPL from the FEA by an inter-array interval 27. It is separated on the lead from the IPG by the PLS 22a. The lead internal wires 29 connect to the individual SME 24 of the PEA in the same fashion as they do with respect to the SME of the FEA as shown in FIG. 2. As was the case with respect to the FEA 25, the SMEs 24 of the PEA 26 have an interelectrode spacing and design that is specific for stimulating the nerves in the parietal region. Also, the number of electrodes required for the array will be a function of the particular region, the parietal region, that is being treated. As will be described hereinbelow, each of these electrodes can be designated as an anode or a cathode and any combination can be designated to be energized in a set up procedure performed by a clinician. This provides a configuration that can be adapted to a particular patient at a particular placement of the array 25.

Typically, the FPL 20 is a single lead having the two arrays, 25 and 26, disposed along the length thereof. The diameter and the shape of this lead can be uniform or it can be of any shape that facilitates surgical placement of the lead. However, with a single lead, two distinct regions of the cranium can be therapeutically treated, each independently controlled by the IPG 10 via the leads 29 and each having a design via the interelectrode spacing and even the electrode configuration to facilitate the requirements of such therapeutic treatment of a particular region associated with a particular set of nerves. This, thus, requires only a single incision to feed the FPL 20 from the incision point to a particular region.

G. Occipital Lead

Continuing with FIG. 1, the occipital lead (OL) 30 is an integral part of the unibody construction, and extends from the IPG 10. It comprises a plastic body member 39 and a set of lead internal wires 38 that pass through the central cylinder of the lead to connect to a series of SMEs 34, each of surface electrode width 37, that are uniformly disposed at an interelectrode distance 36 from each other along a portion of the length of the lead. These lead internal wires 38 pass and connect in the same manner as described above for the SMEs 24 of the FEA 25 and the PEA 26 as depicted in FIG. 2 and FIG. 4.

The plastic body member 39 is an elongated, cylindrical, flexible member, which may be formed of a medical grade plastic polymer. It has a proximal end 32 and a distal end 31. Progressing along the lead from the proximal end 32, these segments sequentially include a proximal lead segment (PLS) 32a, an occipital electrode array (OEA) 35, and a distal non-stimulating tip 33.

H. Occipital Lead Array

As depicted in FIG. 1, the OEA 35 consists of a plurality of surface metal electrodes (SME) 34 uniformly disposed over a portion OL 30. Lead internal wires 38 connect to the SME 24 in the same fashion as depicted for the FEA as shown in FIG. 2. As was the case with respect to the FEA 25 and the PEA 26, the SMEs 34 of the OL 30 have an interelectrode spacing and design that is specific for stimulating the occipital region. Also, the number of electrodes required for the array will be a function of the particular region, the occipital region, that is being treated. As will be described hereinbelow, each of these electrodes can be designated as an anode or a cathode and any combination can be designated to be energized in a set up procedure performed by a clinician. This provides a configuration that can be adapted to a particular patient at a particular placement of the OL 30.

I. Implantable Pulse Generator

Referring to FIG. 1 and FIG. 3, the three primary physical and functional components of the IPG 10 include a rechargeable battery 12, an antenna 11, and an application specific integrated circuit (ASIC) 13, along with the necessary internal wire connections amongst these related components, as well as to the incoming lead internal wires 29, 39. These individual components may be encased in a can made of a medical grade metal and plastic cover 14, which itself transitions over the exiting FPL 20 and OL 30.

Battery 12 is connected to the ASIC 13 via a connection that is flexible. The overall enclosure for the battery 12, antenna 11 and ASIC 13 has a very low flat profile (seen in a top view in FIG. 1) with two lobes, one low for housing the ASIC 13 and one low for housing the battery 12. The antenna 11 can be housed in either of the lobes or in both lobes, this being a function of the coupling to an outside communication/charging source. By utilizing the two lobes and the flexible connection between the ASIC 13 and the battery 12, this allows the IPG 10 to conform to the shape of the human cranium when subcutaneously implanted without securing such to any underlying structure with an external fixator.

The ASIC 13 is operable to interface with the lines 29 in the FPL 20 and the lines 39 in the OL 34 driving the respective SMEs 24, 34. The ASIC 13 is a state machine that is configured to provide stimulation signals in the form of pulses, variable frequencies, etc., to the respective electrodes in accordance with a predetermined program. Once the program is loaded and initiated, the state machine will execute the particular programs to provide the necessary therapeutic stimulation. The ASIC 13 has memory associated there with and a communication capability, in addition to charge control to charge battery 12. Each of the set of wires 29 and 39 interface with the ASIC 13 such that the ASIC 13 individually controls each of the wires in the particular bundle of wires. Thus, each electrode in each of the arrays, 25, 26 and 35, can be individually controlled. As noted hereinabove, each electrode can be designated as an anode or a cathode, or it can even be turned off.

During a charging operation, the IPG 10 is interfaced with an external charging unit via the antenna 11 which is coupled to a similar antenna or coil in the external charging unit (not shown). The charging operation is controlled by the ASIC 13, as the battery 12, in one embodiment, can include the use of a lithium ion battery. It is important for power management to control the amount of charge delivered to the battery, the charging rate thereof and to protect the battery 12 from being overcharged.

Additionally, the ASIC 13 is capable of communicating with an external unit, typically part of the external charging unit, to transfer information thereto and receive information there from. In this manner, configuration information can be downloaded to the ASIC 13 and status information can be retrieved therefrom. Although not illustrated herein, a headset or such is provided for such external charging/communication operation.

K. Connections of Main Elements and Sub-Elements

The system may include a unibody construction to provide physical and functional continuity of the related components and sub-components. This unibody construction is basically an enclosure that encloses the entire IPG and the interface with the FPL 20 and the OL 30. The FPL 20 and the OL 30 are separate assemblies that are attached to the ASIC 13 via either a connector or via a hardwired connection. The FPL 20 and the OL 30 are totally enclosed and sealed with only the distal end of leads 29, 39 extending therefrom. Once attached to the ASIC 13, or the PC board associated there with, a material is disposed about the entire IPG 10 to provide a seal therefore which extends over the IPG 10 and the proximal ends 22 and 32 of the FPL 20 and OL 30, respectively. With such a unibody construction, a surgeon need only make one incision to subcutaneously insert the entire assembly including both the IPG 10 and associated leads in a desired region in the cranium, typically just behind the parietal bone and slightly above the mastoid bone and the pinna. This allows the FPL 20 to be fed around toward the frontal bone and the OL 30 to be fed backwards toward the occipital bone. Thus, the entire neurostimulator system will be disposed subcutaneously about the cranium and will require no anchor. Without the requirement for an anchor, there is no protuberance required in the IPG 10, allowing the IPG 10 to be completely sealed. This is facilitated by the fact that very little movement will occur with respect to the tissue surrounding the IPG 10 after implantation thereof. Due to this minimal amount of movement, no stylet will be required (but such can be incorporated if desired) to secure either the FPL 20 or the OL 30 in place to underlying fascia.

The overall mechanistic purpose of an implantable neurostimulation system is to generate and conduct a prescribed electrical pulse wave from an IPG 10 down a set of lead internal wires 29, 38 running a portion of the length of the lead to specified programmed set of SME 24, 34, whereby the current is then conducted by tissue and/or fluid to an adjacent, or nearby, set of one or more SME 24, 34, which in turn passes the signal proximally down the lead wire 29, 38 back to the IPG 10 and its ASIC 13, thus completing the circuit.

L. First Embodiment

The first embodiment provides for the implantation of the neurostimulator system that incorporates one or more of the features outlined above and includes a head-located, unibody neurostimulating system comprising an IPG 10 and at least two neurostimulating leads (FPL 20 and OL 30). The system may be implanted in a manner such that the IPG 10 and two leads 20, 30 are subcutaneously disposed as illustrated in FIG. 5, FIG. 6 and FIG. 7. The IPG 10 is capable of functionally connecting to and communicating with a portable programmer 40 and an external power source for battery recharging.

In this embodiment, the leads are constructed as described above and as depicted in the drawings. The FPL 20 is approximately 26 cm in length from its proximal end 22 to its distal end 21. The FPL 20 has a distal non-stimulating tip of approximately 3 mm in length that abuts the FEA, which may have ten SME 24 uniformly disposed over approximately 8 cm. This is followed by an inter-array interval 27 of approximately 4 cm, then the PEA, which may include eight SME 24 uniformly disposed over approximately 6 cm, and finally a proximal lead segment 22a that ends at the proximal end 22, where the lead transitions to the IPG 10 and the lead internal wires 29, 38 connect to the ASIC 13.

In this embodiment, the occipital lead may comprise a plastic body member 39 over which six SME 34 may be disposed uniformly over approximately a 10 cm length of the lead, and the lead terminates in approximately a 3 mm distal non-stimulating tip 33.

In this embodiment, the IPG 10 comprises the elements described above and depicted in the drawings, including an ASIC 13, a rechargeable battery 12, and an antenna 11, which all may be housed in a medical grade metal can with plastic cover 14. In this embodiment the dimensions of the IPG 10 measured along the outer surface of the plastic cover 14 may be approximately 5 cm by 3 cm by 0.5 mm.

The system includes a portable programmer 40 and a portable recharging unit, both of which functionally couple to the IPG through a radiofrequency mechanism.

In this embodiment, the system is capable of handling a program from the portable programmer 40 that includes such parameters as pulse amplitude, frequency and pulse width.

The procedure itself involves the permanent subcutaneous implantation of an IPG with multi-lead, multi-array neurostimulator system. The patient may have had a period of trial neurostimulation, which is standard in traditional neurostimulator evaluations but is optional here. The actual permanent implant takes place in a standard operating suite with appropriate sterile precautions and is typically performed under general anesthesia with the patient positioned prone with the hair and body prepped and draped.

While the IPG may be positioned subcutaneously anywhere over the head or upper cervical region, in this embodiment it is positioned above and behind the ear. Thus, at a position approximately 1-2 cm above the ear and a couple of cm posterior to the ear, a Supraorbital Incision of sufficient length (approximately 4-6 cm) is made to a depth sufficient to reach the subcutaneous layer. At the posterior aspect of this incision a pocket to accept the IPG is fashioned by standard dissection techniques. The pocket should be 10-20% larger than the IPG itself to allow for a comfortable fit and no undue tension on the overlying skin and/or incision. A second approximately 1-2 cm incision is made to the subcutaneous layer at a point above and anterior to the pinna of the ear in the temple region.

In this embodiment, in the supra-auricular incision, a tubular introducer with a plastic-peel away shell (Peel-Away Introducer) is advanced subcutaneously from the supra-auricular incision to the temple incision. The FL is then passed per the introducer, whereby the peel-away shell is removed leaving the proximal segment of the FL in position in the subcutaneous layer. A new Peel-Away Introducer is then advanced subcutaneously from the Temple Incision medially and commonly 1-2 cm above the eyebrow to its final position where the distal tip of the lead approximates the midline; a position that results in the frontal electrode array (FEA) over the superficial nerves of the frontal region.

In this embodiment, and prior to activation thereof, the IPG is next positioned in the previously fashioned subcutaneous pocket posterior to the supra-auricular incision. Then, from the inferior aspect of the supra-auricular incision a new peel-away introducer is advanced subcutaneously medially, and inferiorly to cross the nerve region of the occipital region such that the distal tip of the introducer approximates the midline. Per the introducer the OL is passed, whereby the Peel-Away Introducer is then removed, leaving the lead in position with its active array over the superficial nerves of the occipital region.

Following the entire placement of the complete system, including the IPG and both leads and suturing, the neurostimulator unit is then powered-up and its circuits checked. Upon recovery from anesthesia the system is turned on for the patient with a portable programmer and the multiple parameters for the system programmed to an optimal therapeutic endpoint for the patient.

In this embodiment, the implantable unit contains a multi-year battery that is capable of being recharged from an external source.

In this embodiment, the system is capable of handling a program from the portable programmer 40 that includes such parameters as pulse amplitude, frequency and pulse width. The system is charge balanced, current controlled and rechargeable at preferably intervals that exceed one week. The preferred stimulation paradigm may be current controlled, voltage controlled, or a combination of both. The pulsing may be charge balanced or charge imbalanced. The preferred work cycle is between 10 and 100%.

Turning now to FIG. 3A, there is illustrated a cross-section side view of an embodiment of the implantable pulse generator 10. In this embodiment, the IPG 10 includes a magnet 302. In some embodiments, the IPG 10 includes a magnet 302 which is used to help secure an external head unit (not shown) which includes a magnet to the patient's head. The ASIC 13 is comprised of multiple chips disposed on a substrate or supporting PC board 13'. The coil 11 and the magnet 302 are disposed on a similar PC board 11' for support thereof. They are connected together by connecting wires 12' for providing power between the coil 11 and the ASIC 13. On the opposite end of the PC board 13' from the wire connection 12', there are provided a bundle of wires 29, associated with the FPL 20, for example, although the wires 38 associated with the OL 30 are not illustrated. This bundle of wires runs through the proximal end of the lead 20. The plastic cover 14 is comprised of a medical grade plastic conformal coating that covers the entire surface of both the coil 11 and the associated structures and ASIC 13. The magnet 302 can be disposed within an open well within the cover 14 to allow removal thereof. This is typically done whenever a patient is subjected to an MRI, requiring the removal of the magnet and reinsertion of it at a later time. The cover 14 extends downward along the lead 20 to provide a seal therewith. This provides a unibody construction, such that the proximal ends of the leads 29 are attached to the PC board 13' during manufacture and then the coating 14 applied thereto.

Turning to FIGS. 3B-3J, there is illustrated several embodiments in which the IPG 10 includes a battery and one or more coatings around the IPG 10. Referring first to FIG. 3B, there is illustrated a basic IPG 10 without a covering which includes a battery 12. The ASIC 13 is disposed on a substrate 13'. The coil 11 is also disposed on the substrate 13'. The leads FPL 20 and OL 30 (only FPL 20 is visible in FIG. 3B) connect to strain relievers 304. The internal wires 29 within the leads extend from the strain relievers 304 and connect to the ASIC 13 either directly or via the substrate 13'. Rechargeable battery 12 includes the cathode 308, the anode 310, the cathode can 312, the anode cap 314, a separator 316, and a gasket 318. Electrically conductive straps 320 electrically connect the substrate 13' and the components disposed on it respectively to the cathode can 312 and the anode cap 314 of the battery 12. The straps 320 may be made of copper, gold, or any other suitable electrically conductive metal or other material. The straps 320 can be soldered to the substrate 13' and welded to the battery 12. This allows the battery 12 to provide power to the rest of the IPG 10 and the various leads (such as FPL 20 and OL 30) and allows battery 12 to be recharged by the coil 11. The substrate 13' and everything disposed on it, including the ASIC 13, the coil 11, the strain relievers 304, and the proximal ends of FPL 20 and OL 30 can be considered grouped together as an ASIC body 306. Similarly, the battery 12 can be considered a battery body 322.

Turning to FIG. 3C, there is illustrated a top view of the IPG 10 illustrated in FIG. 3B.

It should be noted that the in some embodiments of IPG 10, including variations of those illustrated in FIGS. 3B-3J, are relatively flat, as can be seen in FIGS. 3B and 3C, on which the embodiments of FIGS. 3D-3J are based. In other words, the thickness T of the IPG 10, which can be seen in FIG. 3B, is less than the length L of the IPG 10, which can be seen in FIGS. 3B and 3C. The thickness T of the IPG 10 is also less than the width W of the IPG 10, as is shown in FIG. 3C. The flat shape of the IPG 10 creates a smaller and more comfortable profile under the skin of a patient than would an embodiment that is not flat.

Turning now to FIG. 3D, there is illustrated the IPG 10 of FIGS. 3B and 3C, except that the IPG 10 of FIG. 3D has coatings of epoxy 324 around the ASIC body 306 and the battery body 322. The ASIC body 306 and the battery body 322 each have an epoxy coating 324 which encapsulates the components of each. The epoxy coatings 324 provide a hard, electrically nonconductive, impermeable barrier which protects the components of the ASIC body 322 and the battery body 322. The proximal ends of the leads FPL 20 and OL 30 are also within the epoxy coating 324 of the ASIC body 306. Note that in embodiments with more or fewer leads, the proximal end of each present lead will be within the epoxy coating 324 of the ASIC body. The ends of the straps 320 which are connected to the ASIC body 306 are within the epoxy coating 324 of the ASIC body 306, and the ends of the straps 320 which are connected to the battery 12 are within the epoxy coating 324 of the battery body 322.

Turning now to FIG. 3E, there is illustrated the IPG 10 of FIG. 3D, except that the IPG 10 has been coated with a silicone coating 326. This is the final stage of one of the embodiments created after the ASIC body 306 and the battery body 322 have been encased in epoxy coatings, as illustrated in FIG. 3D. Referring back to FIG. 3E, a silicone coating 326 encases the entireties of both the ASIC body 306 and the battery body 322, including the epoxy coatings 324 around the ASIC body and the battery body. The silicone coating 326 also encases the electrically conductive straps 320. The silicone coating 326 provides a sturdy, yet flexible, coating for the IPG 10. The section of the silicone coating 326 between the ASIC body 306 and the battery body 322 is flexible enough to allow the IPG 10 to flex and bend in the region between the ASIC body and the battery body. As described further hereinbelow with respect to FIG. 49, this flexibility allows the IPG 10 to conform to an implantation site which is not completely flat and is rounded—for example, the outside of a patient's skull. In some embodiments, such as is shown in FIG. 3E, the silicone coating 326 narrows in the region between the ASIC body 306 and the battery body 322, giving the IPG 10 increased flexibility.

Turning now to FIG. 3F, there is illustrated a top-down view of the embodiment of the IPG 10 depicted in FIG. 3F, which includes epoxy coatings 324 and a silicone coating 326. Note that the epoxy coatings 324 and the silicone coating 326 are transparent, allowing the other components, such as ASIC body 306 and battery body 322 to be visible.

Turning now to FIG. 3G, there is illustrated a cross-section side view of an embodiment of the IPG 10 which includes epoxy coatings 324 and a silicone coating 326. In this embodiment, however, the silicone coating 326 does not cover all of the IPG 10. Instead, the silicone coating 326 extends from the ASIC body 306 to the battery body 322, but covers only parts of the ASIC body and the battery body and parts of the epoxy coatings 324 of each. This embodiment is produced from the IPG 10 illustrated in FIG. 3D, in which the IPG 10 includes only epoxy coatings 324. In the embodiment of FIG. 3G, the silicone coating 326 still coats both conductive straps 320. The silicone coating 326 still creates a flexible link between the ASIC body 306 and the battery body 322. The embodiment of the IPG 10 illustrated in FIG. 3G retains a degree of flexibility which allows the ASIC body 306 and the battery body 322 to bend and flex relative to each other. In embodiments such as is illustrated in FIG. 3G, the proximal end of FPL 20 (and any other leads present) is not coated with the epoxy coating 326. Note that in these embodiments, as is the case with the embodiments illustrated in FIGS. 3E and 3F, the epoxy coating 326 narrows in the region between the ASIC body 306 and the battery body 322.

Figure 3H:
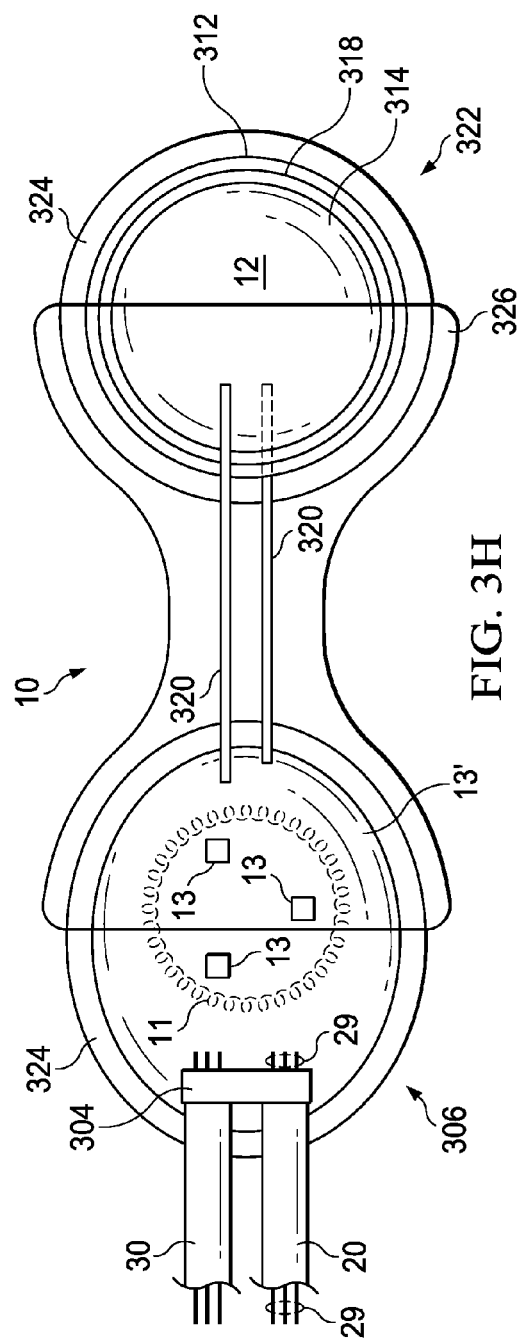

Turning now to FIG. 3H, there is illustrated a top-down view of the embodiment of the IPG 10 as illustrated in FIG. 3G. Note that the epoxy coatings 324 and the silicone coating 326 are transparent, allowing the other components, such as ASIC body 306 and battery body 322 to be visible.

Turning now to FIG. 3I, there is illustrated a cross-section side view of an embodiment of IPG 10 which includes a silicone coating 326, but no epoxy coatings 324. In these embodiments, an IPG 10 without the epoxy coatings 324, such as is illustrated in FIGS. 3B and 3C, is coated with a silicone coating 326 which encases the components of the ASIC body 306 and the battery body 322, as well the conductive straps 320. As with other embodiments which include a silicone coating 326, the silicone coating in these embodiments allows the IPG 10 to be flexible and bendable, with the ASIC body 306 and the battery body 322 being able to flex with respect to each other.

Turning now to FIG. 3J, there is illustrated a top-down view of the embodiment of IPG 10 illustrated in FIG. 3I. Note that the silicone coating 326 is transparent, allowing components such as the ASIC body 306 and the battery body 322 to be visible.

Turning now to FIG. 3K, there is illustrated another embodiment of the IPG 10 which includes a magnet 302. In this embodiment, the ASIC 13 is disposed on a substrate or PC board 13'. The substrate 13' and the components disposed on it can be considered to be grouped into ASIC body 306. The wires 29 from FPL 20 (and any other leads present) are connected to the substrate 13' and the ASIC 13. On a separate substrate or PC board 11' is disposed a magnet 302 and a coil 11. The substrate 11' and the components disposed on it can be considered to be grouped into magnet body 328. Electrically conductive straps 320 connect the ASIC body 306 and its components to the magnet body 328 and its components. The straps 320 are also electrically connected to the coil 11, allowing energy received by the coil to be transmitted to the ASIC 13 and the various leads.

Turning now to FIG. 3L, there is illustrated a top-down view of the embodiment of IPG 10 illustrated in FIG. 3K.

Variations of the embodiment of the IPG 10 illustrated in FIGS. 3K and 3L (and that of FIGS. 3M and 3N, described hereinbelow) are relatively flat, similar to the embodiments illustrated in FIGS. 3B-3J. The thickness T of IPG 10, which can be seen when viewed from the side as in FIG. 3K, is smaller than the length L, which can be seen in FIGS. 3K and 3L. The thickness T is also smaller than the width W, which can be seen when viewed from the top as in FIG. 3L.

Turning now to FIG. 3M, there is illustrated a cross-section side view of an embodiment of the IPG 10 like that illustrated in FIGS. 3K and 3L, except that this embodiment has a silicone coating 326 over it. The silicone coating 326 encases the ASIC body 306, the straps 320, and part of the magnet body 328. The coil 11 and the substrate 11' are within the silicone coating 328, but the magnet 302 is not. Instead, the silicone coating 326 includes a well 330, which is essentially a cutout in the silicone cutting which extends from the top surface of the silicone coating, above the magnet 302, down to the surface of the substrate 11'. The well 330 is shaped and sized such that the magnet 302 can be surgically removed from the IPG 10 when, for example, a procedure such as an MRI is going to be performed on the patient. The magnet 302 can be surgically reinserted into the well 330 after the procedure, or whatever necessitated the removal of the magnet 302, is complete. The well 330 allows for the surgical removal and reinsertion of the magnet 302 without having to disassemble the IPG 10 or cut open the silicone coating 326.

Turning to FIG. 3N, there is illustrated a top-down view of the embodiment of the IPG 10 that is illustrated in FIG. 3M. Note that the silicone coating 326 is transparent, allowing components such as the ASIC body 306 and the magnet body 328 to be visible.

Figure 8A:
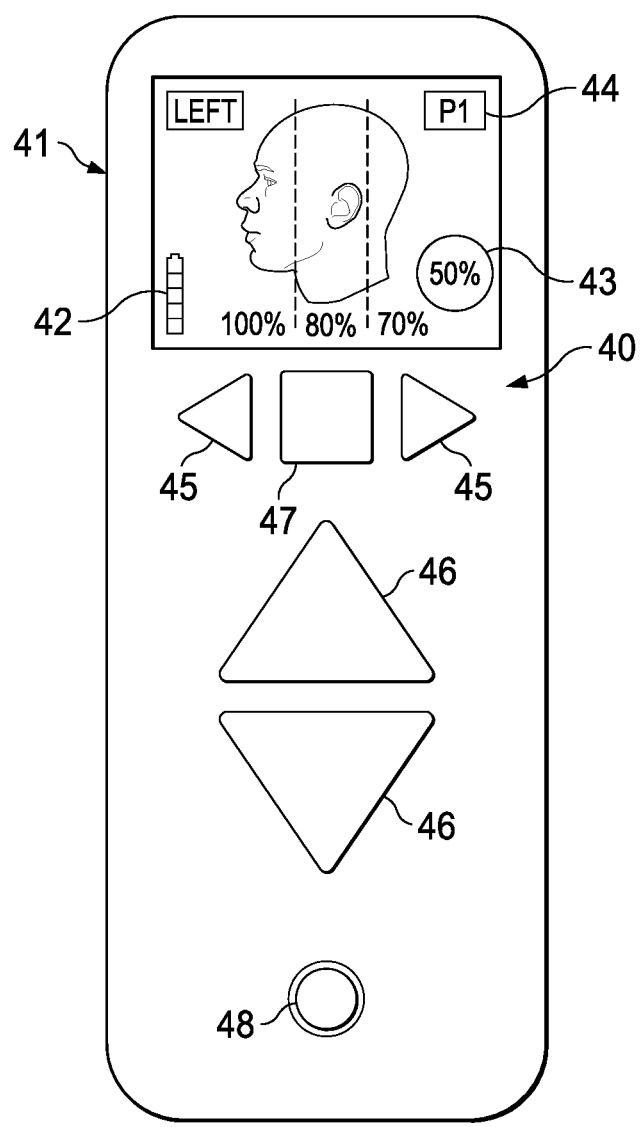
FIGS. 8A and 8B depicts a front view and a side view of a Portable Programmer for a Head-Mounted Neurostimulator System.
Figure 8B:
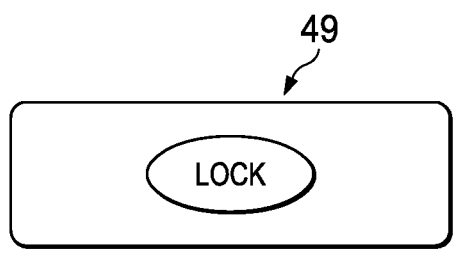

FIGS. 8A and 8B depict a front view and a top view, respectively, of a Portable Programmer 40 for a Head-Mounted Neurostimulator System. The Programmer 40 is specifically designed for application to the Head-Mounted System and specifically for use with patients with migraine and other head pain. The figure is labelled independently. On the front of the Programmer 40 is disposed a liquid crystal display 41 for displaying one side of the head of individual. In the upper left-hand corner of the display 41, there is illustrated an orientation for the left side of the head. As noted herein, there can be provided two implanted Neurostimulator Systems, one for the right and one for the left side of the head. Thus, the user can select between both sides for display.

The illustrated image includes an image of the left side of the head that is divided into three sections. There is a first frontal section including the supraorbital nerve region, a medial section including the parietal nerve region and a distal section that includes the occipital nerves. As noted herein, the programmer 40 is operable to interfaced through a headset or external charging/communication circuit (not shown) with one or more implanted neurostimulator systems. Thus, there is provided a display area 43 in the LCD display for depicting the recharge level of the Programmer 40 and a display area 42 for depicting the charge level of each neurostimulator system, one for the left and one for the right, if two neurostimulator systems are implanted and being monitored. For each section of the displayed head image, the frontal, the medial and the distal, there is illustrated a percentage of value illustrating the percentage level of stimulation that is being applied. There are provided left and right toggle buttons 45 that allow a particular section to be selected and increase/decreased buttons 46 to increase and decrease the level of stimulation. A confirm button 47 is provided for actually entering information after selection thereof. A lot button is disposed on the upper side, as illustrated in FIG. 8B.

Figure 9:
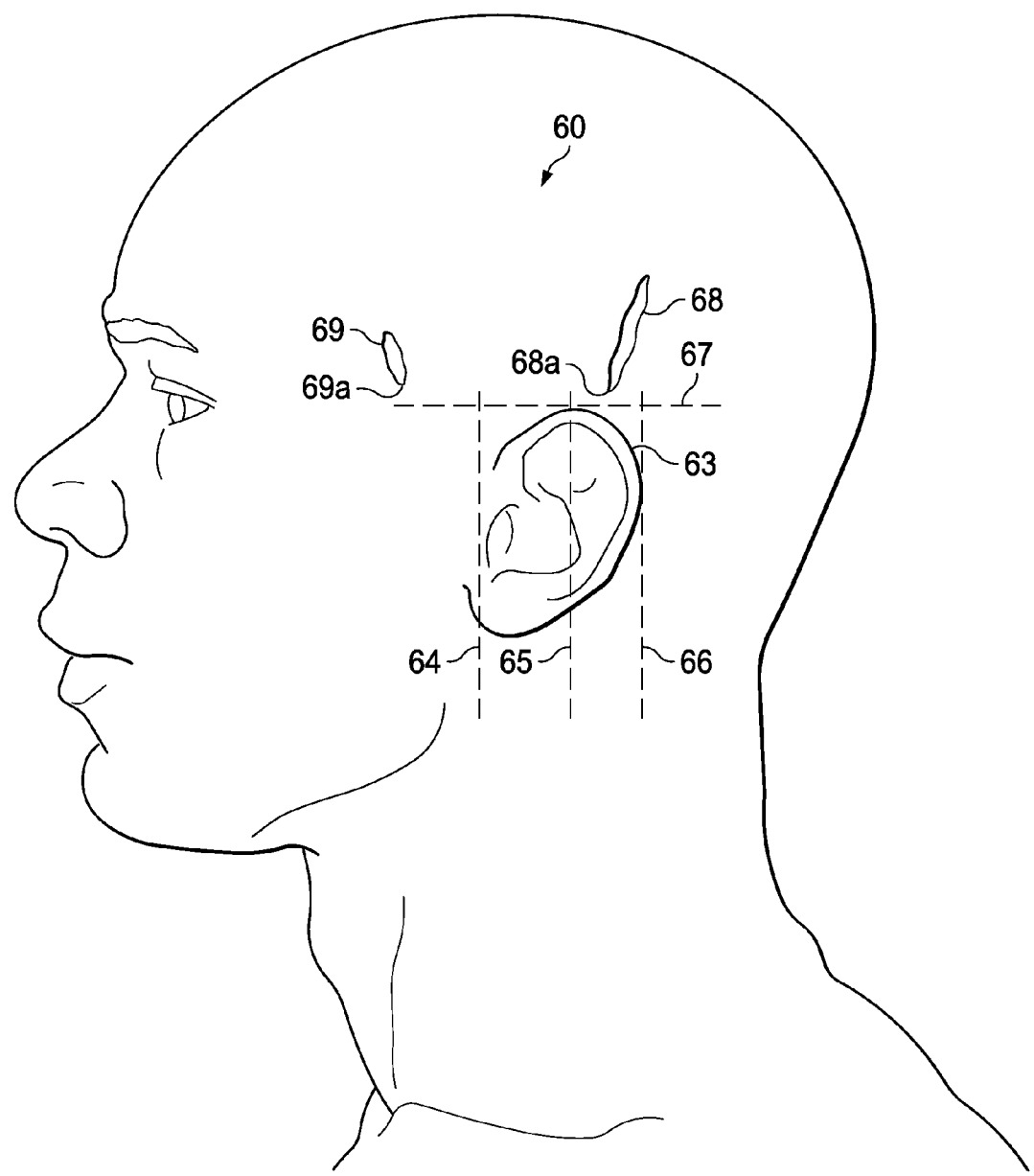
FIG. 9 depicts a side view of a head and initial interventional step in the procedure.

FIG. 9 depicts a side view of a head and the initial interventional step in the procedure for implanting the Neurostimulator system. Prominent here are depictions of the two incisions required for placement of the neurostimulator: 1) a supraauricular incision where the IPG will be implanted and from which the FPL and OL are tunneled subcutaneously to their final subcutaneous positions over the Fronto-Parietal and Occipital regions respectively, and 2) a Temple Subcutaneous Incision per which the FPL is initially passed from the IPG in the Supra-auricular Incision, whereupon it is again passed subcutaneously to its final subcutaneous position over the nerves of the supraorbital region. Four drawn lines are also depicted which are used as references to define relative positions for incisions and passing the leads. What is illustrated is the parietal region of head 60 wherein lines are drawn about the pinna. A horizontal supra-pinna line is disposed above the apex 63 of the pinna, a vertical pre-pinna line 64 is drawn to the frontal side of the pinna, a vertical mid-pinna line 65 is drawn down the medial section of the pinna, a vertical post-pinna line 66 is drawn at the back of the pinna and a horizontal supra-pinna line 67 is drawn above the pinna. In this embodiment, the supra-auricular subcutaneous incision 68 is disposed above the line 68 inbetween the two lines 65 and 66. The lower point 68a of the incision 68 is disposed almost exactly between the two lines 65 and 66 and extends upward at an angle distal to the pinna. A Temple subcutaneous incision 69 is disposed forward of the line 64 with a lower point 69a of the incision being disposed at approximately the level of the line 67 forward of the line 64 and extending an angle upward and frontal to the point 69a.

Figure 10:
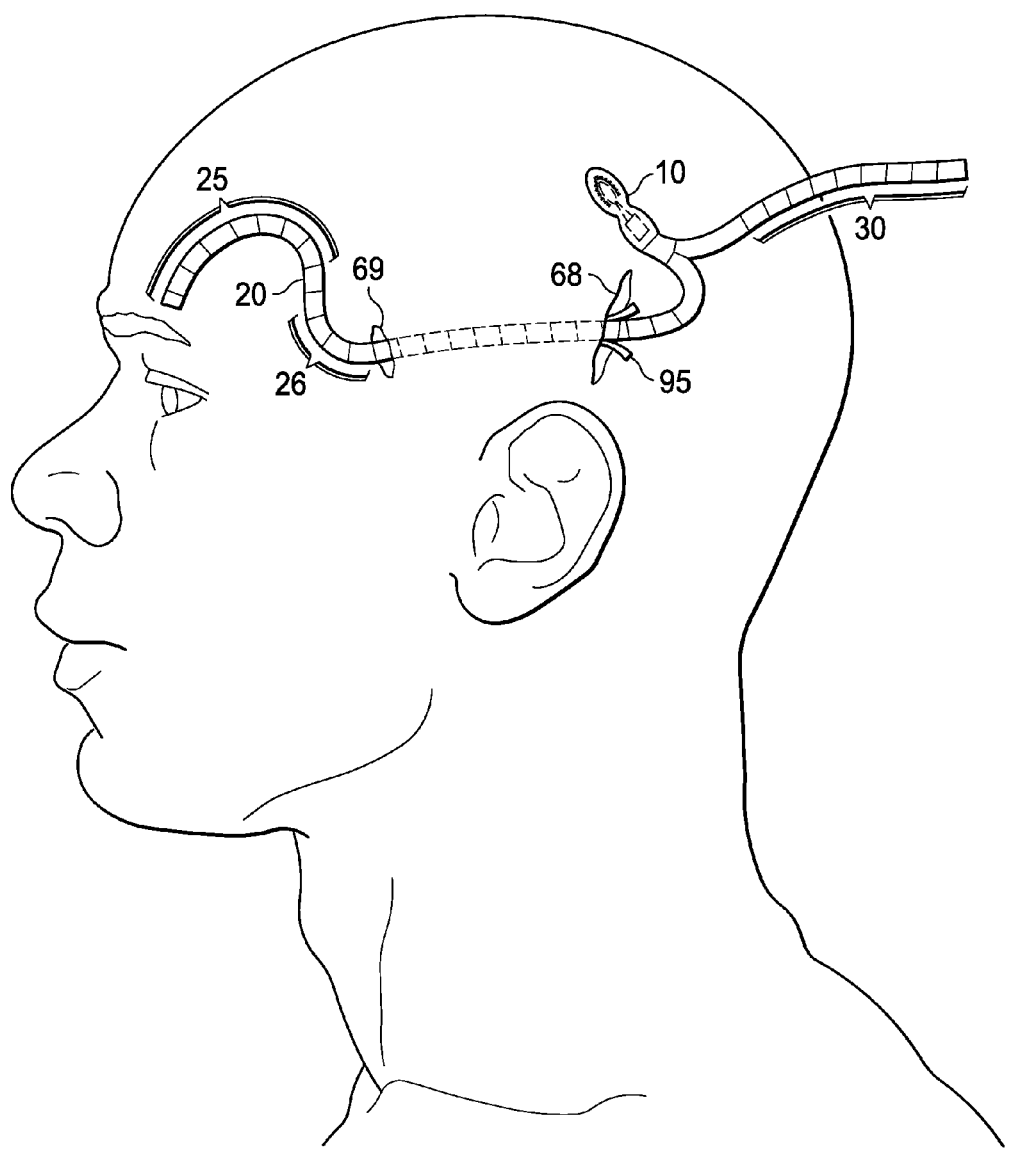
FIG. 10 depicts a side view of the head and the next step of the procedure following that depicted in FIG. 9.

FIG. 10 depicts a side view of the head and the next step of the procedure following that depicted and described in FIG. 9. The same incisions are depicted as referenced in FIG. 9; the Supra-auricular Incision 68 and Temple Incision 69. A traditional tubular Peel-Away Introducer 95 is depicted as having been passed subcutaneously from the Supra-auricular Incision to the Temple Incision. This introducer 95 provides a lumen through which to pass in the lead 20 after insertion thereof. The introducer 95 is comprised of two parts that are connected together with a serrated or breakable connection. Once the lead 20 is passed through the lumen of the introducer 95, it can be fully pulled through such that the frontal portion 25 is pulled all the way through the incision 69. The peel away introducer 95 can then be extracted by pulling each edge, there being two extensions for grabbing either's side of the introducer and peeling away, leaving the lead in place between incision 68 and 69. It can be seen that the IPG 10 and the assembly 30 are still not implanted, nor is the FEA 25. Thus, the FPL is passed through the Peel-Away Introducer, which is depicted in this drawing as beginning to separate in the act of being removed. Note that the OL and the Distal Segment of the FPL are still exterior to the skin.

Figure 11:
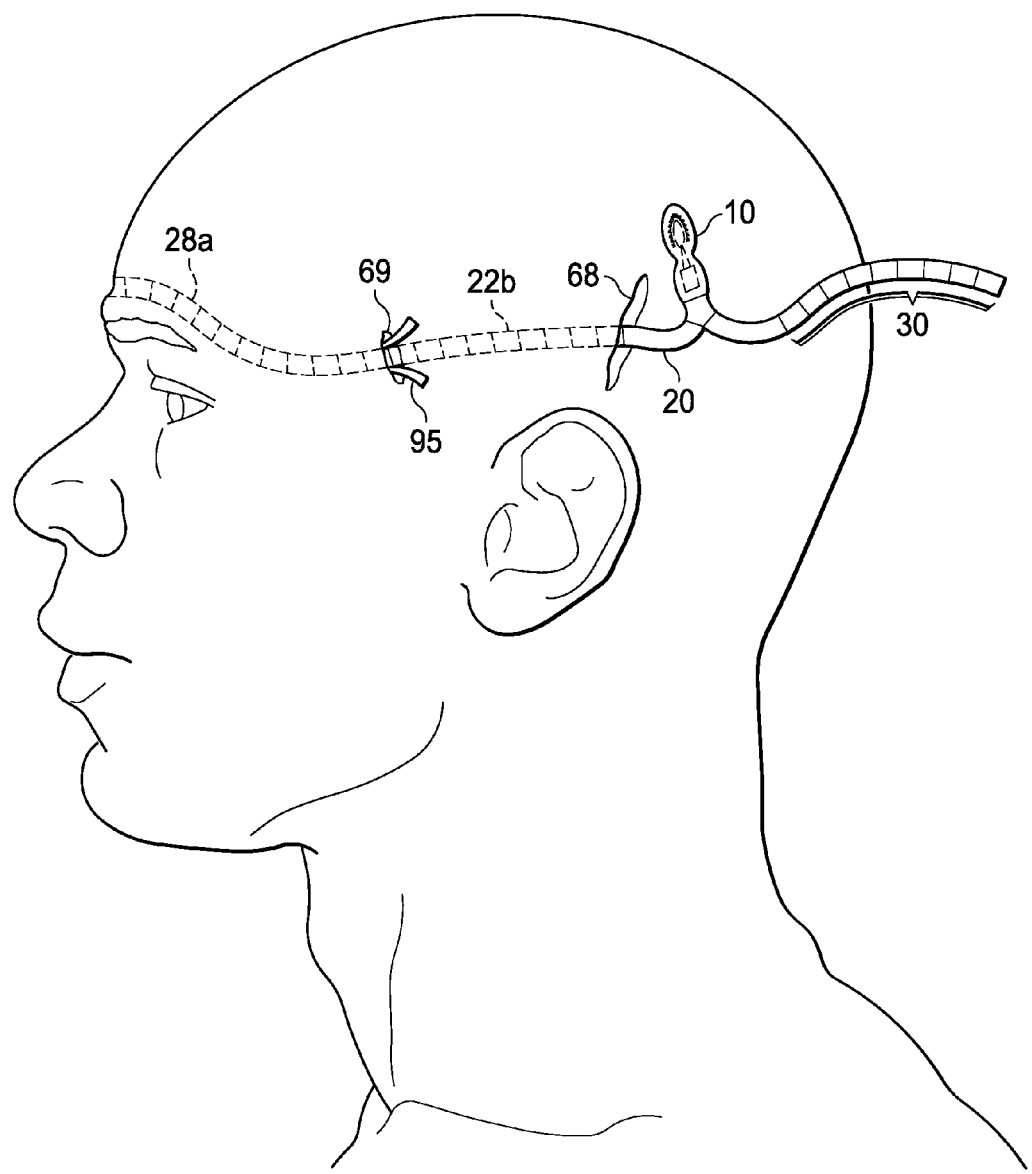
FIG. 11 depicts a side view of the head and the next step of the procedure following that depicted in FIG. 10.

FIG. 11 depicts a side view of the head and the next step of the procedure following that depicted and described with respect to FIG. 10. Prominent here is the depiction of a new Peel-Away Introducer as having been passed subcutaneously from the Temple Incision 69 to its final position proximate to the supraorbital nerve region where its distal tip approximates the midline, and the FEA is in the Subcutaneous Layer, which places it over the nerves of the Supraorbital Region. The Proximal Lead Segment of the FPL is depicted as having been positioned subcutaneously such that the PEA is positioned in the Subcutaneous Layer over the nerves of the associated Parietal Region. The IPG 10 and OL 30 are depicted as remaining exterior to the incision 68 at this point in the procedure.

Figure 12:
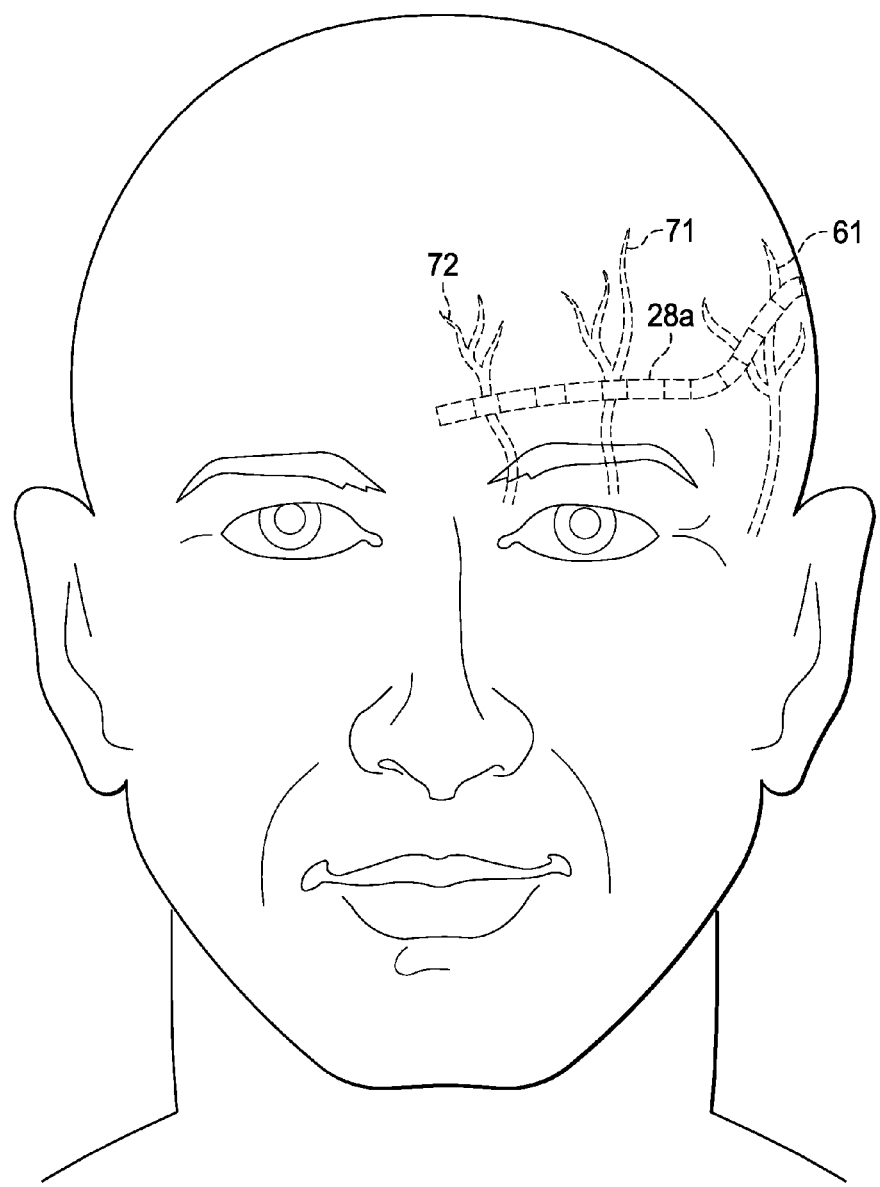
FIG. 12 depicts a frontal view of the FL as having been positioned subcutaneously as discussed in FIG. 11.

FIG. 12 depicts a frontal view of the FL as having been positioned subcutaneously as discussed in FIG. 11. The FL is depicted having its FEA in its subcutaneous position where it is crossing over and superficial to the nerves of the Frontal Region, including here the Supraorbital Nerve 71 and the Supratrochlear Nerve 72.

Figure 13A:
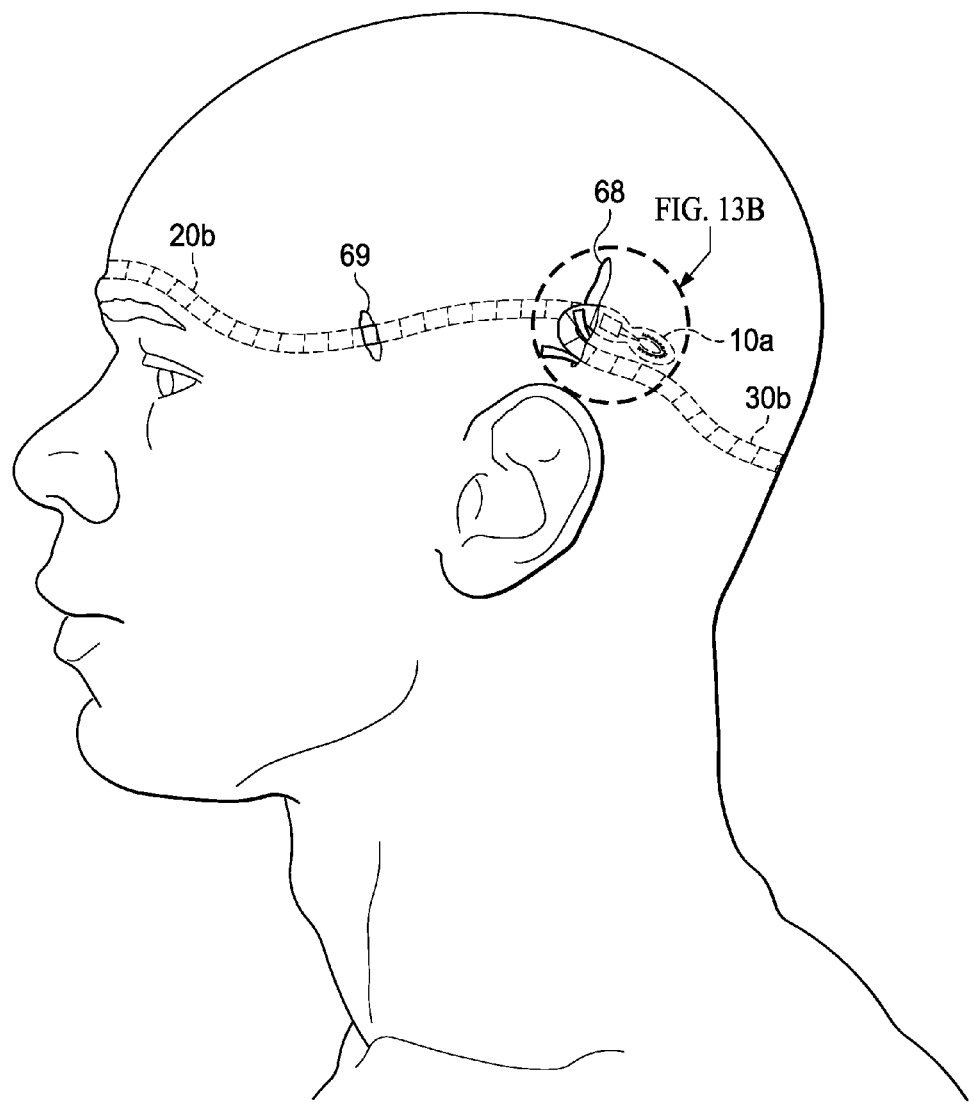
FIGS. 13A and 13B depict a side view of the next step in the procedure after the step depicted in FIGS. 11 and 12.
Figure 13B:
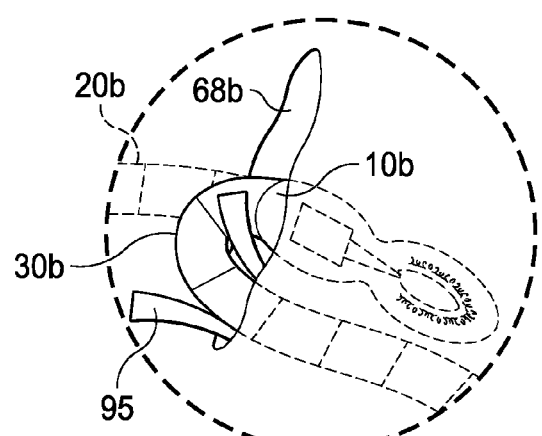

FIGS. 13A and 13B depict a side view of the next step in the procedure after the step depicted and described with respect to FIGS. 11 and 12. Prominent here are the IPG 10 and OL 30 which have been passed and positioned subcutaneously in the IPG pocket and over the nerves of the Occipital Region, respectively. The FPL 20b is depicted as having been passed subcutaneously as demonstrated in FIGS. 11 and 12. Also prominent is a blow-up view of the Supra-Auricular Incision 68 at this step in FIG. 13B, where the IPG 10a is pictured in its Subcutaneous Pocket and the most proximal segments of the FPL 20b and OL 30b are depicted as they enter the subcutaneous spaces in route to their final positions as depicted in the previous figures. Of note is the Peel-Away Introducer 95 over the OL 30b, which is depicted as just being separated as part of the procedure of removing it. The FPL 20b is depicted as having been passsed subcutaneously to its final position as depicted in the previous figures. The IPG 10a can either be inserted into the IPG subcutaneous pocket prior to insertion of the OL 30b into the introducer 95 or in the opposite sequence.

Figure 14:
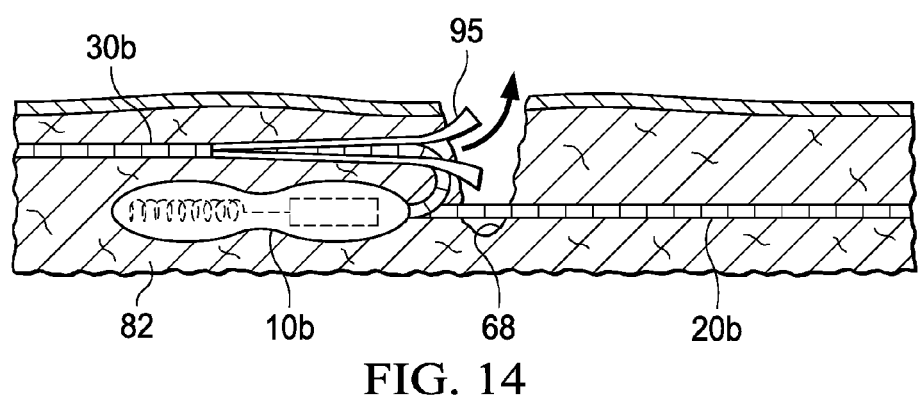
FIG. 14 depicts a cross section view of the skin at the Supra-auricular Incision at the stage of the procedure depicted in FIG. 13. Prominent here is the IPG in its Subcutaneous Pocket, as well as the initial proximal segments of the FL and the OL as they pass per the Subcutaneous Layer. The Peel-Away Introducer noted in FIG. 13 is also prominent.

FIG. 14 depicts a cross-section view of the skin at the Supra-auricular Incision 68 at the stage of the procedure depicted in FIG. 13. Prominent within the subcutaneous layer 82 is the IPG 10a in its Subcutaneous Pocket, as well as the initial proximal segments of the FPL 20b and the OL 30b as they pass per the Subcutaneous Layer. The Peel-Away Introducer 95 noted in FIG. 13 is also prominent. Once the peel away introducer 95 is removed, the Supra-auricular Incision 68 can be closed. At this point in time, the incision is closed prior to activating the IPG 10a. It could, of course, be activated prior to closing of the incision but at this stage, the Neurostimulator System is completely implanted and all the leads positioned.

Figure 15:
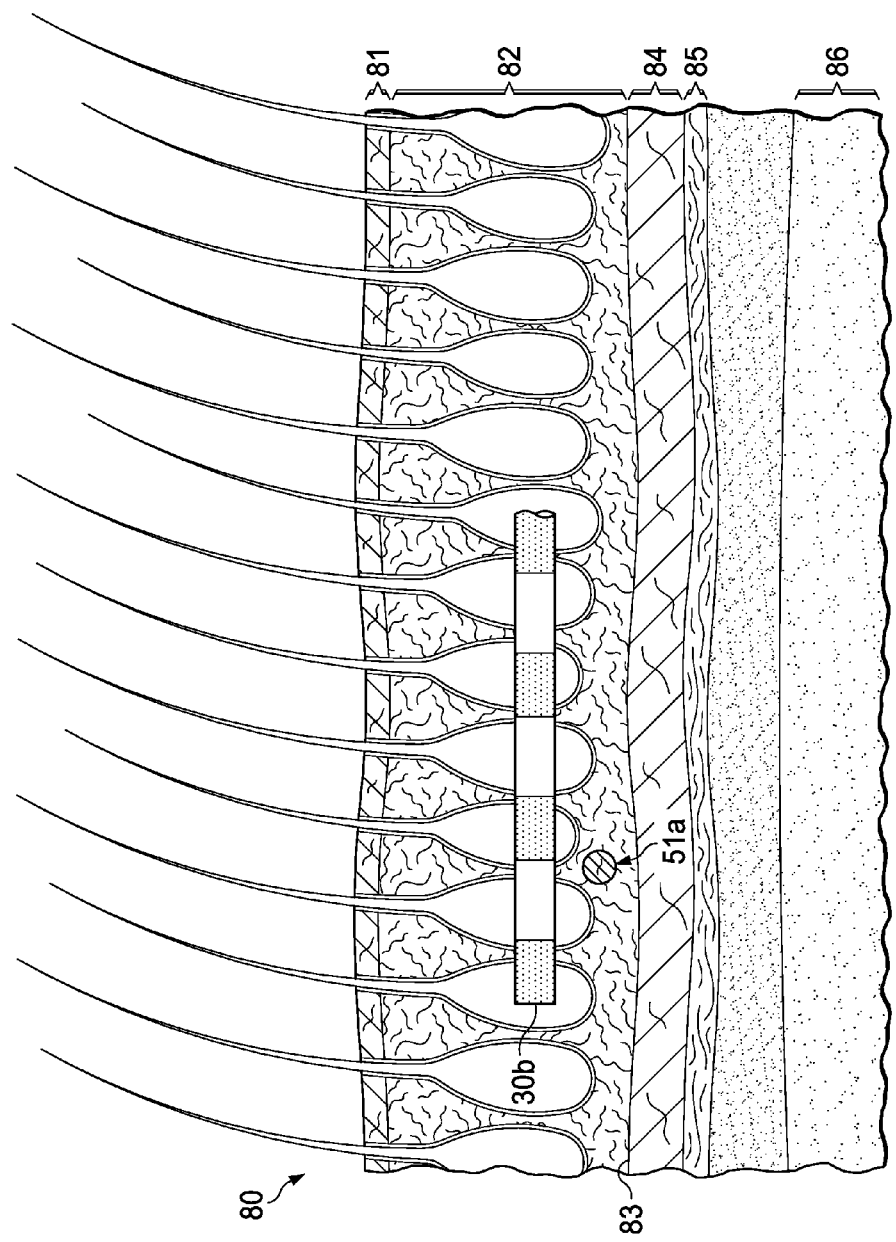
FIG. 15 depicts a cross section view of the skin at the point where the Active Electrode Array of the OL has been positioned over (superficial to) the Subcutaneous Layer.

FIG. 15 depicts a cross-section view of the skin at the point where the Active Electrode Array of the OL 30*b* has been positioned over (superficial to) the Subcutaneous Layer, which lies between the superficial Dermis and the underlying Fascia. The Muscle Layer, Aponeurosis and the Boney Skull are represented as sequentially deeper layers beneath the Fascia. The regions illustrated are the Boney skull 86 over which lies a thin layer 85, the Aponeurosis, over which lies a muscle layer 84, over which lies the subcutaneous tissue layer 82 and finally the dermis 81. Illustrated within the subcutaneous tissue layer 82 is a cross-section of the greater occipital nerve 51*a*. The OL 30*b* is disposed within the subcutaneous tissue layer 82 above the greater occipital nerve 51*a*.

Figure 16:
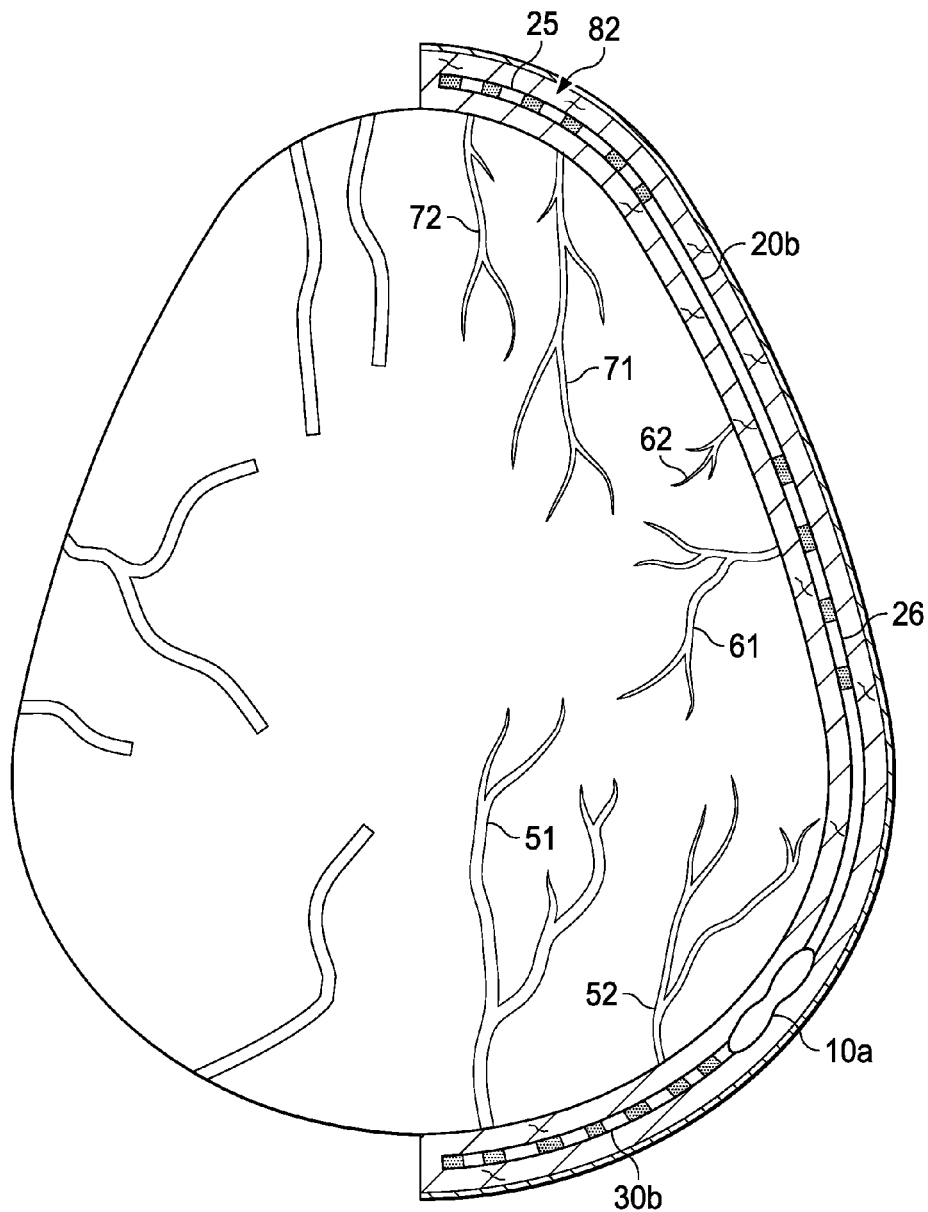
FIG. 16 depicts a view of the head from the top after the full neurostimulator system has been implanted.

FIG. 16 depicts a view of the head from the top after the full neurostimulator system has been implanted. Prominent here are the full system, including the IPG 10*b*, FPL 20*b* and OL 30*b*, which all lie within the Subcutaneous Layer. Also prominent are the FEA 25, the PEA 26, the OEA 35 in their final positions over (superficial to) the corresponding nerves in the Frontal Region, the Parietal Region, and the Occipital Region respectively.

Figure 17:
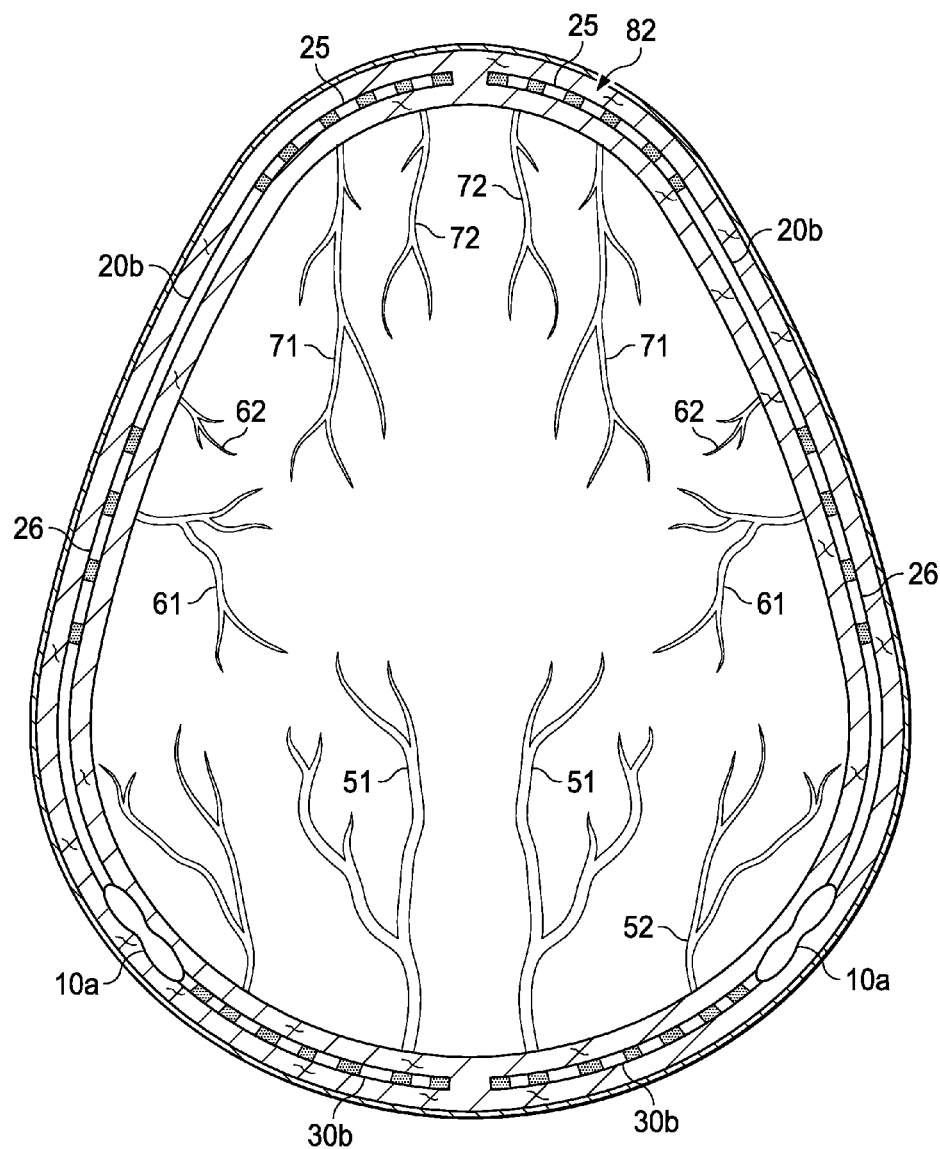
FIG. 17 depicts two implanted IPGs with leads to cover both sides of the head.

FIG. 17 depicts two implanted IPGs with leads to cover both sides of the head. The two structures are numbered identically with respect to their compliments, and they are implanted identically, one on the left side of the head and one on the right side of the head, as described above.

Figure 18:
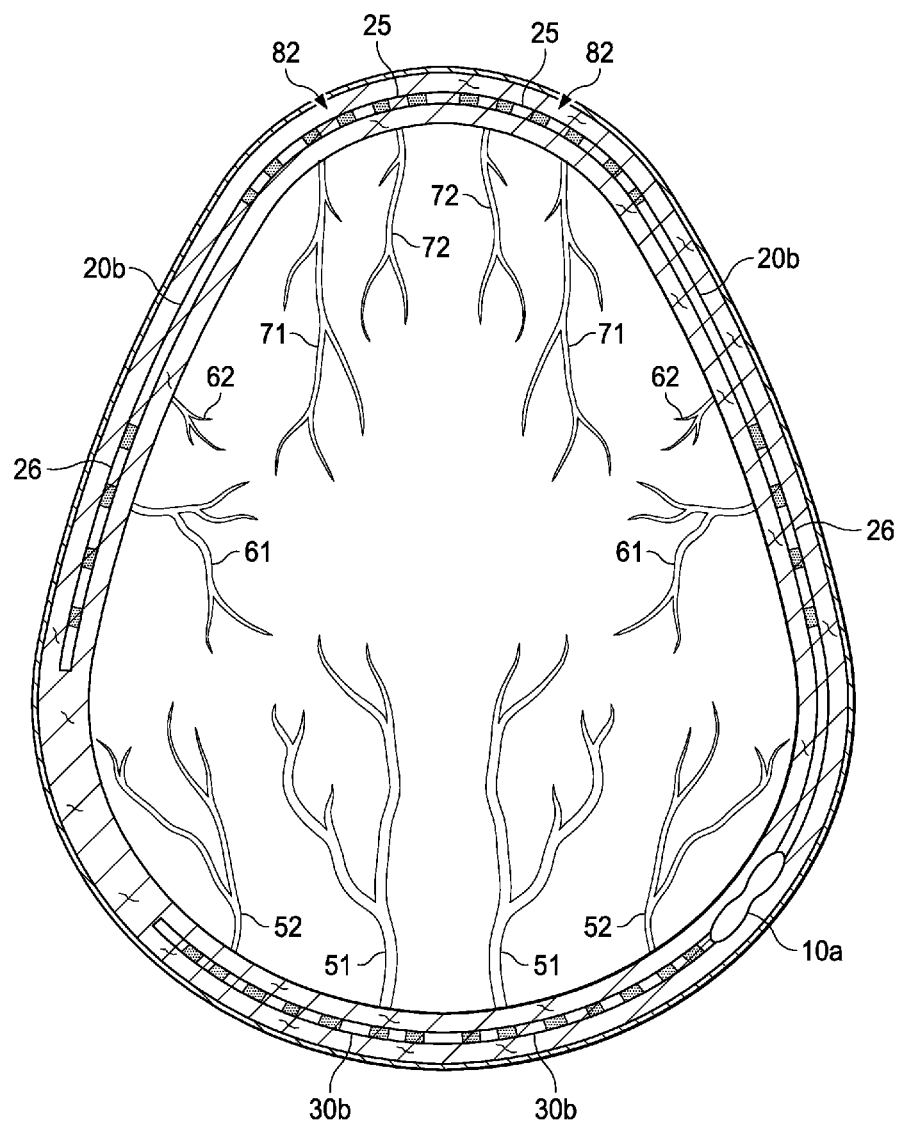
FIG. 18 depicts one implanted IPG with leads to cover both sides of the head.

FIG. 18 depicts one implanted IPG with leads to cover both sides of the head. In this embodiment, the FPL 20*b* extends from the IPG 10*a* on one side of the head around the parietal region on that side of the head, the two frontal regions and on the parietal region on the opposite side of the head such that there are two PEAs 26, two FEAs 25 and two OEAs 35. This, of course, requires an incision to be made on the temporal region on the side of the head on which the IPG 10 is implanted and a frontal incision made to allow the FPA 20 to be routed to and in a frontal incision and then to a temporal incision on the upside the head and finally to the parietal region on the upside the head. This is the same with respect to the occipital lead 30 that must be routed through possibly an additional acetylene incision of the back of the head. All that is required is the ability to route particular leads to the respective regions proximate the nerves associated therewith. This will allow a single IPG 10 to cover two frontal regions, two parietal regions and two occipital regions.

Thus, the procedure to implant, in summary, is to first provide a neurostimulator system that has a unibody construction comprised of an IPG integrated with the leads as opposed to a separate system wherein the leads are implanted first, positioned, activated and then connected to the IPG. Then the IPG implanted into an associated pocket. With the unibody construction of the disclosed neurostimulator system, this requires each of the multiple leads to first be positioned proximate to a desired nerve region through one or more incisions through the subcutaneous layer. This typically involves a single initial incision that is associated with the subcutaneous pocket for the IPG, wherein the leads are first inserted through the incision to the particular nerve region subcutaneously and then the IPG disposed within the pocket subcutaneously. However, the IPG is not secured to an underlying structure, such as bone or fascia. The reason for this is that the IPG is, first, very lightweight, and second, disposed in an area of the skull that is subject to very little movement, thus minimizing the possibility of any migration of the leads.

M. Alternate Embodiments

There are multiple alternate embodiments that preserve the features of the neurostimulation system disclosed herein, which include an externally rechargeable and programmable IPG, sized and configured for implantation in the head, and from which fronto-parietal and occipital leads, along with their respect surface metal electrode arrays, extend to cover multiple regions of the head. In various embodiments, the spacing and dimensions of the electrode array(s) for each specific array may be constant, or the electrode arrays may be specifically designed with respect to electrode type, dimensions, and layout for improving the therapeutic effectiveness for the specific cranial region it is to be associated with. The multiple alternate embodiments also include a subcutaneously positioned unibody neurostimulator device that contains an IPG and two leads, one with a single electrode array and the other with two electrode arrays.

Thus, the disclosure comprises extended electrode array designs (two or more regions by a single lead), and/or multiple arrays and optimized intra-array electrode dispositions. The disclosure also comprises lead configurations, which include the capability of a modular lead design that provides for ports on either the standard FPL and OLs. In another embodiment, the IPG may receive additional separate leads, if and as necessary either at the time of initial implant or in the future.

Further, the lead lengths, along with the specific technical makeup and dimensions of the individual surface metal electrodes and electrode arrays, may be varied to include more or less than three unilateral regions of the head (occipital, parietal, and frontal) contemplated by the first embodiment. For example, a single IPG may energize and control multiple additional leads of varying lengths that ultimately could be disposed over virtually every region of the head and face bilaterally, to thus cover multiple and disparate regions, with each of these leads and arrays of electrodes associated therewith designed for a particular cranial region. Further, each of these leads can have one or more disparate arrays associated therewith so as to accommodate more than a single cranial region, this single multi-array lead allowing a single incision to accommodate these multiple regions.

At least two electrodes may be included per region (and thus per array), and while the first embodiment calls for a total of 24 electrodes disposed over three arrays covering three different regions of the head the occipital, parietal and frontal regions—there is no absolute limit to the maxim (or minimum) number of electrodes. Similarly, while the first embodiment calls for three electrode arrays, the disclosure contemplates two, or even one array (so long as the arrays covers at least two regions). There is also no limiting maximum for the number of arrays. Also, there may be multiple variations of design within each separate array, including for example, variations in the number, dimensions, shape, and metal composition of the individual electrodes, as well as the distance and constancy of distance between electrodes, within each array. Further, each array may have the same or completely different designs.

While the neurostimulation system has been described for subcutaneous implantation as a peripheral neurostimulator in the head and for head pain, it is capable of being implanted and used as a peripheral nerve stimulator over other regions of the head and face than described above and also over other peripheral nerves in the body.

In another embodiment the IPG may be positioned subcutaneously over virtually any other point of the head that can accept the unit.

In another embodiment the leads may be passed such that their respective electrode arrays over positioned subcutaneously over other painful regions of the face, head and neck.

In another embodiment the leads may be passed by measures other than a standard Peel-Away Introducer. For example they may be passed per the previous retrograde positioning of a standard, metal tubular introducer, which is then removed over the lead once it has been positioned.

While a common embodiment includes the implantation of two neurostimulator systems (one on each side), other embodiments may include only system or may include more than two systems. These would depend upon the nature, location and extension of a patient's pain report.

While the neurostimulation system has been described for implantation as a peripheral neurostimulator in the head and for head pain, it is capable of being implanted and used as a peripheral nerve stimulator over other regions of the head and face than described above and also over other peripheral nerves in the body.

N. Operation

When functioning; that is when the internal circuit of lead internal wires is connected to an IPG; the SMEs of the various arrays are programmed to function as anodes and cathodes. The ASIC 13 then drives with a generated electrical pulse wave then passes from the ASIC of the IPG to the associated internal lead wire, and ultimately to its associated terminal surface metal electrode. The current then passes a short distance from the subcutaneous tissue, within which the neurostimulator system is implanted, to a contiguous, or nearby, electrode, whereby it passes back up the lead to its associated proximal metal contact, and then back to the IPG and the ASIC 13 to complete the circuit. The generated pulse waves pass through the subcutaneous tissue between two terminal electrodes that stimulates the sensory nerves of the area. As noted hereinabove, the configuration for the ASIC 13 can define certain of the SMEs as anodes and certain of the SMEs as cathodes. When active, the IPG may be programmed to produce continuous series of pulse waves of specified frequency, amplitude, and pulse width. It is this series of pulse waves actively stimulating a patient's locally associated nerves that underpins the therapeutic effect of the implanted unit. The electrical pulse wave then passes from a connected proximal surface metal contact, along the associated internal lead wire, and ultimately to its associated terminal surface metal contact.

With respect to FIGS. 5, 6 and 7. The neurostimulator system is subcutaneously implanted on the left side of the hemicranium over the respective nerve regions. The main body of the IPG 10 is disposed proximate to and rearward of the parietal bone just above the ear. A small incision (shown below) is made into which the FPL 20 is inserted and routed forward to the frontal bone passing over the auriculotemporal nerve 61 and the supraorbital supra orbital nerve 71. The OL 30 is routed through the incision backwards to the occipital nerve. Then the IPG 10 is inserted through the incision and then the incision closed. Thus, with a single incision, the entire neurostimulator system can be disposed in a subcutaneous region of the cranium, the regions selected such that a minimal amount of movement will occur with everyday activity of an individual. The selection of the region in which the main body is implanted is selected based upon a region that will result in minimal migration of the IPG 10 (noting again that it is not secured to bone), be very unobtrusive to the individual and allow easy access to the frontal and a possible regions of the cranium. There is no need to secure the main IPG 10 to the bone or to even provide any stylet securing it to the fascia.

It is to be understood that the implementations disclosed herein are not limited to the particular systems or processes described which might, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "an accumulator" includes a combination of two or more accumulators; and, reference to "a valve" includes different types and/or combinations of valves. Reference to "a compressor" may include a combination of two or more compressors. As another example, "coupling" includes direct and/or indirect coupling of members.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

Figure 19:
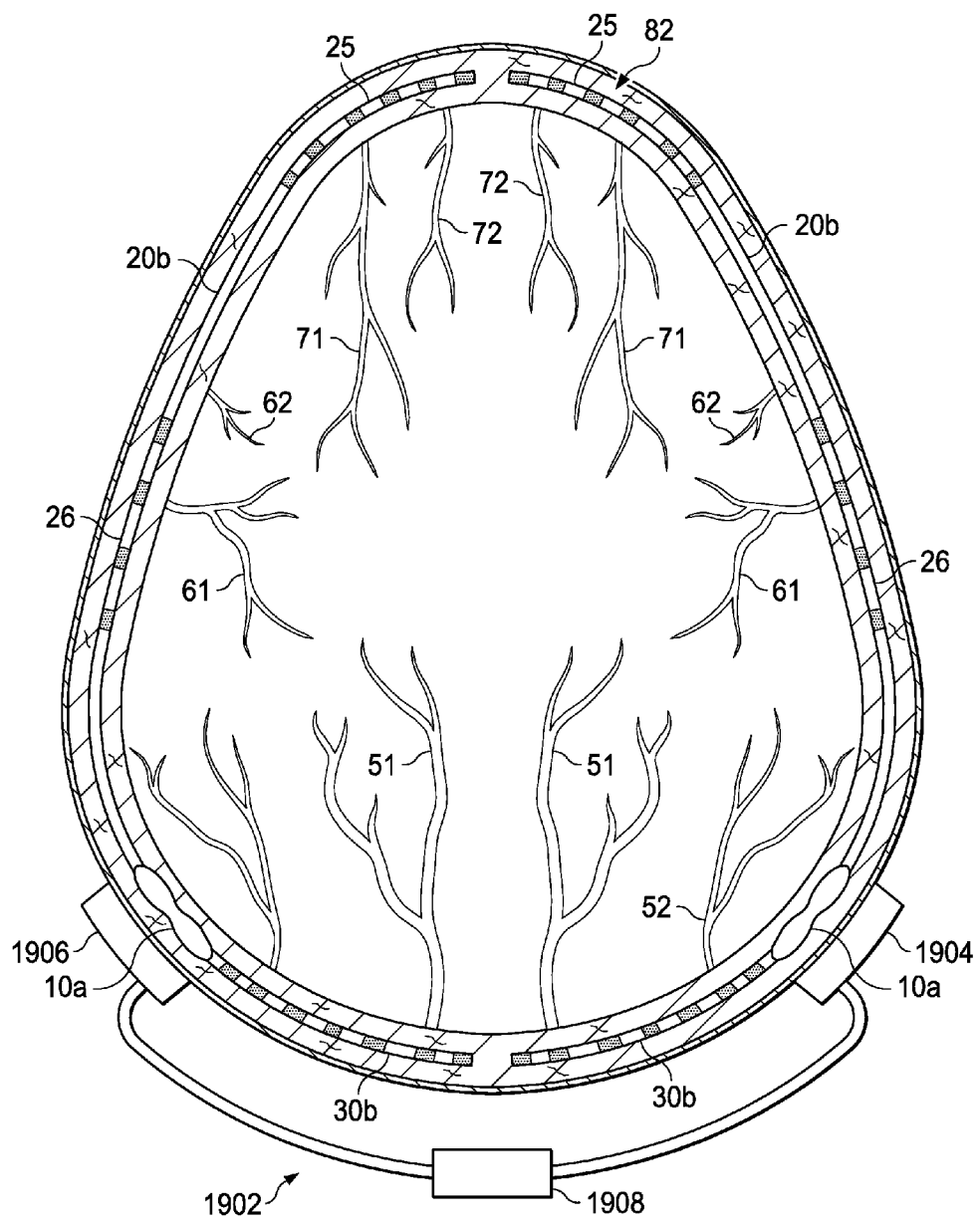
FIG. 19 illustrates the embodiment of FIG. 17 with a charging/communication headset disposed about the cranium.

Referring now to FIG. 19, there is illustrated a headset 1902 disposed about the cranium for interfacing with the two implants 10a of FIG. 17. The headset 1902 includes right and left coupling coil enclosures 1904 and 1906, respectively that contain coils coupled to the respective coils in the implants 10a. The coil enclosures 1904 and 1906 interface with a main charger/processor body 1908 which contains processor circuitry and batteries for both charging the internal battery in the implants 10a and also communicating with the implants 10a. Thus, in operation, when a patient desires to charge their implants 10a, all that is necessary is to place the headset 1902 about the cranium with the coil enclosures 1904 and 1906 in close proximity to the respective implants 10a. This will automatically effect charging. For communication, there is provided some internal communication required for charging but also, an external interface can be provided to the user via the handheld unit described in FIGS. 8A and 8B.

Figure 20:
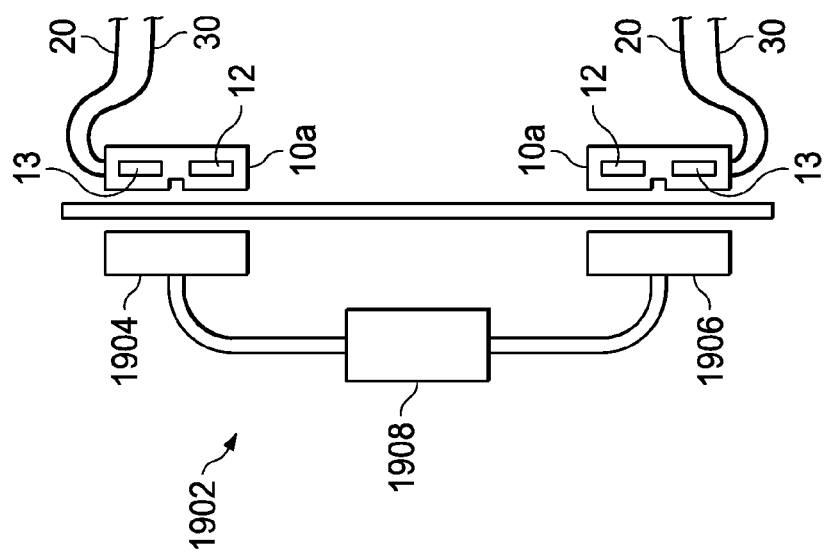
FIG. 20 illustrates a diagrammatic view of the headset interfaced with the implants.

Referring now to FIG. 20, there is illustrated a diagrammatic view of the interface of the headset 1902 with the implants 10a. Each of the implants 10a is interfaced with the leads 20 and 30 and includes the processor 13 and the battery 12. Also, although not illustrated, the coil 11 is disposed therein. It should be understood that the processor 13 can be any type of instruction based processing device or state machine and even an ASIC that is capable of executing a sequence of events that results in some pattern of stimulating signals to be transmitted to the electrodes and also facilitates charging/powering and communication.

Figure 21:
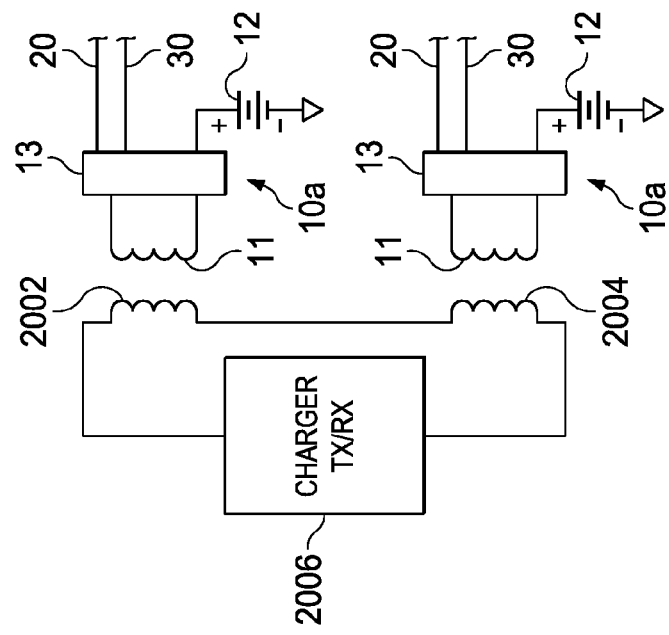
FIG. 21 illustrates a schematic view of the implants and headset.

Referring now to FIG. 21, there is illustrated a schematic view of the overall headset and implants. The headset 1902 is comprised of two coupling coils 2002 and 2004, each operable to couple with the respective coil 11 of the respective implants 10a. There is coupling of both charging power and communication, this communication being bidirectional. The two series coils 2002 and 2004 are controlled by a charger and TX/RX circuit 2006. This circuit 2006 is operable to generate sufficient energy at a resonant frequency of the coil to couple across the skin to the coil 11, which is then used to charge the respective battery 12. The processor 13 is operable to facilitate the charging and communication operations and also the driving operations for driving current to the associated leads 20 and 30.

Figure 22A:
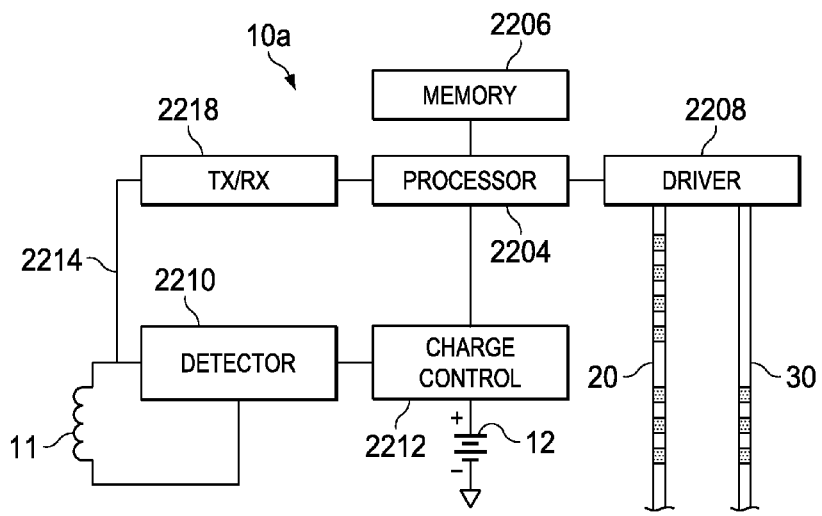
FIGS. 22A-B illustrate block diagrams of the headset/charger system.
Figure 22B:
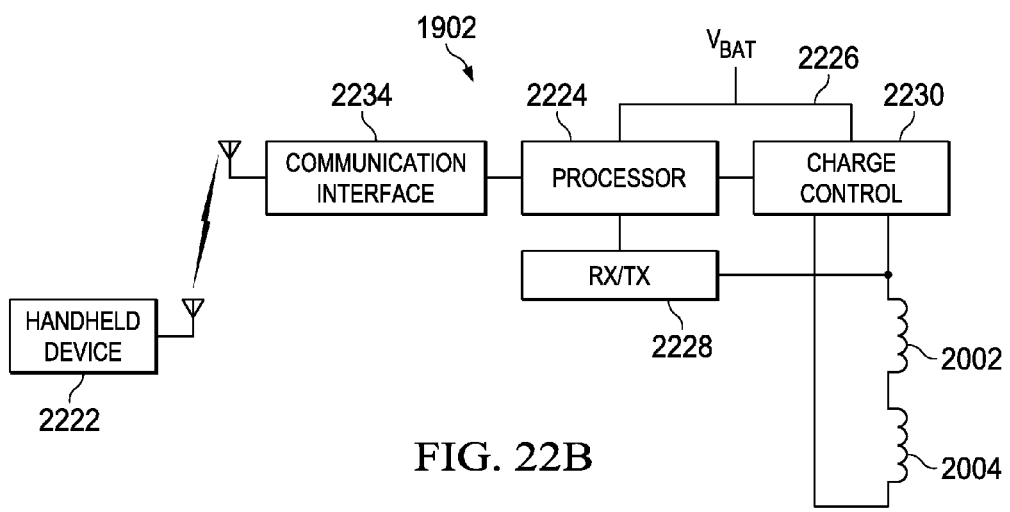

Referring now to FIGS. 22A and 22B, there are illustrated block diagrams for the operation of the overall system. With reference specifically to FIG. 22A, there is illustrated a block diagram for implantation 10a, wherein a microprocessor 2204 is contained at the heart of the overall operation. This is interfaced with a memory for storing instructions programs and also with a driver 2208 for driving leads 20 and 30. The coil 11 is interfaced with a detector 2210 that is operable to detect energy across the coil 11 and convert it to a DC value for input to a charge control circuit 2212, which is controlled by the microprocessor 2204, and discharges the battery 12, the battery 12 providing power to the entire implant 10a. Additionally, the coil 11 has an interface through a connection 2214 to a TX/RX circuit 2218 which is operable to detect received data that is interposed onto the resonant frequency of the energy transfer such that information can be received. Also, transmitted information can be the same type of signal, which is transmitted onto the coil 11. This TX/RX signal can be transferred across the coil 11 to the respective coil 2002 or 2004 between the headset 1902 and the implants 10a such that the charger and TX/RX circuit 2006 in the headset 1902 can communicate with implant 10a. It should be understood that the microprocessor 2204 can be any type of instruction based processing device or state machine and even an ASIC that is capable of executing a sequence of events that results in some charging/powering of the implant and communication therewith.

Referring now to FIG. 22B, there is illustrated a block diagram of headset 1902 interfaced with the handheld device, as indicated by block 2222. The headset includes a processor 2224 which is interfaced with a battery through a signal supply line 2226. The processor 2224 is interfaced with a charge control circuit 2230 that drives the two coils 2002 and 2004. The processor 2224 also controls a RX/TX circuit 2228 that is operable to communicate with the implants 10a by inserting a data signal onto the resonant frequency of the coils 2002 and 2004 with an AC signal that can be coupled across the skin to the coils 11 or both transmit and receive operations. The processor 2224 also interfaces with a communication interface 2234 that is operable to wirelessly communicate with the handheld device 2222. This navigation interface can use any type of communication interface required such as Bluetooth, Bluetooth low energy, Zigbee or any type of communication protocol. This merely allows a user to interface with processor 2224 on the headset 1902 for the purpose of interfacing with the implant. This allows a surgeon, for example, after implanting the devices, to test the devices without having to actually access the leads themselves to plug into a separate controller. Thus, the implants are implanted and the incisions closed up before any attempt is made to determine the efficacy of the overall operation of the implants in any particular patient.

Figure 23:
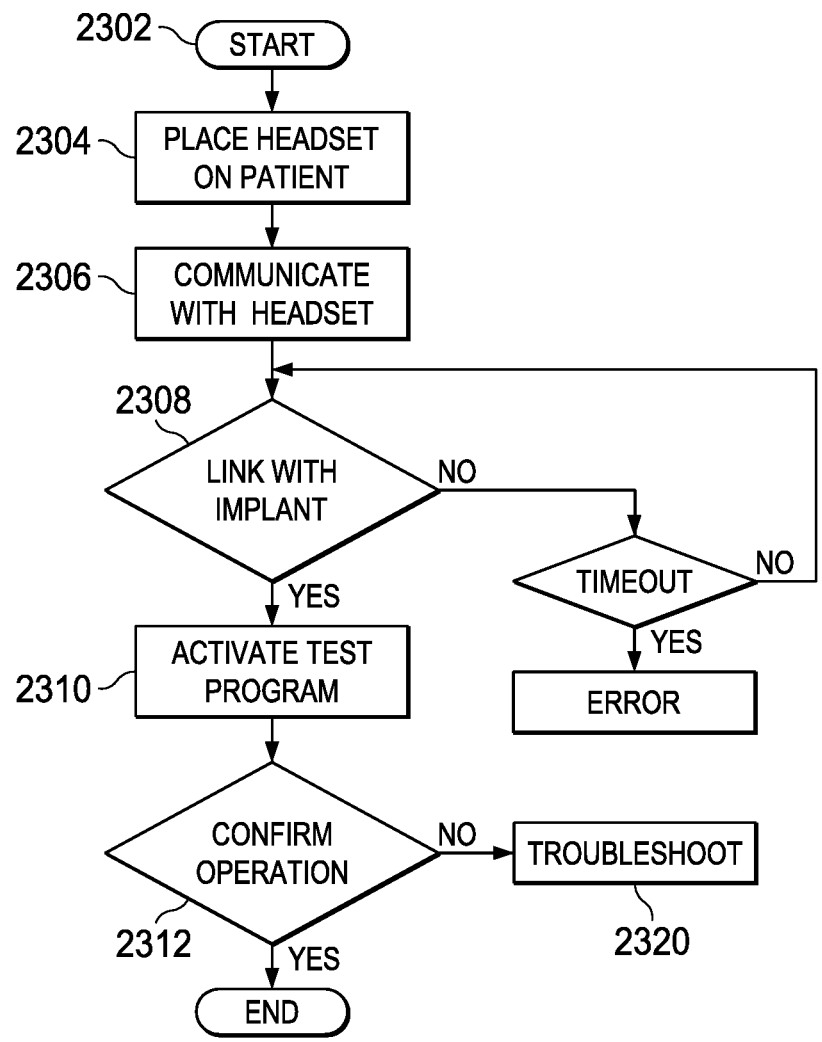
FIG. 23 is a flowchart for the activation process to test the implant(s) after implantation.

Referring now to FIG. 23, there is illustrated a flowchart depicting the overall operation of activating the implant after surgery. This is initiated at a Start block 2302 and then proceeds to a block 2304 wherein the headset is placed onto the patient after surgery. Thereafter, communication with the headset is effected through a handheld unit, for example, as indicated by block 2306. The program then flows to a decision block 2308 to determine if a link with the implant can be made. Initially, the implants have batteries with a finite charge such that they are able to communicate with the headset 1902. However, if not, the implants will charge. Once sufficient charge has been provided to the implants, a link will be made with the implant and the program will flow to a block 2310 to activate a test program. However, until the link is made, a return loop will be made back to the input of the decision block 2308 until a timeout has occurred and then an error will be indicated. Once the test program has been activated, the program flows to a decision block 2312 to determine if a confirmation has been received that the operation has occurred. This typically is feedback to the patient and in that the therapeutic relief expected by the patient has been achieved to some extent. If no confirmation has been received, the program will flow to a block 2320 in order to troubleshoot the system. In general, what might happen is that different programs would have to be implemented in order to adjust the distribution of the driving signals across the electrodes associated with the various implanted leads.

Figure 24:
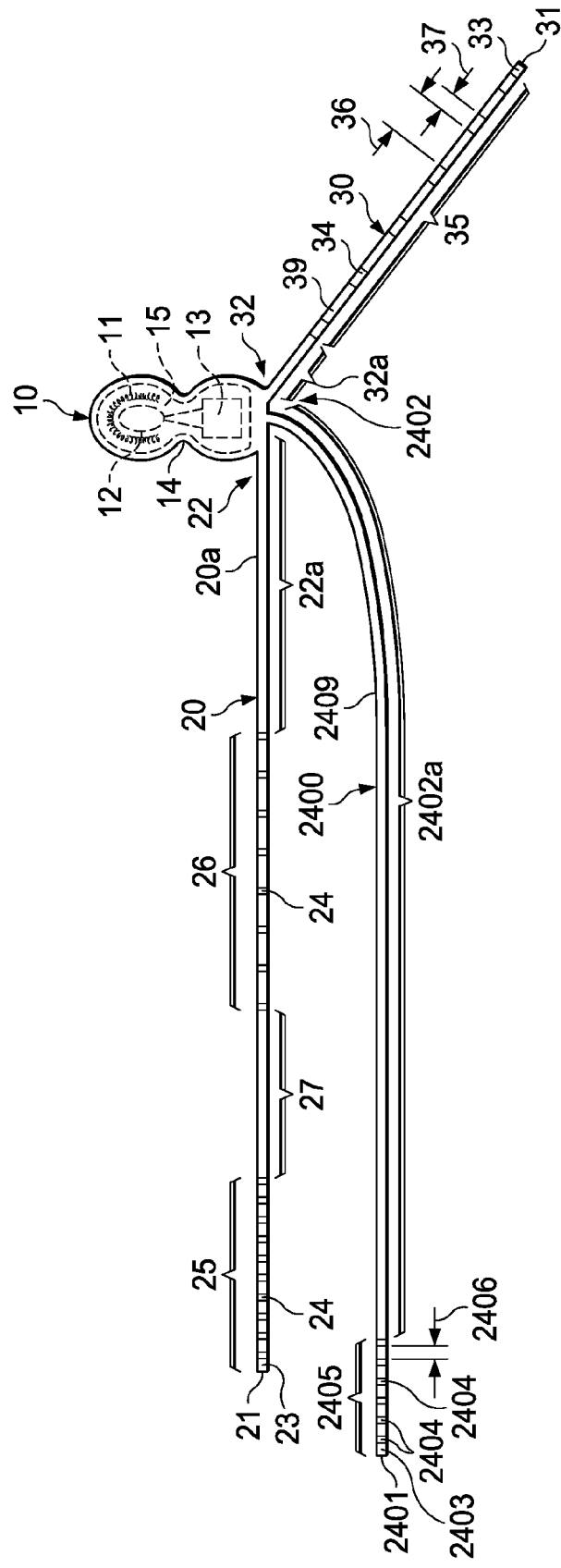
FIG. 24 illustrates a unibody neurostimulator system which includes an infraorbital lead.

Turning now to FIG. 24, there is illustrated another embodiment of a neurostimulator system which, in addition to the Fronto-Parietal Lead 20 and the Occipital Lead 30, includes a Infraorbital Lead (IL) 2400. The IL 2400 is similar to the OL 30. The IL 2400 is of adequate length to extend roughly to the region of the face just beside the nose between the eye and the bottom of the nose. IL 2400 is an internal part of the unibody construction and extends from the IPG 10. IL 2400 comprises a plastic member 2409 and a set of internal wires 2408 (described hereinbelow with respect to FIG. 25) that pass through the central cylinder of the lead to connect to a series of SMEs 2404 that are uniformly disposed along a portion of the length of the lead. The lead internal wires 2408 pass and connect in the same manner as described hereinabove for the SMEs 24 of the FEA 25 and the PEA 26 and the SMEs 34 of the OEA 35.

The plastic body member 2409 is an elongated, cylindrical, flexible member, which may be formed of a medical grade plastic polymer. It has a proximal end 2402 and a distal end 2401. Progressing along the lead from the proximal end 2402, these segments sequentially include a proximal lead segment 2402a, an infraorbital electrode array (IEA) 2405, and a distal non-stimulating tip 2403.

Staying with FIG. 24, the IEA 2405 consists of a plurality of surface metal electrodes (SME) 2404 uniformly disposed over a portion of the IL 2400. Lead internal wires 2408 connect to the SMEs 2404 in the same fashion as depicted for the FEA as shown in FIG. 2. As is the case with respect to the FEA 25, the PEA 26, and the OEA 35, the SMEs 2404 of the IL 2400 have an interelectrode spacing 2406 and design that is specific for stimulating the nerves in the infraorbital region. Also, the number of electrodes required for the array will be a function of the particular region, the infraorbital region, that is being treated. As will be described hereinbelow, each of these electrodes can be designated as an anode or a cathode and any combination can be designated to be energized in a set up procedure performed by a clinician. This provides a configuration that can be adapted to a particular patient at a particular placement of the IL 2405.

Figure 25:
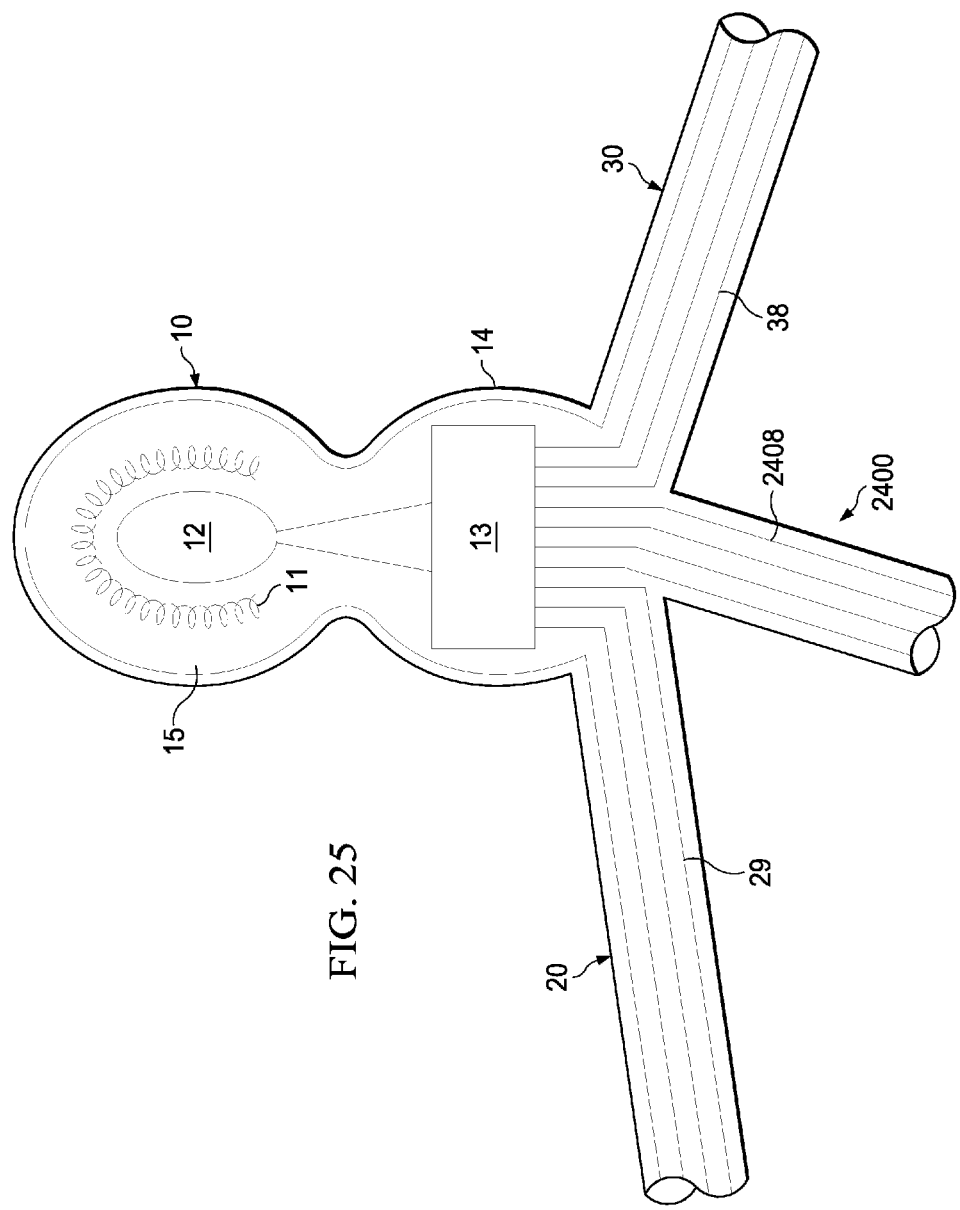
FIG. 25 illustrates the IPG of a neurostimulator system which includes an infraorbital lead.

Turning to FIG. 25, there is illustrated a cutaway view of the IPG 10. Visible are the FPL 20, the OL 30, and the IL 2400. Also visible within the IL 2400 are internal wires 2408 which run between the ASIC 13 and the SMEs 2404 on the IL 2400.

Figure 26:
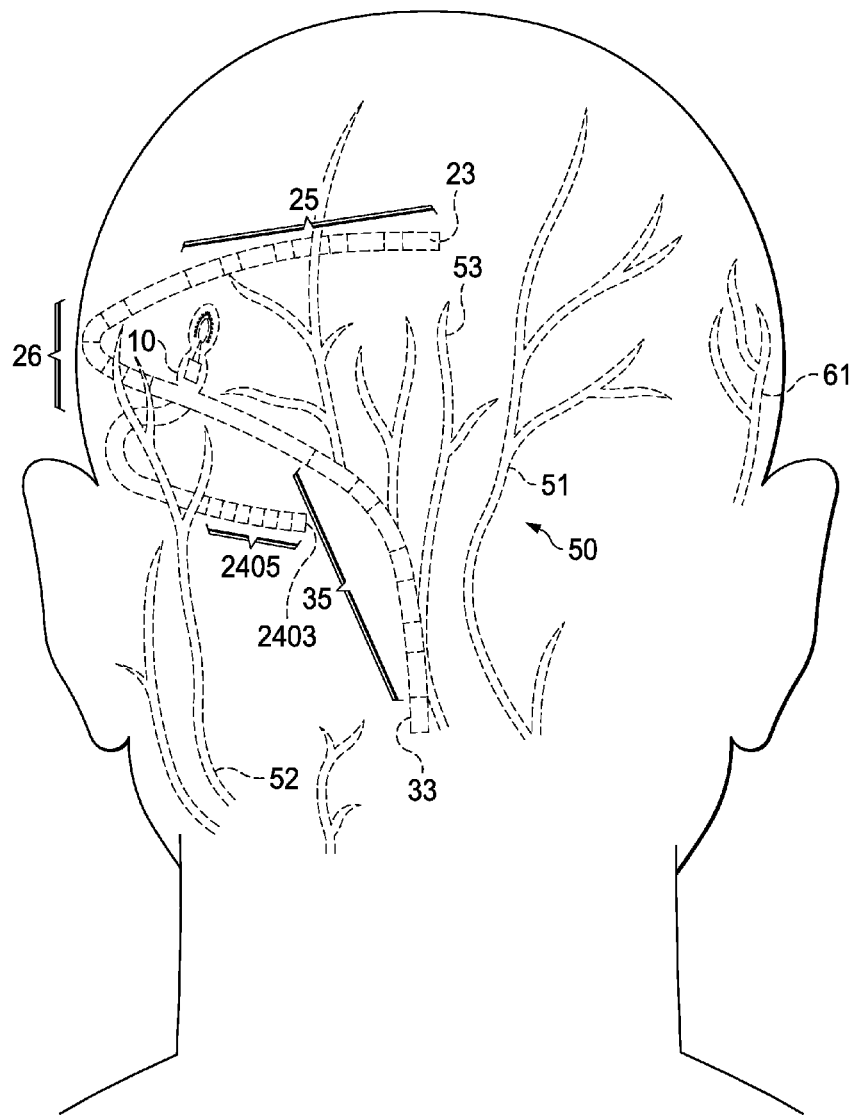
FIG. 26 illustrates the back of a head with with a neurostimulator system implanted which includes an occipital lead, a fronto-parietal lead, and an infraorbital lead.

Turning now to FIG. 26, there is illustrated a rear view of a head with an embodiment of the full head-mounted neurostimulator system in situ which includes the IL 2400. In addition to the PEA 26, the FEA 25, and the OEA 35 (as depicted in FIG. 5), there is also visible the IEA 2405.

Figure 27:
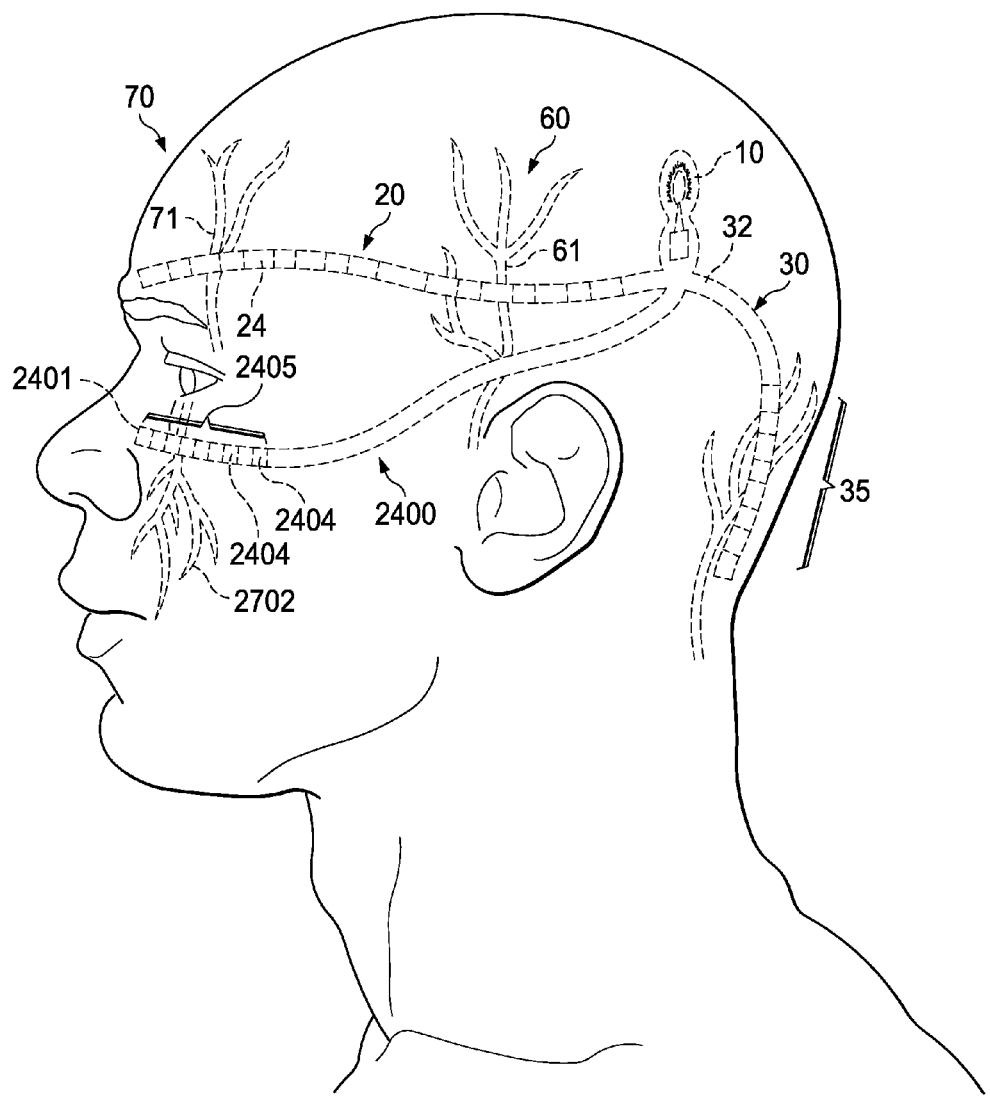
FIG. 27 illustrates the side of a head with a neurostimulator system implanted which includes an occipital lead, a fronto-parietal lead, and an infraorbital lead.

Turning now to FIG. 27, there is illustrated a side view of a head with an embodiment (the same embodiment depicted in FIG. 26) of the neurostimulator system in-situ. In addition to the FPL 20 and the OL 30, there is visible the IL 2400. Visible on the IL 2400 are the SMEs 2404 which comprise the IEA 2405. The IL is implanted under the skin of the patient and extends from the IPG 10, which is roughly above the ear, forward and down, such that the non-stimulating distal tip 2401 is under the eye and next to the nose. The IEA 2405 will pass through the infraorbital region and over the infraorbital nerve bundle 2702, which lies under the skin next to the nose and between the eye and mouth.

Figure 28:
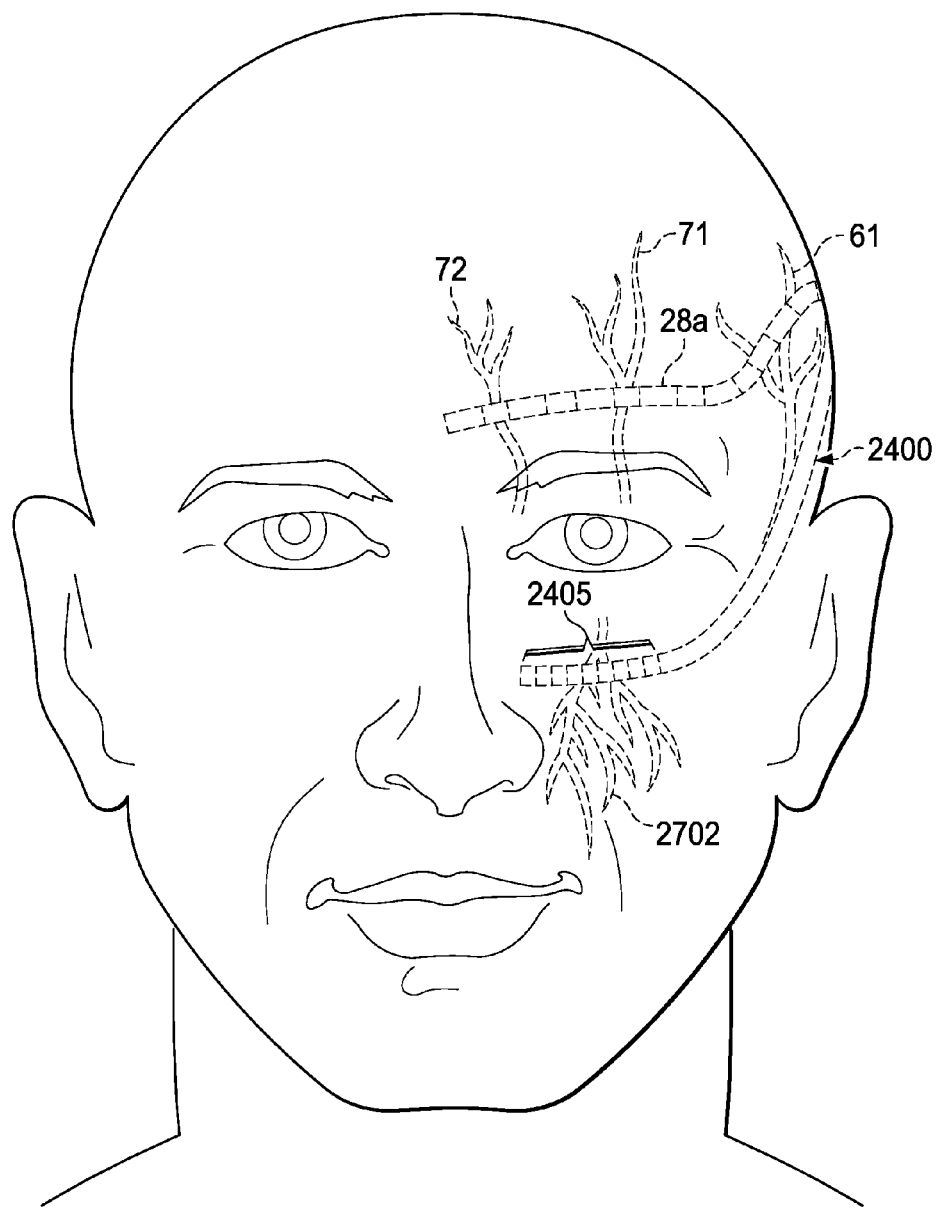
FIG. 28 illustrates the front of a head with a neurostimulator system implanted which includes an occipital lead, a fronto-parietal lead, and an infraorbital lead.

Turning now to FIG. 28, there is illustrated a front view of a head with an embodiment (the same as shown in FIGS. 26 and 27) of the neurostimulator system. The IL 2400 and the IEA 2405 are visible and positioned in the infraorbital region of the head. The IEA 2405 lies over the infraorbital nerve bundle 2702.

Figure 29:
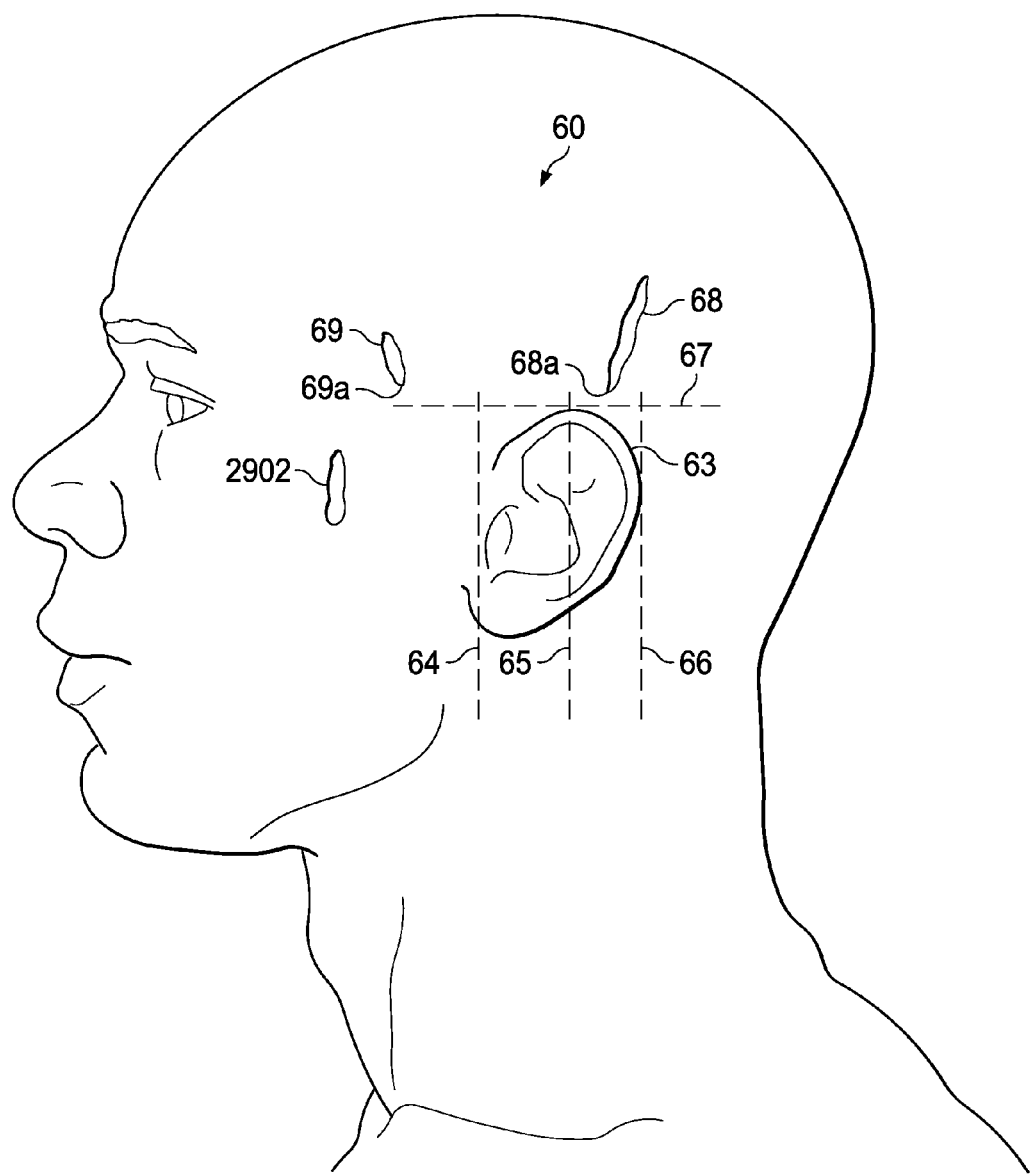
FIG. 29 illustrates the side of a head with incisions made for implanting a neurostimulation system which includes an occipital lead, a fronto-parietal lead, and an infraorbital lead.

Turning now to FIG. 29, there is illustrated a side view of a head and the initial interventional step in the procedure for implanting an embodiment of the neurostimulator system that includes an IL 2400. This step includes all of the incisions required for the FPL 20 and the OL 30, as depicted in FIG. 9 and described hereinabove with respect to FIG. 9. An additional incision 2902 is made forward of the ear, roughly midway between the ear and the nose and at a vertical point roughly just below the bottom of the eye proximate the zygomatic arch.

Figure 30:
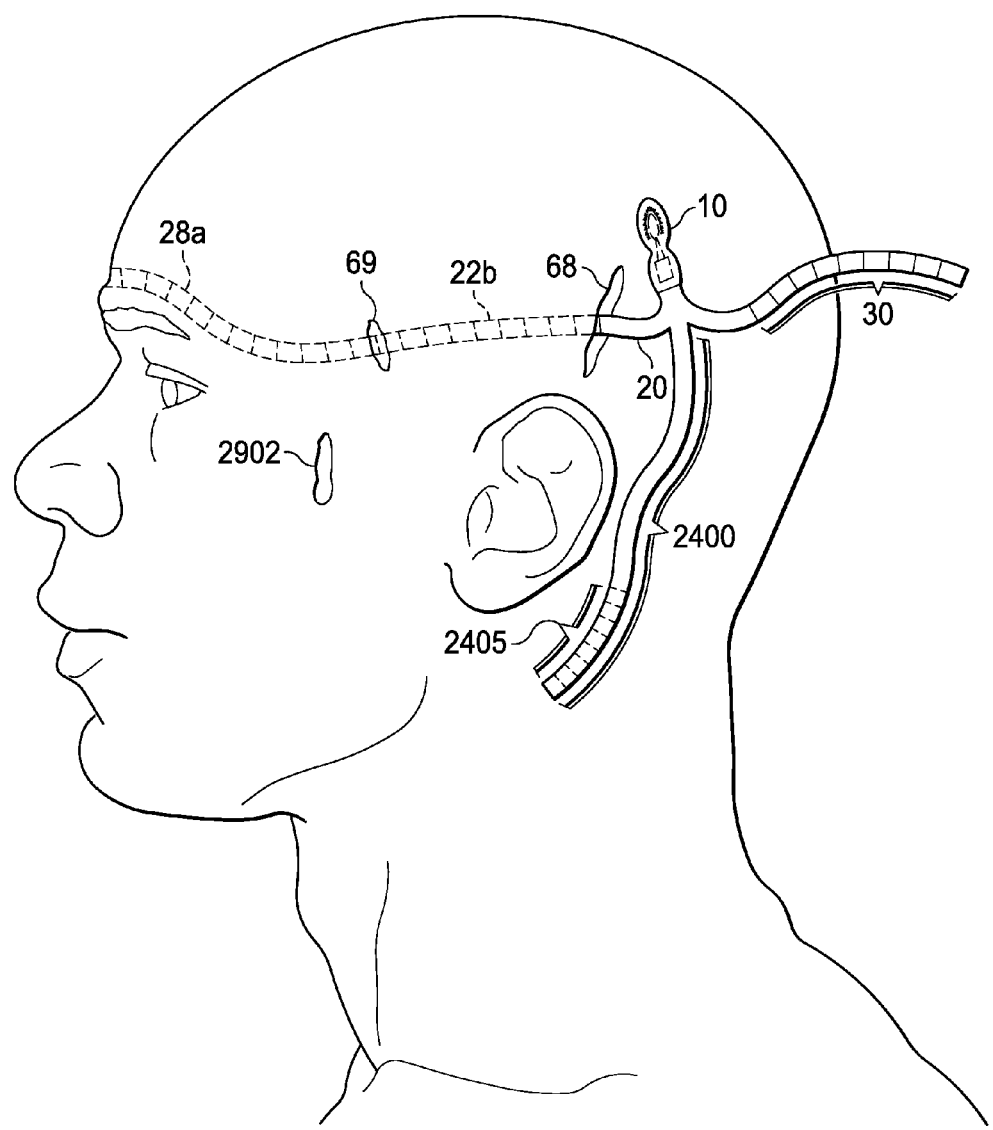
FIG. 30 illustrates the next step in implanting a neurostimulation system which includes an occipital lead, a fronto-parietal lead, and an infraorbital lead after the incisions are made and the fronto-parietal lead is implanted.

Turning now to FIG. 30, there is illustrated the step of the procedure following that depicted in FIG. 10 and described hereinabove with respect to FIG. 10. As explained earlier, embodiments which have an IL 2400, in addition to an FPL 20 and an OL 30, will have steps for implanting the neurostimulator system that are cumulative to the embodiments which only have a FPL 20 and an OL 30. Therefore, the step depicted in FIG. 30 begins with the FPL 20 already having been implanted and positioned in the appropriate location as described hereinabove with respect to FIG. 10. The OL 30 and the IL 2400 are positioned outside the patient's skin, ready to be placed in their appropriate subcutaneous positions.

Figure 31:
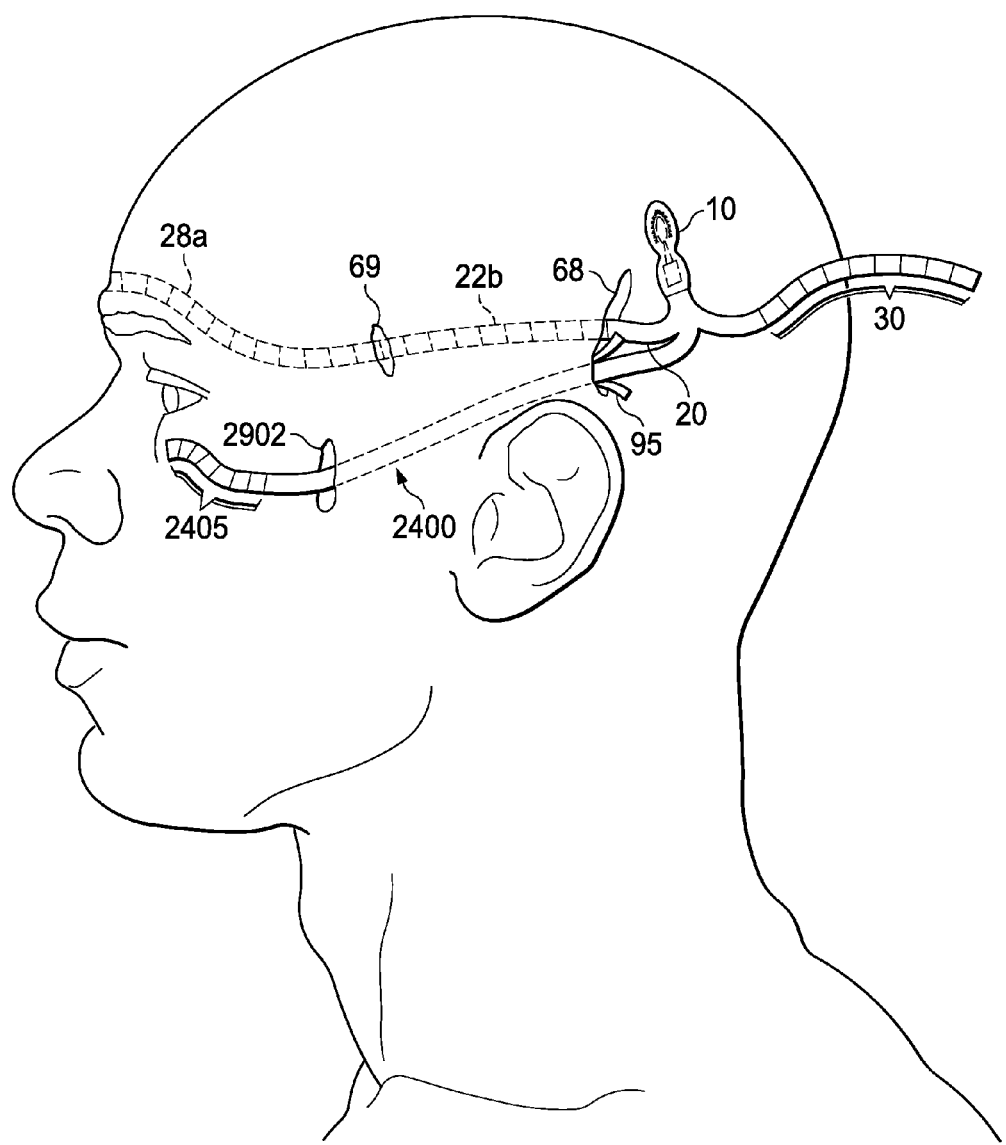
FIG. 31 illustrates the step in implanting a neurostimulation system which includes an occipital lead, a fronto-parietal lead, and an infraorbital lead of inserting the infraorbital lead into the first incision.

Turning now to FIG. 31, there is illustrated a side view of the head and the next step, following the step described with respect to FIG. 30, of implanting the IL 2400. This step is analogous to the step described hereinabove with respect to FIG. 10 for the FPL 20. In this step, a peel-away introducer 95 is passed through the incision 68 to the incision 2902. The IL 2400 is then passed subcutaneously through the introducer 95 from the incision 68 to the incision 2902. Once the IL 2400 is passed through the lumen of the introducer 95, it is pulled through such that the distal portion of the IL 2400 with the IEA 2405 is pulled all the way through the incision 2902. The peel-away introducer 95 can then be extracted in the way described with respect to FIG. 10.

Figure 32:
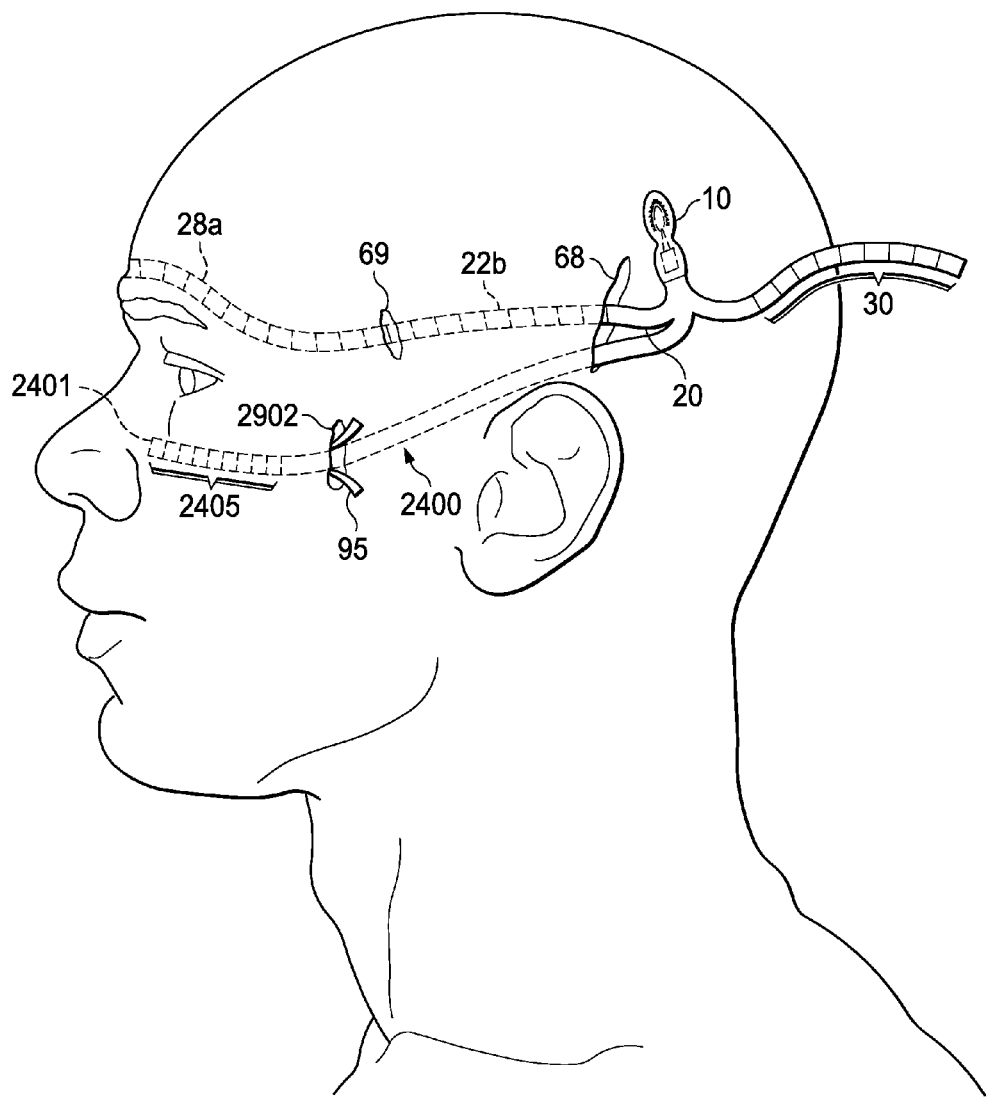
FIG. 32 illustrates the step in implanting a neurostimulation system which includes an occipital lead, a fronto-parietal lead, and an infraorbital lead of inserting the infraorbital lead into a second incision.

Turning next to FIG. 32, there is illustrated a side view of a head and the next step, following the step described with respect to FIG. 31, of implanting the IL 2400 in embodiments which include the IL 2400. Another peel-away introducer 95 is passed subcutaneously from incision 2902 to the final position of the IL 2400 proximate to the infraorbital region. The distal portion of the IL 2400 (which, in the step described with respect to FIG. 31, was pulled out of the incision 2902) is placed back in the incision 2902 in the introducer 95 and positioned such that the non-stimulating distal end 2401 will be disposed over the infraorbital nerve bundle under the eye and next to the nose. The IL 2400 having now been placed in its final position, the peel-away introducer 95 is then removed from the incision 2902. The OL 30 and the IPG 10 are then subcutaneously implanted in the same way as for embodiments that do not include an IL 2400, such as those that only include an FPL 20 and an OL 30, that is, in the same way as is described hereinabove with respect to FIGS. 12-15.

Figure 33:
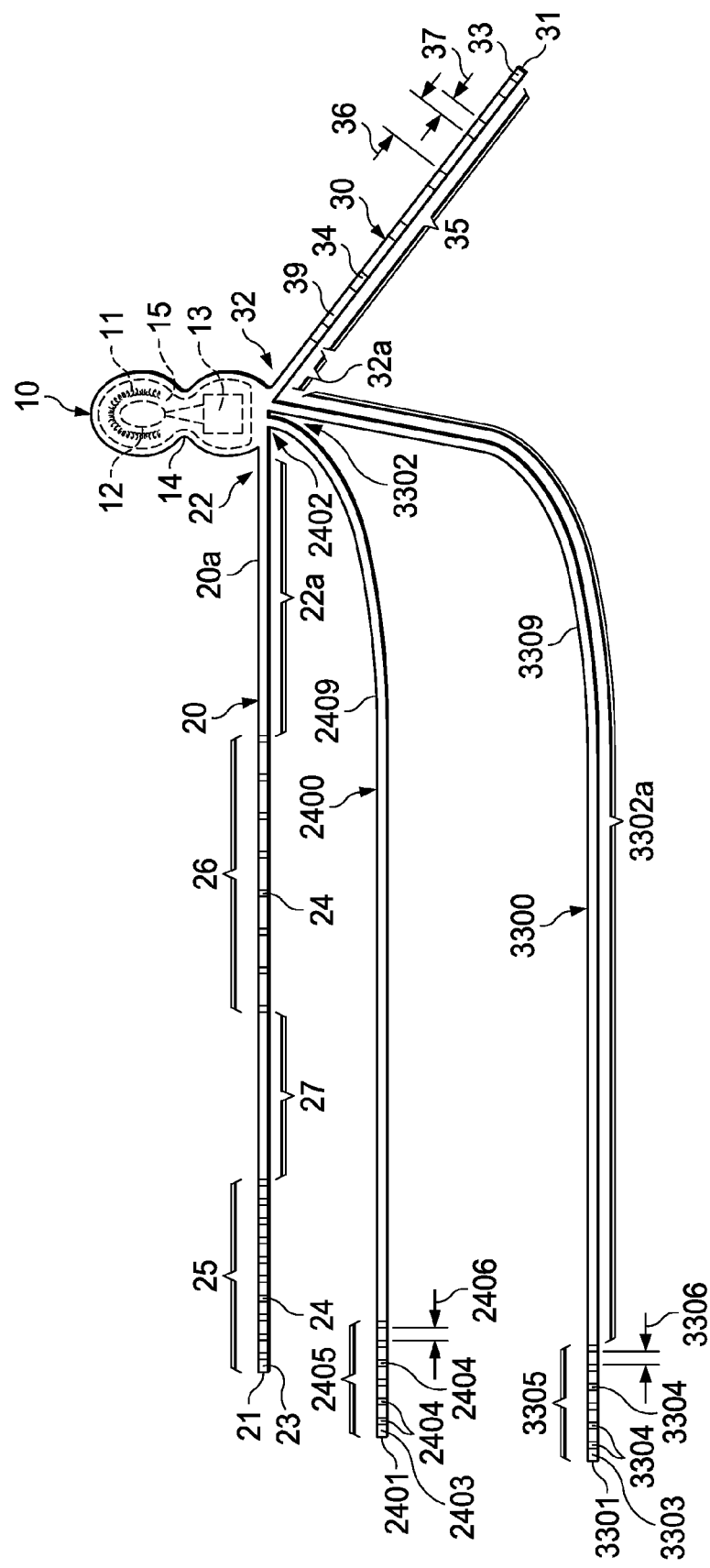
FIG. 33 illustrates a neurostimulator system which includes an occipital lead, a fronto-parietal lead, an infraorbital lead, and a mandibular lead.

Turning now to FIG. 33, there is illustrated another embodiment of a neurostimulator system which, in addition to the FPL 20, the OL 30, and the IL 2400, includes a mandibular lead (ML) 3300. The ML 3300 is similar to the OL 30 and the IL 2400. The ML 3300 is of adequate length to extend roughly to the chin below the mouth at a point near the center of the mouth. The ML 3300 is an internal part of the unibody construction and extends from the IPG 10. ML 3300 comprises a plastic member 3309 and a set of internal wires 3308 (described hereinbelow with respect to FIG. 34) that pass through the central cylinder of the lead to connect to a series of SMEs 3304 that are uniformly disposed along a portion of the length of the lead 3300. The lead internal wires 3308 pass and connect in the same manner as described hereinabove for the SMEs 24 of the FEA 25 and PEA 26, the SMEs 34 of the OEA 35, and the SMEs 2404 of the IEA 2405.

The plastic body member 3309 is an elongated, cylindrical, flexible member, which may be formed of a medical grade plastic polymer. It has a proximal end 3302 and a distal end 3301. Progressing along the lead from the proximal end 3302, these segments sequentially include a proximal lead segment 3302a, a mandibular electrode array (MEA) 3305, and a distal non-stimulating tip 3303.

Staying with FIG. 33, the MEA 3305 consists of a plurality of SMEs 3304 uniformly disposed over a portion of the ML 3300. Lead wires 3308 connect to the SMEs 3304 in the same fashion as depicted for the FEA as shown in FIG. 2. As is the case with respect to the FEA 25, the PEA 26, the OEA 35, and the IEA 2405, the SMEs 3304 of the ML3300 have an interelectrode spacing 3306 and a design that is specific for stimulating the nerves in the mandibular region. Also, the number of electrodes required for the array will be a function of the particular region—the mandibular region— that is being treated. As will be described hereinbelow, each of these electrodes can be designated as an anode or a cathode and any combination can be designated to be energized in a set-up procedure performed by a clinician. This provides a configuration that can be adapted to a particular patient at a particular placement of the ML 3305.

Figure 34:
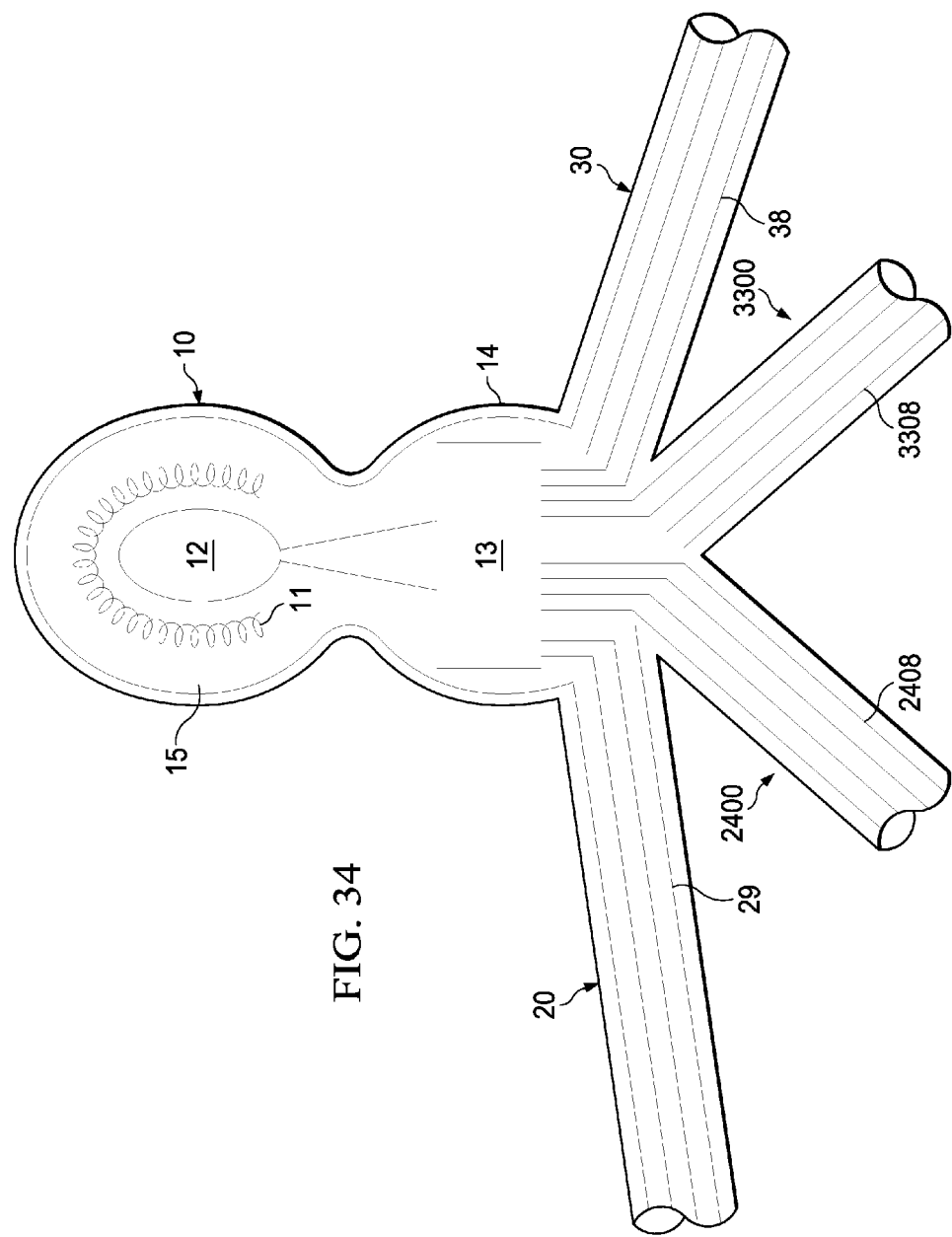
FIG. 34 illustrates a neurostimulator system IPG which includes connection for an occipital lead, a fronto-parietal lead, an infraorbital lead, and a mandibular lead.

Turning now to FIG. 34, there is illustrated a cutaway view of the IPG 10 for an embodiment which includes an IL 2400 and a ML 3300. Visible are the IL 2400 and the ML 3300 as well as the internal wires 2408 of the IL 2400 and the internal wires 3308 within the ML 3300 The internal wires 3308 run between the ASIC 13 and the SMEs 3304 on the LM 3300.

Figure 35:
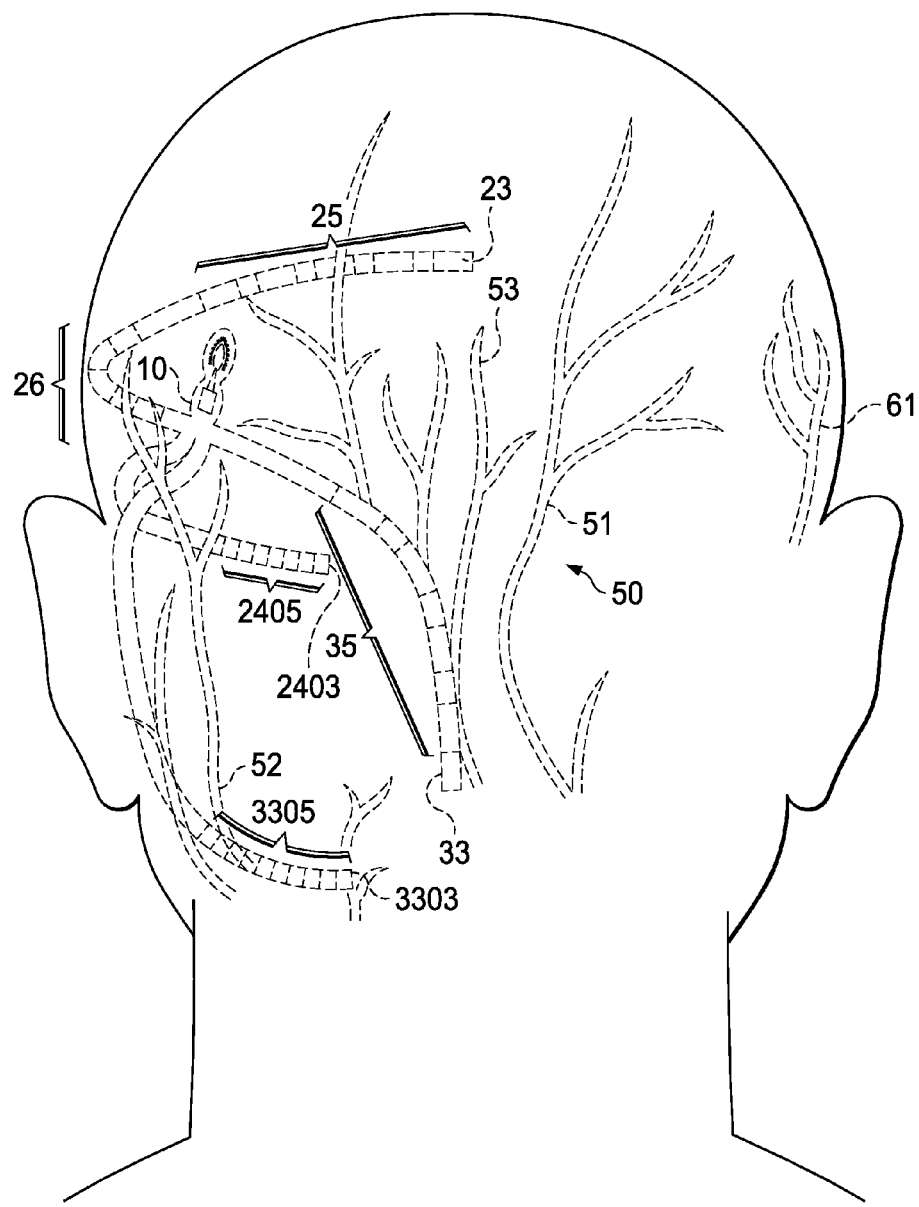
FIG. 35 illustrates the back of a head with an implanted neurostimulator system which includes an occipital lead, a fronto-parietal lead, an infraorbital lead, and a mandibular lead.

Turning now to FIG. 35, there is illustrated a rear view of a head with an embodiment of the full head-mounted neurostimulator system in-situ which includes the ML 3300. In addition to the PEA 26, the FEA 25, the OEA 35, and the IEA 2405 (as depicted in FIG. 26), there is also visible the MEA 3305.

Figure 36:
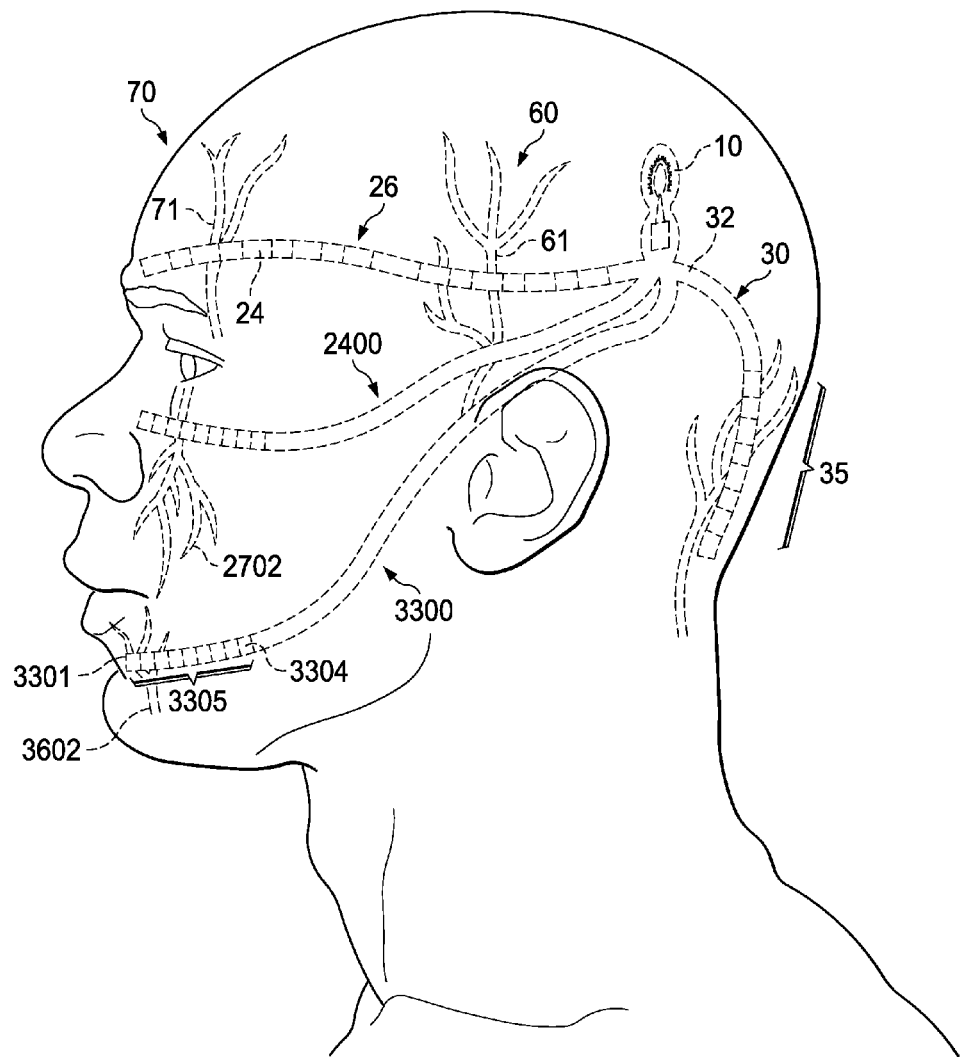
FIG. 36 illustrates the side of a head with an implanted neurostimulator system which includes an occipital lead, a fronto-parietal lead, an infraorbital lead, and a mandibular lead.

Turning now to FIG. 36, there is illustrated a side view of a head with an embodiment (the same embodiment depicted in FIG. 35) of the neurostimulator in-situ. In addition to the FPL 20, the OL 30, and the IL 2400, there is visible the ML 3300. Visible on the ML 3300 are the SMEs 3304 which comprise the MEA 3305. The ML is implanted under the skin of the patient and extends from the IPG 10, which is roughly above the ear, forward and down, such that the non-stimulating tip 3301 is on the chin under the and near the center of the mouth. The MEA 3305 will pass through the mandibular region and over the mental nerve 3602, which lies under the skin on the chin and under and beside the mouth proximate the mentalis muscle.

Figure 37:
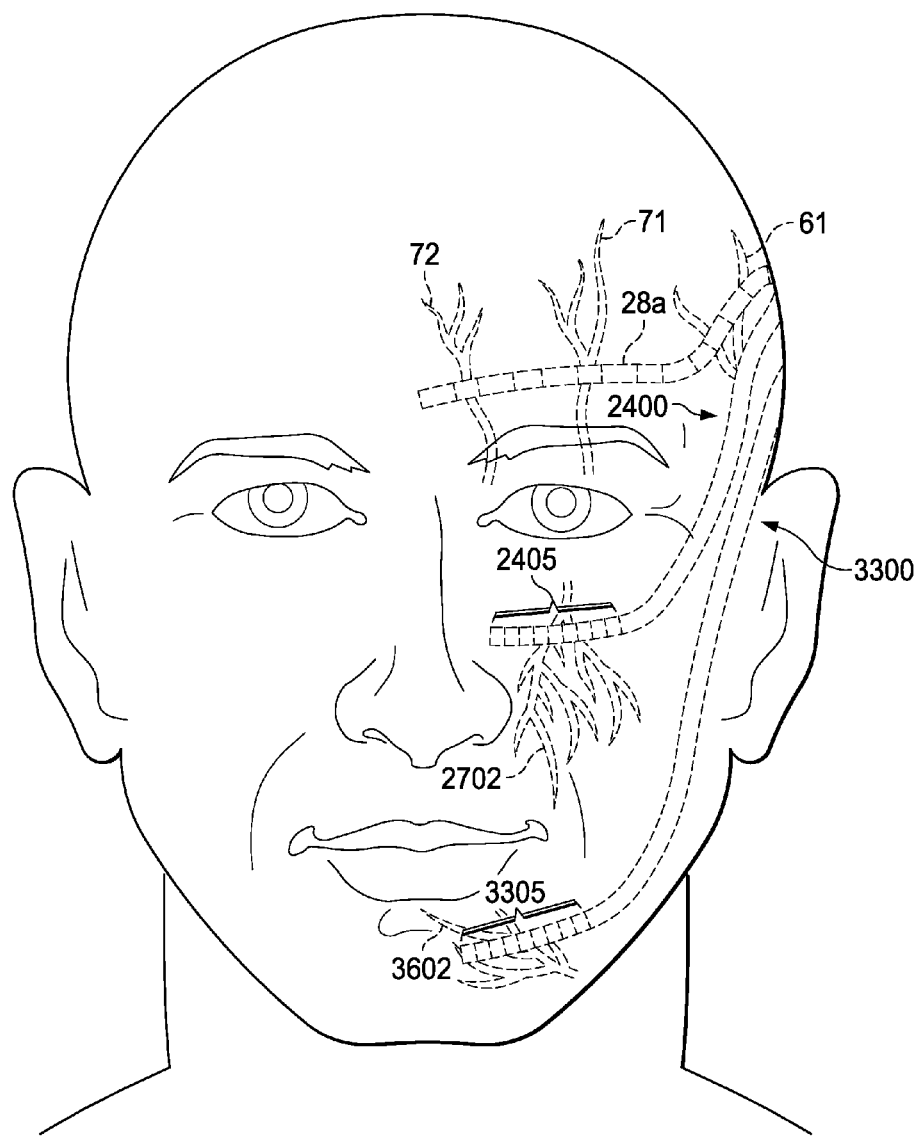
FIG. 37 illustrates the front of a head with an implanted neurostimulator system which includes an occipital lead, a fronto-parietal lead, an infraorbital lead, and a mandibular lead.

Turning now to FIG. 37, there is illustrated a front view of a head with an embodiment (the same as shown in FIGS. 35 and 36) of the neurostimulator system. The ML 3300 and the MEA 3305 are visible and positioned in the mandibular region of the head. The MEA 3305 lies over the mental nerve 3602.

Figure 38:
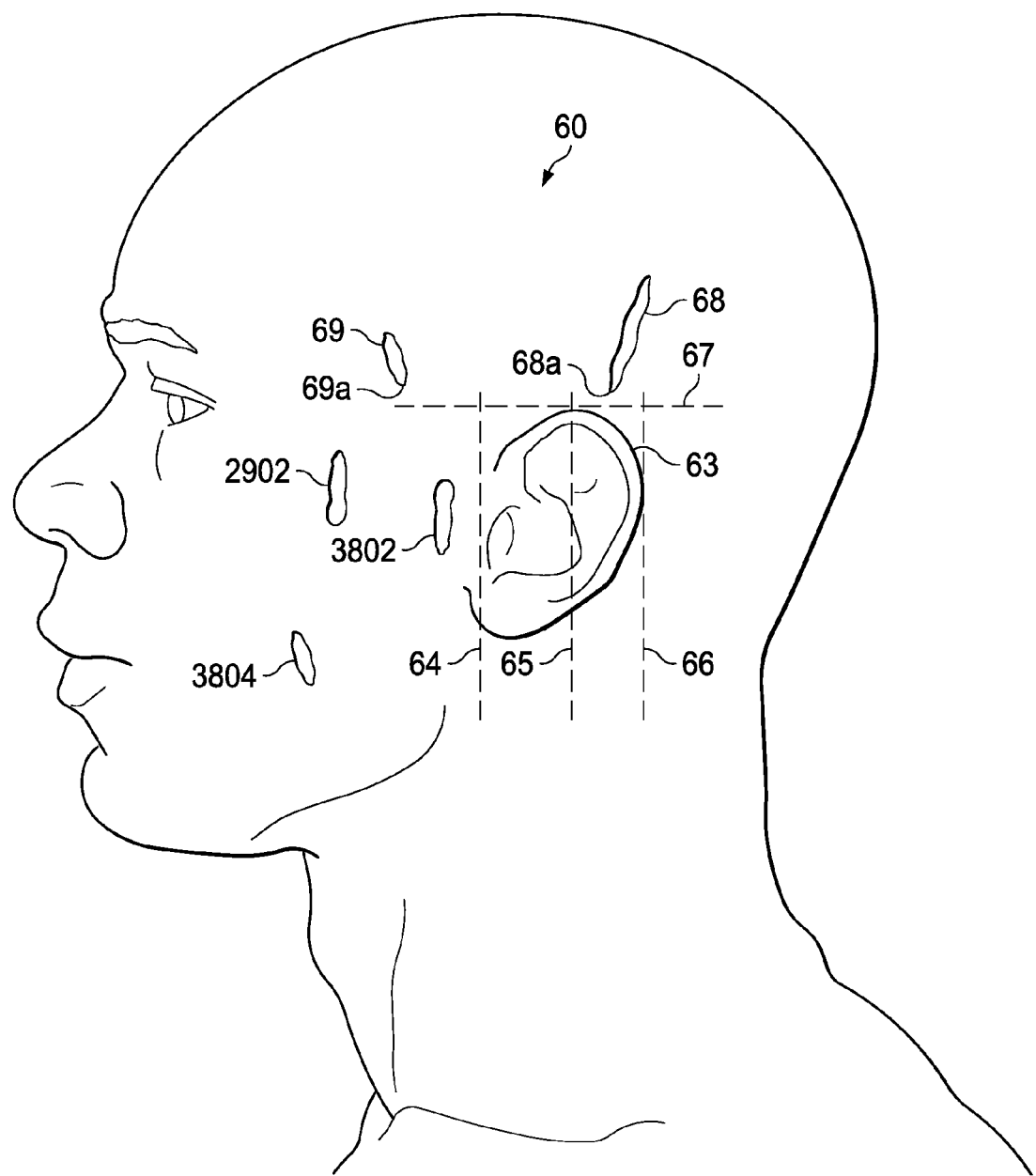
FIG. 38 illustrates the side of a head with incisions made for implanting a neurostimulator system which includes an occipital lead, a fronto-parietal lead, an infraorbital lead, and a mandibular lead.

Turning now to FIG. 38, there is illustrated a side view of a head and the initial interventional step in the procedure for implanting an embodiment of the neurostimulator system that includes an ML 3300. This step includes all of the incisions required for the FPL 20, the OL 30, and the IL 2400. An additional incision 3802 is made just in front of the ear, about halfway between the top and the bottom of the ear. Another incision 3804 is made at about chin level on the side of the jaw.

Figure 39:
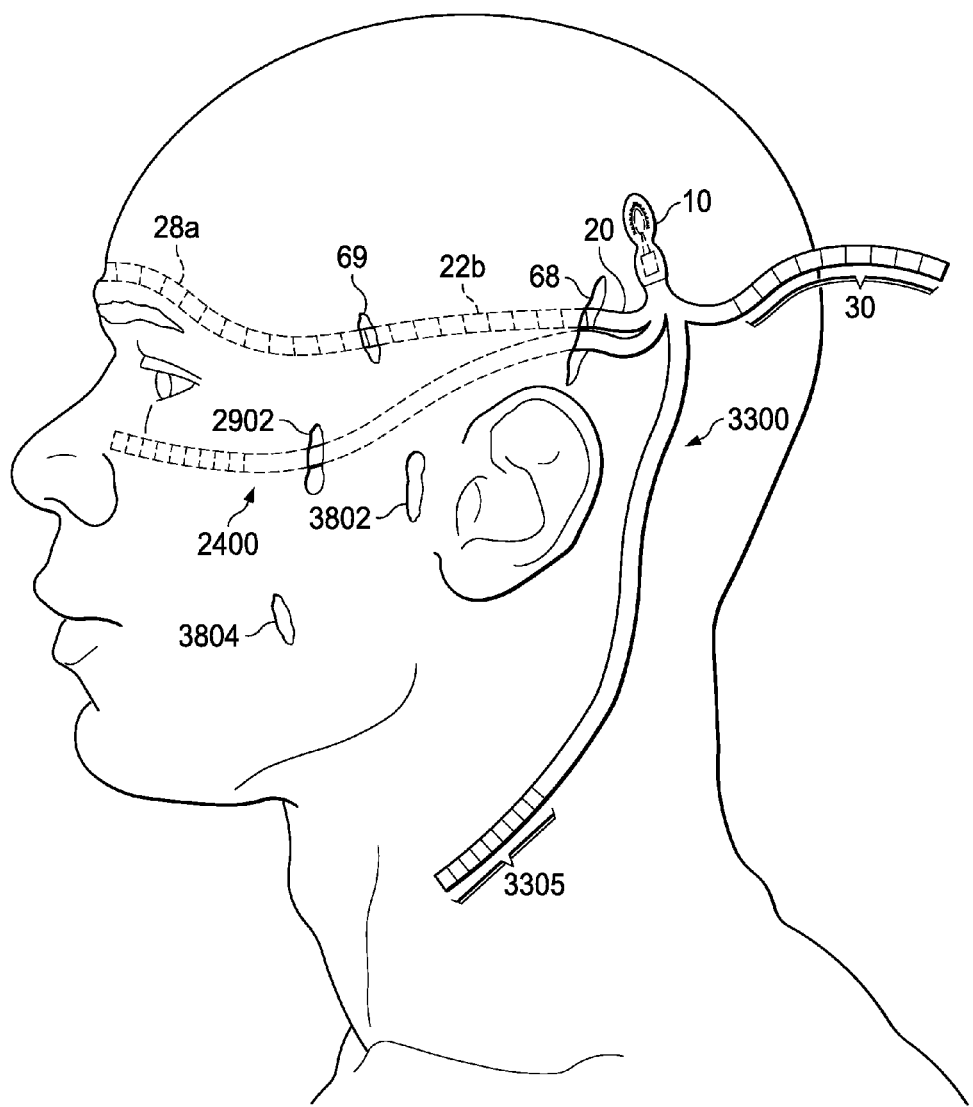
FIG. 39 illustrates the next step of implanting a neurostimulator system which includes a mandibular lead after the fronto-parietal and infraorbital leads are implanted.

Turning now to FIG. 39, there is illustrated the step of the procedure following that depicted in FIG. 32 and as described hereinabove with respect to FIG. 10. That is, the FPL 20 and the IL 2400 have been implanted and placed in their final positions. As explained earlier, embodiments which have a ML 3300, in addition to the FPL 20, the OL 30, and the IL 2400, will have steps for implanting the neurostimulator system that are cumulative to the embodiments which have only the FPL 20, an OL 30, and a IL 2400. Therefore, the step depicted in FIG. 39 begins with the FPL 20 and the IL 2400 already having been implanted and positioned in the appropriated locations as described hereinabove with respect to FIG. 32. The OL 30 and the ML 3300 are positioned outside the patient's skin, ready to be placed in their appropriate subcutaneous locations.

Figure 40:
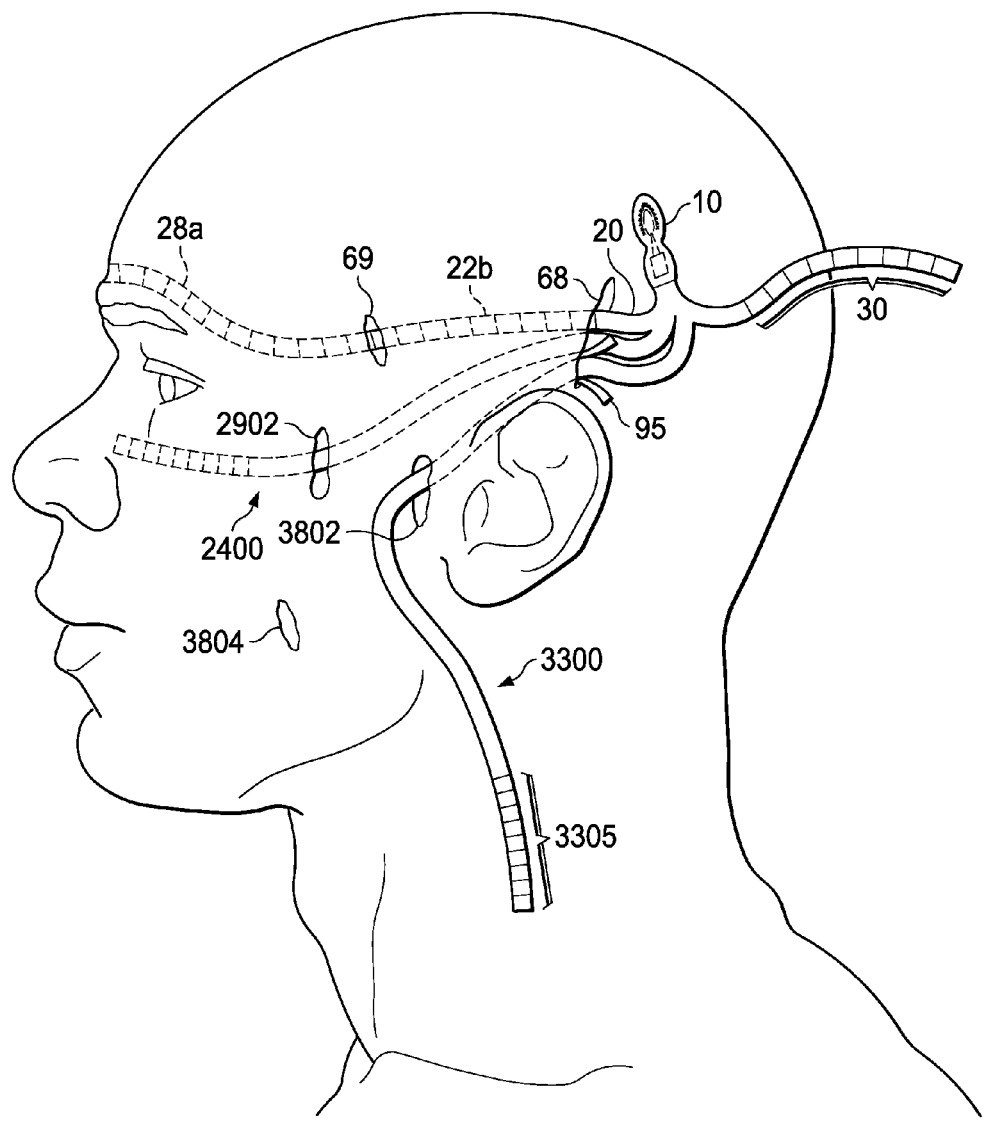

Turning now to FIG. 40, there is illustrated a side view of a head and the next step, following the step described in FIG. 39, of implanting the ML 3300. The step is roughly analogous to the step described hereinabove with respect to FIG. 10 for the FPL 20. In this step, a peel-away introducer 95 is passed subcutaneously through the incision 68 to the incision 3802. The ML 3300 is then passed subcutaneously through the introducer 95 from the incision 68 to the incision 3802. Once the ML 3300 is passed through lumen of the introducer 95, it is pulled through such that the distal portion of the ML 3300 with the MEA 3305 is pulled all the way through the incision 3802. The peel-away introducer 95 can then be extracted in the way described with respect to FIG. 10.

Figure 41:
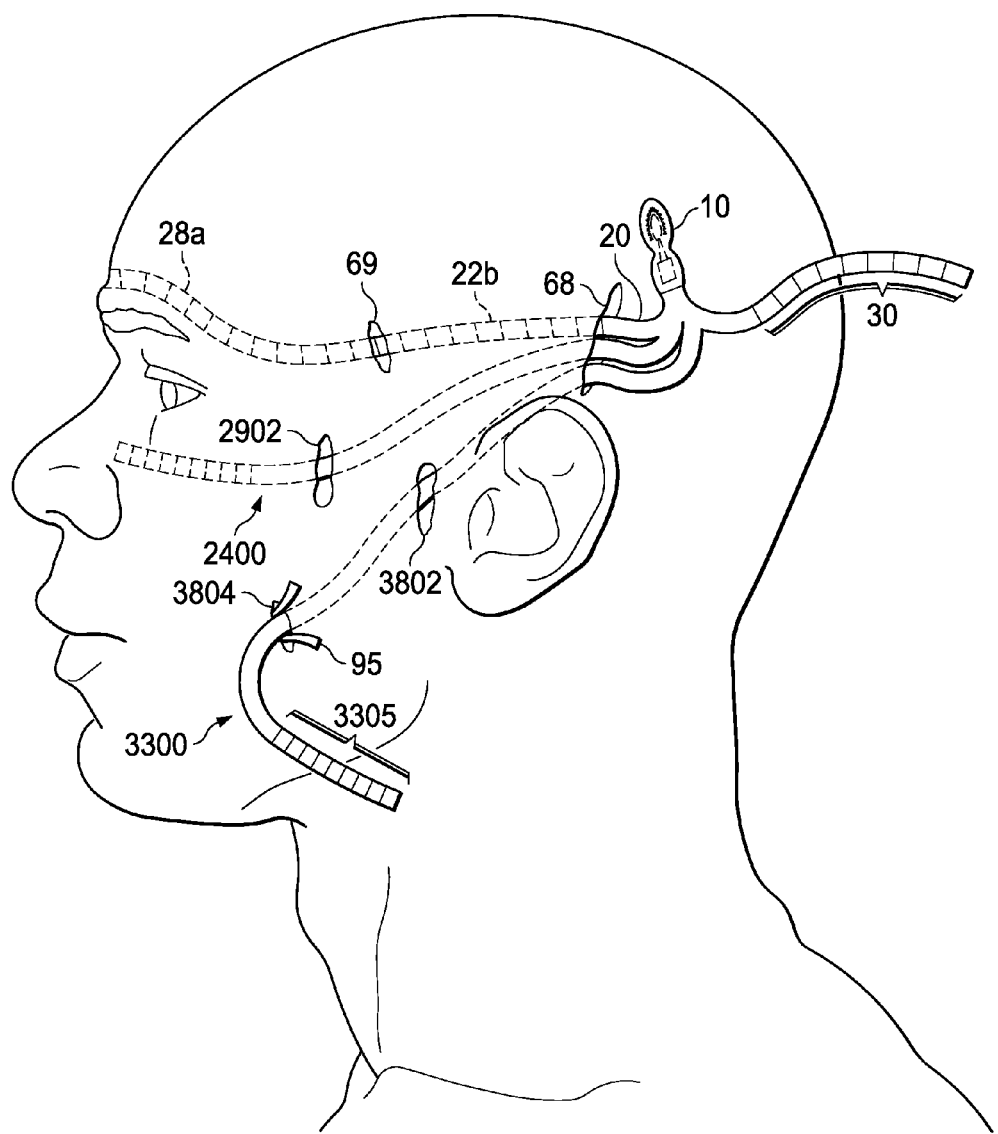
FIG. 41 illustrates the step of inserting the mandibular lead into a second incision.

Turning next to FIG. 41, there is illustrated a side view of a head and the next step of implanting the ML 3300, following the step described in FIG. 40. This step is again similar to the step described hereinabove with respect to FIG. 10 for the FPL 20. In this step, another peel-away introducer 95 is passed subcutaneously through the incision 3802 to the incision 3804. The distal portion of the ML 3300 (which, as described with respect to FIG. 40, was pulled out of the incision 3802) is placed back in the incision 3802 and passed subcutaneously through the introducer 95 from the incision 3802 to the incision 3804. Once the ML 3300 is passed through the lumen of the introducer 95, it is pulled through such that the distal portion of the ML 3300 with the MEA 3305 is pulled all the way through the incision 3802. The peel-away introducer 95 can then be extracted in the way described with respect to FIG. 40.

Figure 42:
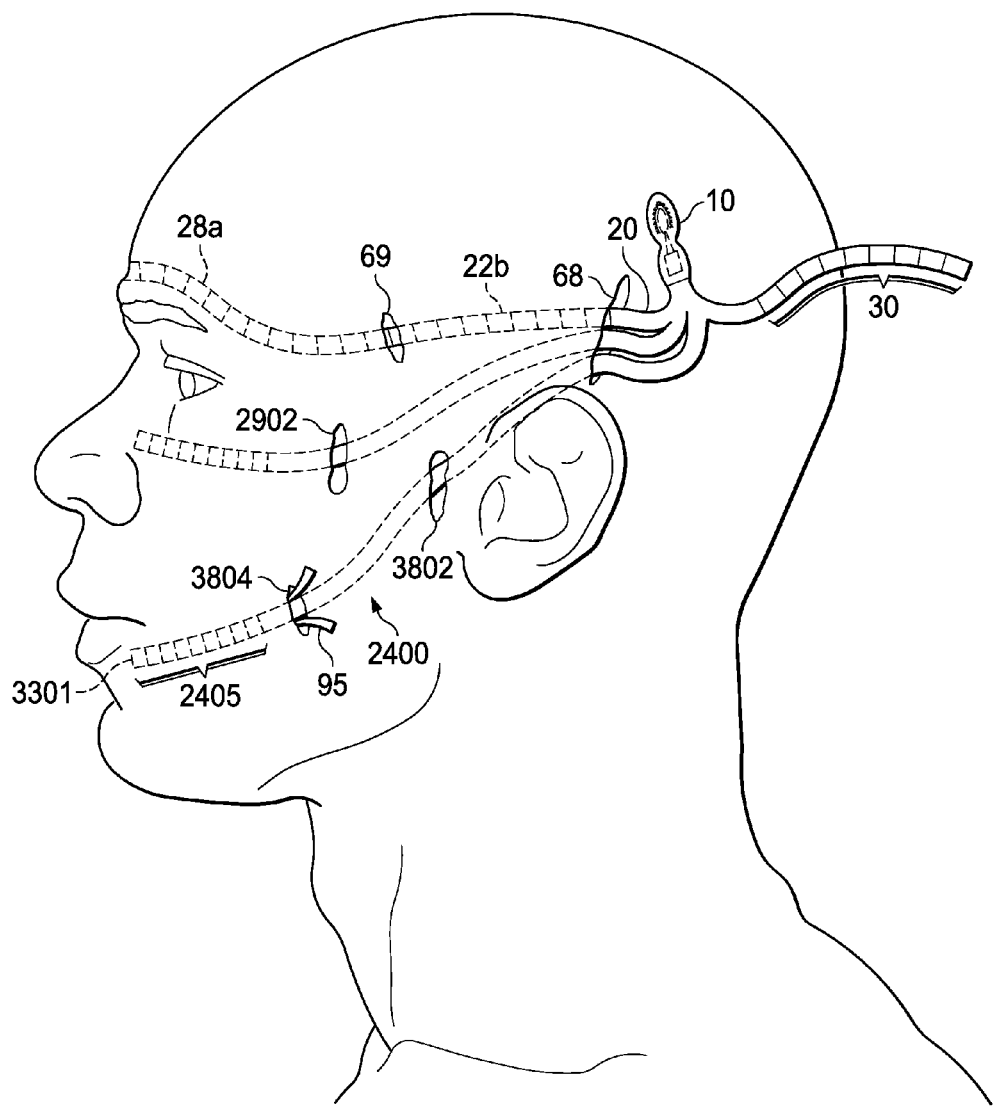
FIG. 42 illustrates the step of inserting the mandibular lead into a third incision.

Turning to FIG. 42, there is illustrated a side view of a head and the next step, following the step described with respect to FIG. 41, of implanting the ML 3300 in embodiments which include the ML 3300. Another peel-away introducer 95 is passed subcutaneously from the incision 3804 to the final position of the ML 3300 proximate to the mandibular region. The distal portion of the ML 3300 (which, as described with respect to FIG. 31, was pulled out of the incision 3804) is placed back in the incision 3804 in the introducer 95 and positioned such that the non-stimulating distal end 3301 will be over the mandibular nerve bundle on the chin under the mouth and on the forward portion of the jaw. The ML 3300 having now been placed in its final position, the peel-away introducer 95 is then removed from the incision 3804. The OL 30 and the IPG 10 are then subcutaneously implanted in the same way as for embodiments that do not include a ML 3300, such as those that only include an FPL 20 and an OL 30, or an FPL 20, an OL 30, and an IL 2400. That is, the OL 30 and IPG 10 are implanted in the same way as is described hereinabove with respect to FIGS. 12-15.

It should be noted that not all embodiments of the neurostimulation system which include a ML 3300 will require both the incision 3802 and the incision 3804 for implantation. Some embodiments will only require the incision 3802, while other embodiments will only require the incision 3804. Also, the exact positions of one or both of the incisions 3802, 3804 will be different in different embodiments and may also depend on the particular patient and surgeon.

Figure 43:
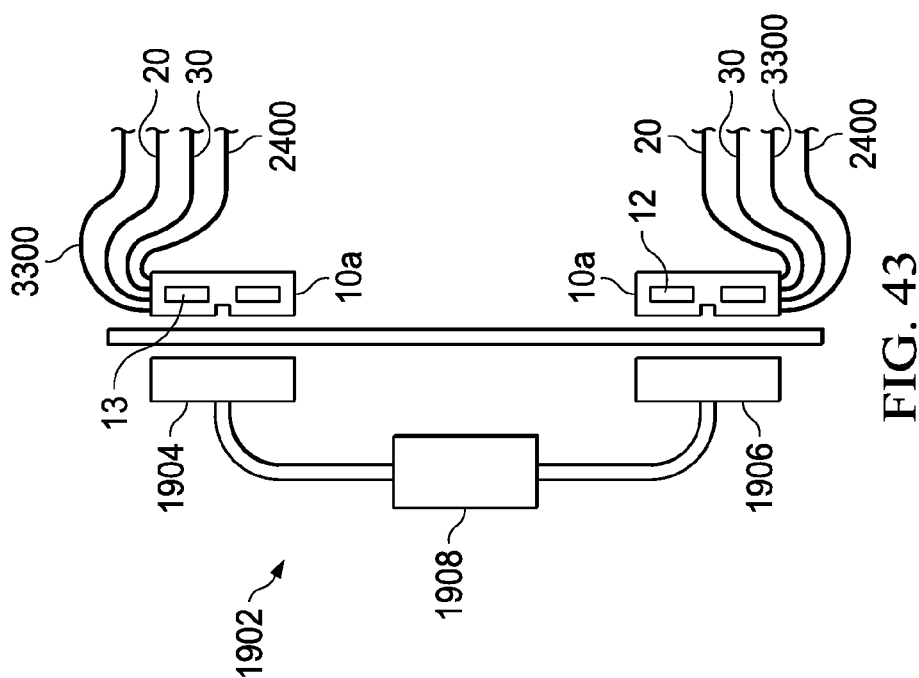
FIG. 43 illustrates a diagrammatic view of the headset interfaced with the implants.

Referring now to FIG. 43, there is illustrated a diagrammatic view of an embodiment of the interface of the headset 1902 with the implants 10a, similar to the embodiment depicted and described hereinabove with respect to FIG. 20. The embodiment depicted in FIG. 43, however, includes an IL 2400 and a ML 3300. Each of the implants 10a is interfaced with the leads 20, 30, 2400, and 3300 and includes the processor 13 and the battery 12. It should be understood that similar interfaces exist in embodiments which have other combinations of leads, such as an OL 20, a FPL 30, and a IL 2400, or embodiments which have an OL 20, a FPL 30, and a ML 3300.

Figure 44:
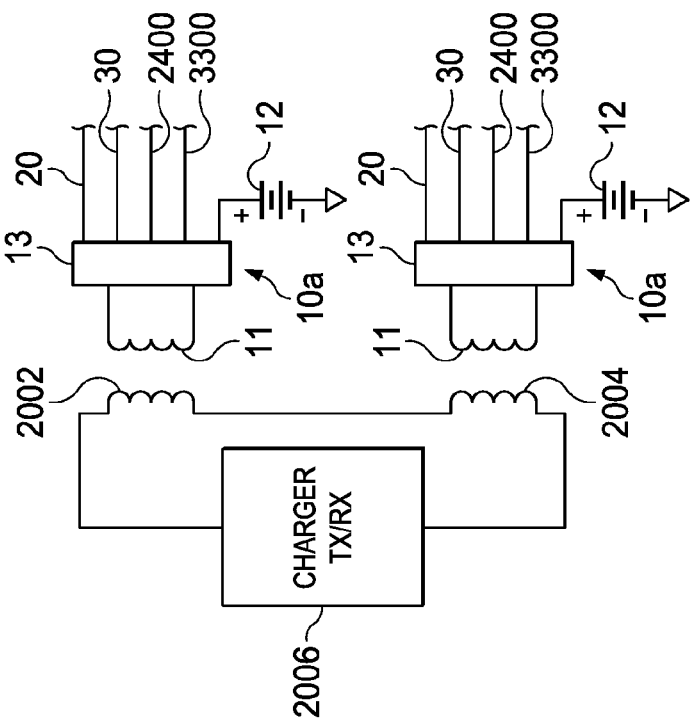
FIG. 44 illustrates a schematic view of the implants and headset.

Referring now to FIG. 44, there is illustrated a schematic view of the overall headset and implants, analogous to the headset and implants depicted and described hereinabove with respect to FIG. 21 with an OL 20 and a FPL 30, for an embodiment which includes an IL 2400 and a ML 3300. Again, it should be understood that some embodiments will have other combinations of leads, such as an OL 20, a FPL 30, and an IL 2400, or an OL 20, a FPL 30, and a ML 3300.

Figure 45:
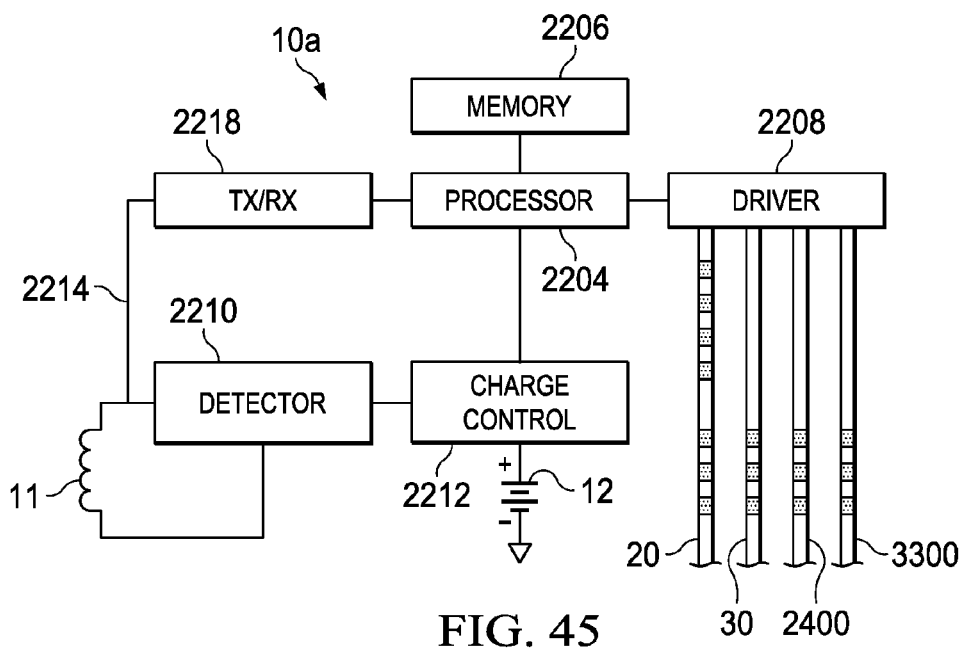
FIG. 45 illustrates a block diagram of the headset/charger system.

Referring now to FIG. 45, there is illustrated a block diagram for implantation 10a, similar to the bock diagram of implantation 10a depicted and described hereinabove with respect to FIG. 22A. The embodiment depicted in FIG. 45, however, includes an IL 2400 and a ML 3300. Therefore, the driver 2208 drives not only OL 20 and FPL 30, but also IL 2400 and ML 3300. It should be understood that other embodiments will have other combinations of leads, such an OL 20, a FPL 30, and an IL 2400 in some embodiments, or an OL 20, a FPL 30, and a ML 3300 in other embodiments.

Figure 46:
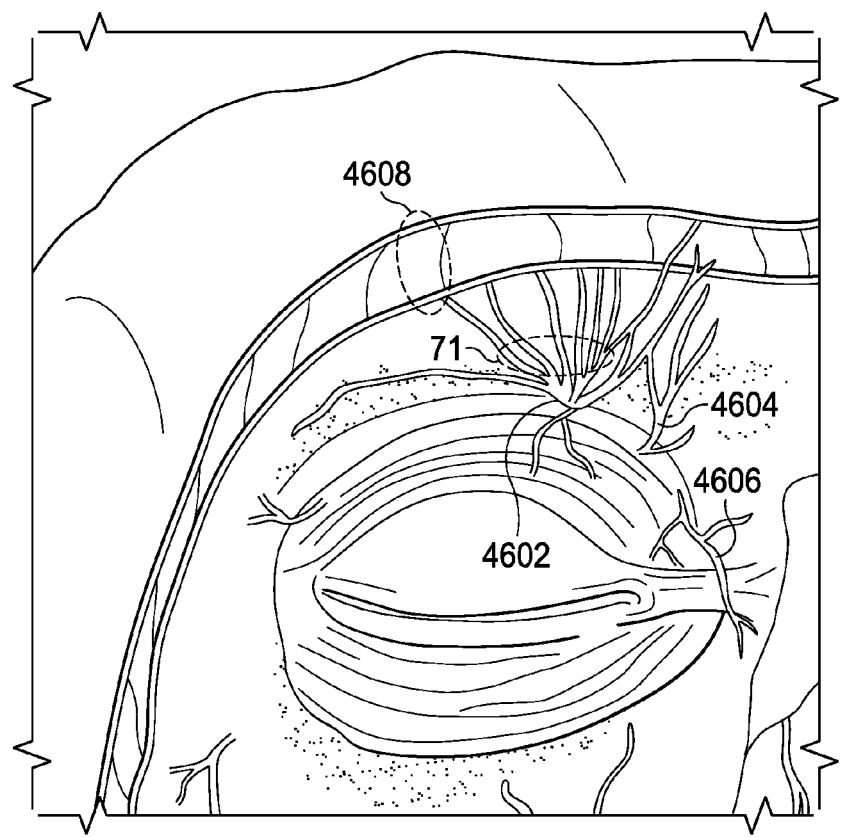
FIG. 46 illustrates a detailed view of the supraorbital nerve.

Turning now to FIG. 46, there is illustrated a diagram which shows a more realistic illustration of the supraorbital nerve 71. What has been described as the supraorbital nerve 71 can also be considered in terms of the various smaller nerves in the region near the supraorbital nerve 71. Of note in FIG. 46 are the supraorbital nerve 71, the supraorbital fossa 4602, supratrochlear nerves 4604, and infratrochlear nerve 4606. A cutaway view of the dermis 4608 is also visible. It should be appreciated that each individual, as they are developing in the womb, can form these nerve bundles in different manners. The bundles can have slightly different positions and different branching patterns.

Figure 47:
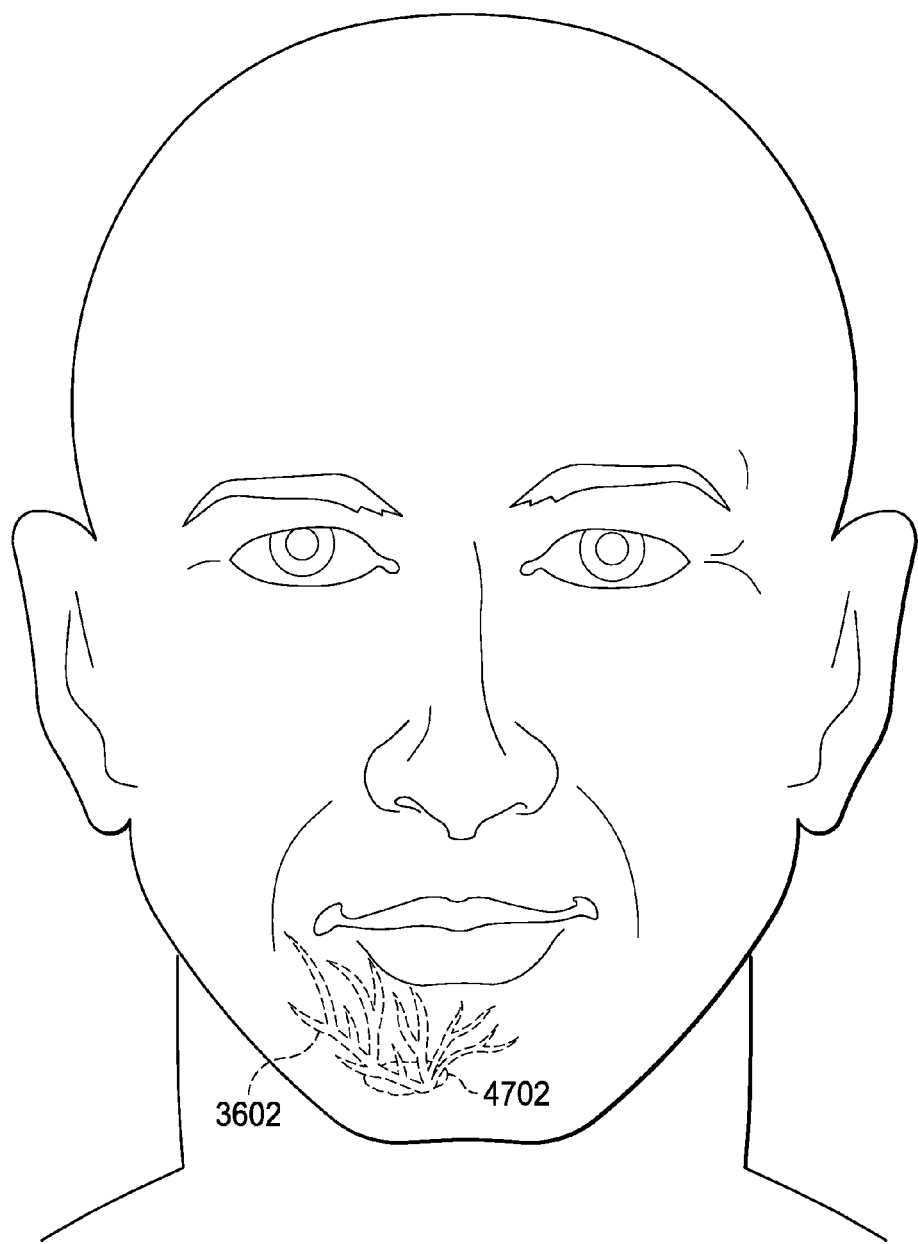
FIG. 47 illustrates a detailed view of the mental nerve.

Turning now to FIG. 47, there is illustrated a more detailed diagram of the region of the face which includes the mental nerve bundle 3602. The mental nerve 3602 emerges from the mental foramen 4702 and spreads out in the lower lip and chin.

Figure 48:
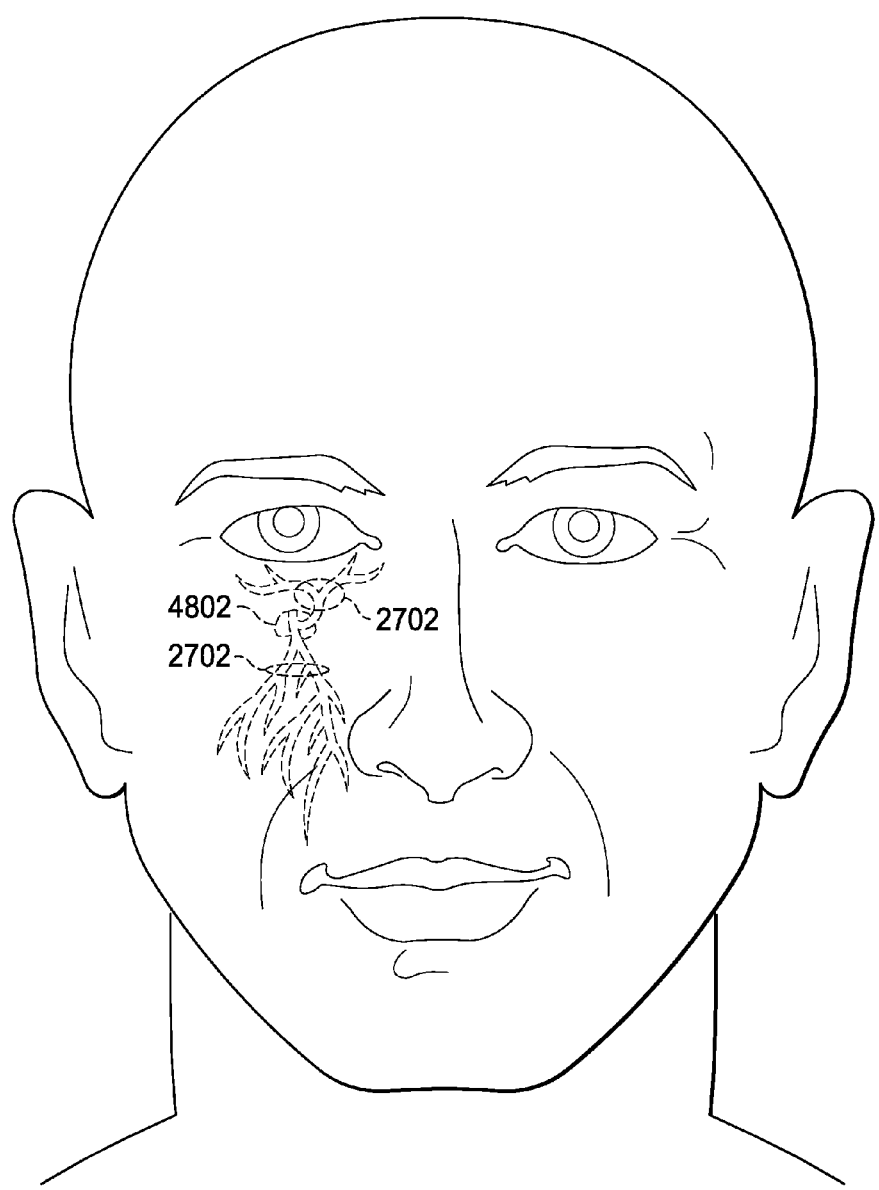
FIG. 48 illustrates a detailed view of the infraorbital nerve.

Turning now to FIG. 48, there is illustrated a more detailed diagram of the region of the face which includes the infraorbital nerve bundle 2702. The infraorbital nerve 2702 emerges from the infraorbital foramen 4802 and has branches which radiate to the lower eyelid, dorsum of the nose, the vestibule of the nose, and the upper lip.

Figure 49:
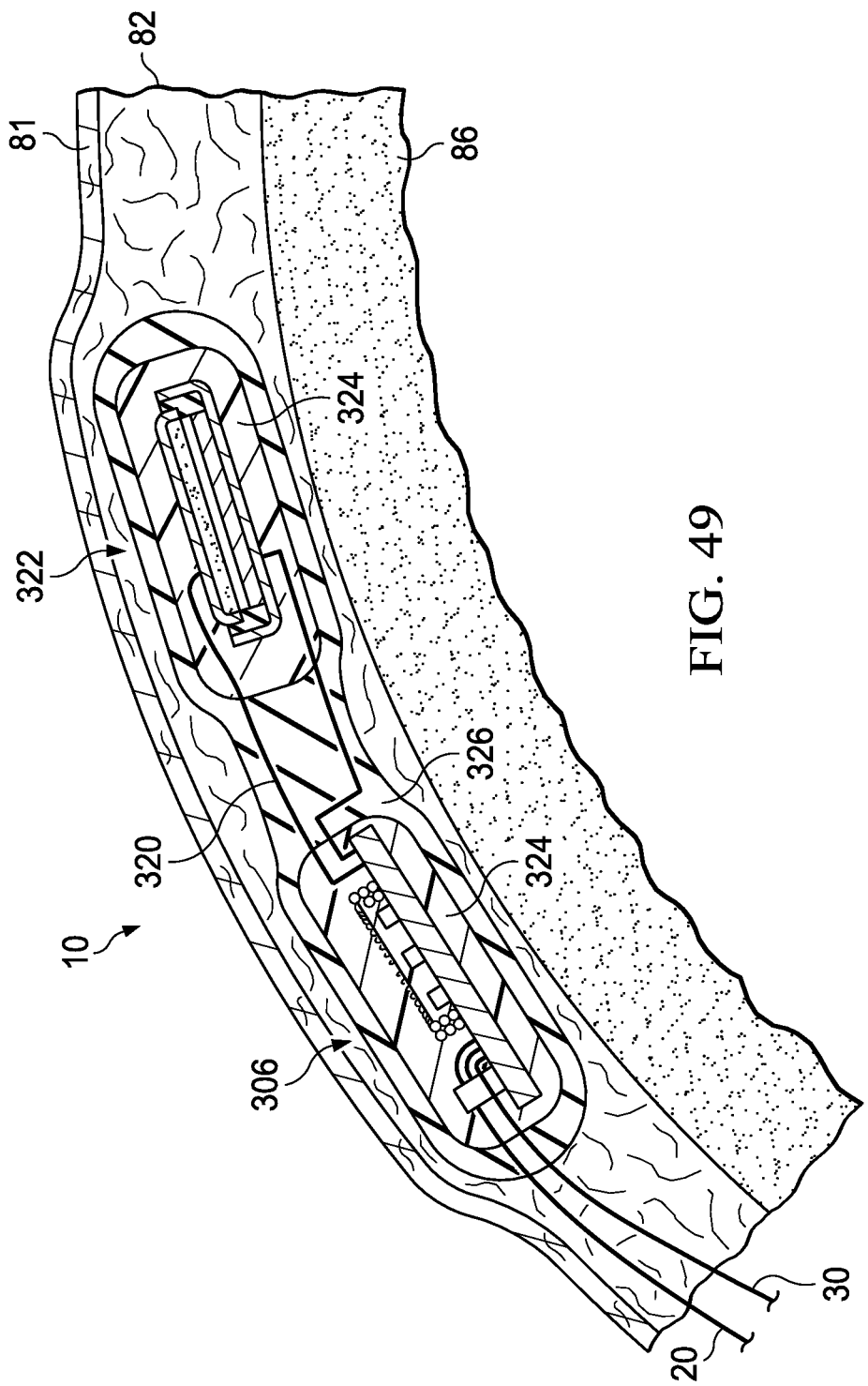
FIG. 49 illustrates a flexible IPG implanted in the subcutaneous tissue surrounding a skull.

Turning now to FIG. 49, there is illustrated a cross-sectional side view of an embodiment of the IPG 10 implanted in the subcutaneous tissue 82 of a patient's head. FIG. 49 illustrates how some embodiments of IPG 10, such as those illustrated in FIGS. 3E-3J and 3M-3N, have a flexible silicone coating 326 which allows the IPG 10 to better conform to a curved implantation site, such as under the dermis 81 on the outside of the skull 86. Since the skull 86 has a curved surface, if an IPG 10 that is implanted in the subcutaneous tissue 82 above the skull cannot bend or flex, the IPG 10 will not conform as well to the shape of the skull, resulting in increased pressure on the dermis 81 and possible increased discomfort for the patient. An IPG 10 with a flexible silicone coating 326 which better conforms to curved surfaces not only will result in decreased discomfort, but will also reduce the visibility of the implant, as an IPG 10 which lies relatively flat under the dermis 81 will be less noticeable.

Figure 50:
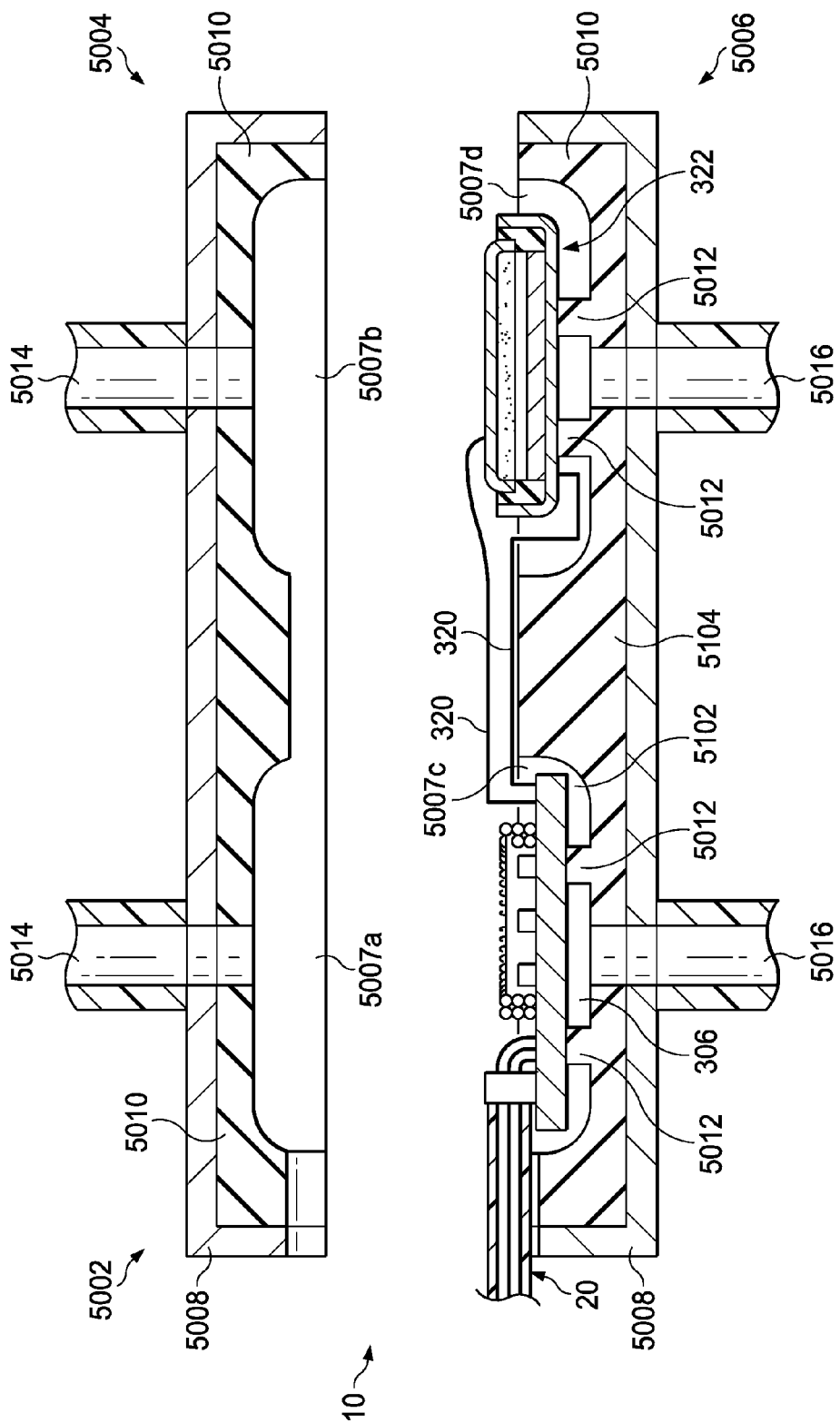
FIG. 50 illustrates a cross-sectional side view of the first step in an embodiment of applying an epoxy coating to an IPG.

Turning now to FIG. 50, there is illustrated a cross-sectional side view of embodiment of an IPG 10 that does not yet have an epoxy coating 324. In some embodiments of the IPG 10 which include epoxy coatings 324 covering the ASIC body 306 and the battery body 322, the epoxy coatings are applied via a process which creates a vacuum within a mold containing the IPG 10 and then injects epoxy into the mold surrounding the IPG. This allows epoxy coatings 324 to encapsulate both the ASIC body 306 and the battery body 322. In the embodiment illustrated in FIG. 50, the mold 5002 includes a top mold half 5004 and a bottom mold half 5006. The mold halves 5004, 5006 each include cavities 5007 within them to accommodate the ASIC body 306 and the battery body 322 when the IPG 10 is placed in the mold. The mold halves 5004, 5006 are made of a rigid outer casing 5008, such as aluminum, steel, or any other appropriate metal or material, with the inner shaping portions 5010 being made of a high durometer silicone or another appropriate material which is less rigid than the outer casings 5008, but still rigid enough to resist collapsing then "filled" with a vacuum or near vacuum. The mold bottom half 5006 includes small pedestals 5012 on which the ASIC body 306 and the battery body 322 rest while the IPG 10 is inside the mold 5002. This allows the ASIC body 306 and the battery body 322 to be somewhat "suspended" within the mold so that epoxy can flow around all sides of the ASIC and battery bodies. The pedestals 5012 are made of the same material as the inner shaping portions 5010. The mold top half 5004 includes an epoxy port 5014 over cavity 5007a which accommodates the ASIC body 306 and an epoxy port 5014 over the cavity 5007b which accommodates the battery body 322. Each of these epoxy ports 5014 extends from the exterior of the mold top half 5004 all the way into one of the cavities 5007 of the mold top. Similarly, the mold bottom half 5006 includes a vacuum port 5016 under the cavity 5007c that accommodates the ASIC body 306 and a vacuum port 5016 under the cavity 5007d that accommodates the battery port 322. Each of these vacuum ports 5016 extends from the exterior of the mold 5002 through the mold bottom half 5006 into one of the cavities 5007 of the mold bottom half 5006.

As is illustrated in FIG. 50, the first step in applying the epoxy coatings 324 to the IPG 10 is to place the IPG 10 within the disassembled mold 5002 such that the ASIC body 306 and the battery body 322 each rest on the pedestals 5012. The FPL 20 (other or additional leads are included in other embodiments) extends out of the mold cavities 5007 and out of the mold 5002 via a pathway through the inner shaping portions 5010 and the casings 5008.

It should be noted that in some embodiments, a very thin layer of silicone is applied to the surfaces of the ASIC body 306 and of the battery body 322 before the IPG is placed in the mold 5002. Applying a thin layer of silicone will provide a flexible barrier between the IPG 10 components and the epoxy coatings 324. This can help avoid problems associated with the IPG 10 components and the epoxy coatings 324 expanding and contracting at different rates as they heat up and cool down. This thin layer can be formed by a spray or dipping, such that the layer is conformal. Prior to forming this thin coating, the entire surface is cleaned with an appropriate solvent such as acetone.

Figure 51:
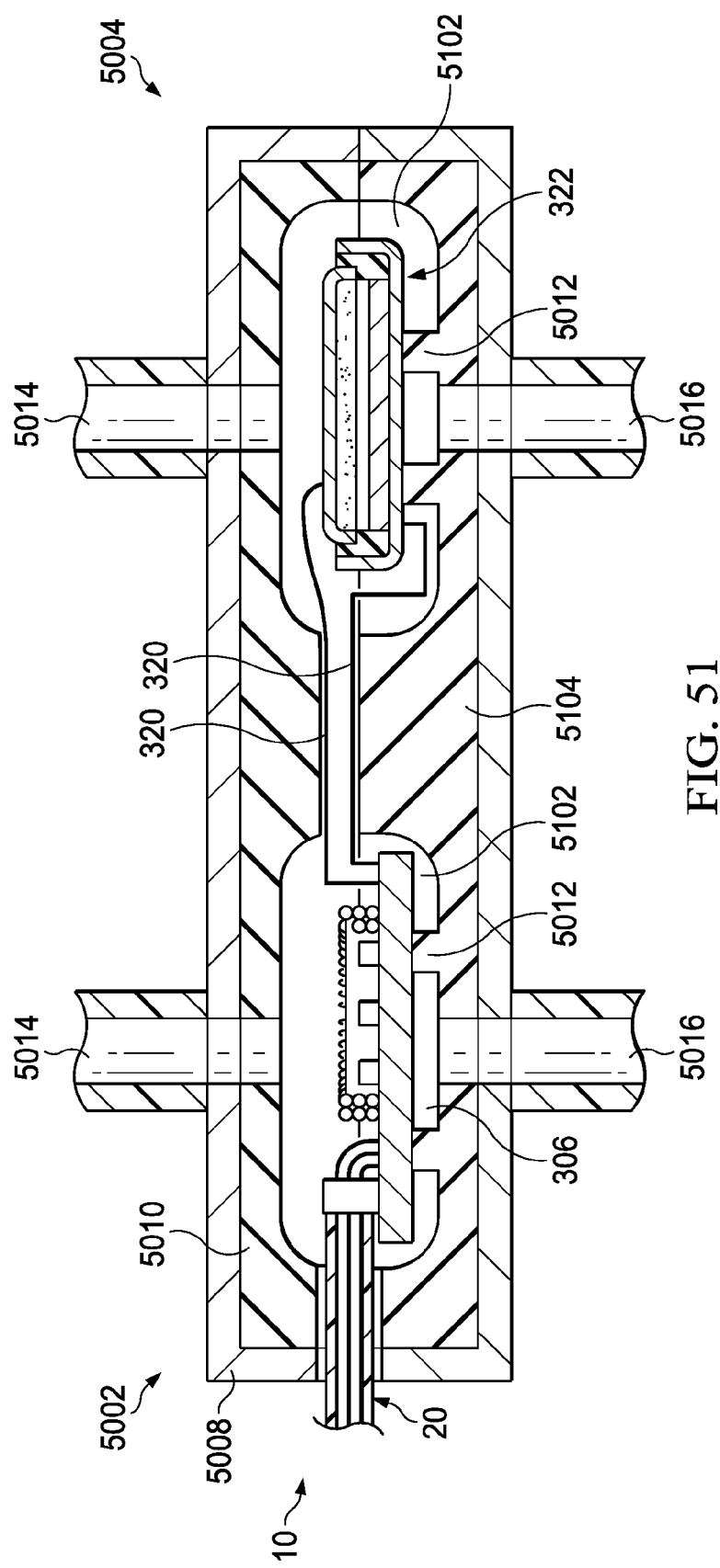
FIG. 51 illustrates a cross-sectional side view of an IPG being placed inside a mold for applying an epoxy coating.

Turning now to FIG. 51, there is illustrated a cross-sectional side view of the next step in applying the epoxy coating 325 to the IPG 10. After the IPG 10 has been placed on the pedestals 512 of the mold bottom half 5006, the mold 5002 is assembled by placing the mold top half 5004 together with the mold bottom half with the inner shaping portions 5010 of each half facing each other. The ASIC body 306 and the battery body 322 are now each enclosed in chambers 5102 (formed by the cavities 5007) which will be filled with epoxy to form the epoxy coatings 324. The chambers 5102 are separated from each other by sections of the inner shaping portions 5010 which press together to form a seal 5104 between the chambers. Since the inner shaping portions 5010 are made of a mildly flexible material such as silicone, the parts of the inner shaping portions 5010 forming the seal 5104 are compressible enough to allow the straps 320 which connect the ASIC body 306 to the battery body 322 to fit between the shaping portions 310 of the top mold half 5004 and the bottom mold half 5006 and extend from one chamber 5102 to the other chamber. In some embodiments, the inner shaping portion 5010 of one or both to the mold halves 5004, 5006 may be recessed slightly to better allow the straps 320 to extend from one chamber 5102 to the other. In either case, the seal is tight enough when vacuum is applied to prevent epoxy from flowing out of the chambers 5102. The FPL 20 (and other leads in other embodiments) extends through the inner shaping portion 5010 and through a gap in the outer casing 5008 to the exterior of the mold 5002. In some embodiments, the inner shaping portion material 5010 will deform enough to accommodate the FPL 20, while in others, there is a small gap that allows the FPL to fit between the mold halves 5004, 5006 while still creating a good seal that will prevent epoxy from leaking out of the mold 5002.

Figure 52:
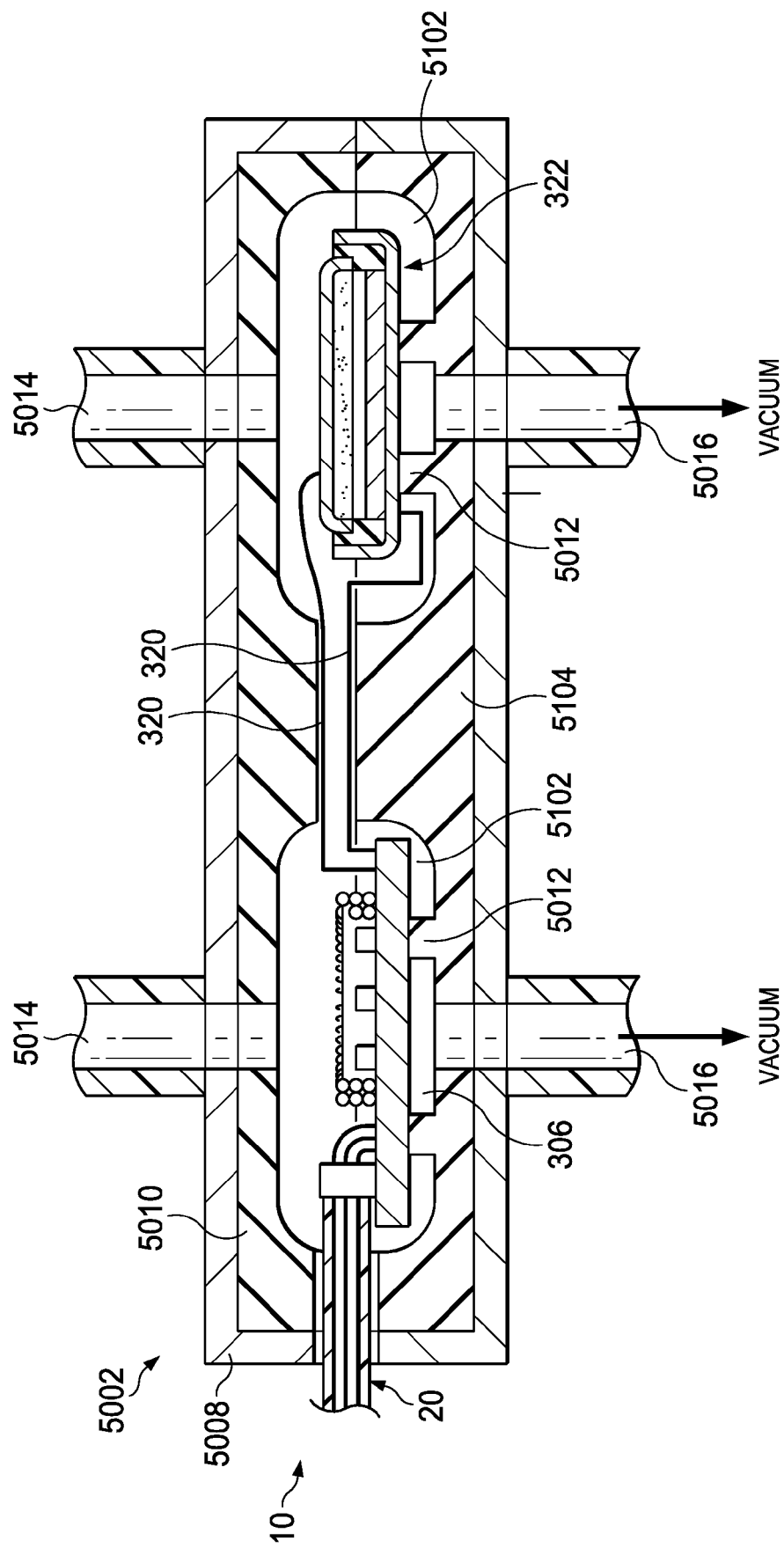
FIG. 52 illustrates a cross-sectional side view of a vacuum being created inside a mold for applying an epoxy coating to an IPG.

Turning now to FIG. 52, there is illustrated a cross-sectional side view of an IPG 10 and a mold 5002 in the next step in applying the epoxy coatings 324. Once the IPG 10 is positioned within the assembled mold 5002 as described hereinabove with respect to FIG. 51, a vacuum is pulled from the vacuum ports 5016. The causes the air to be removed from the cavities 5102 (or at least enough of the air to create a near vacuum). At this point, any residual solvent or cleaner that might still be on parts of the IPG 10 will also evaporate and be removed with the air.

Figure 53:
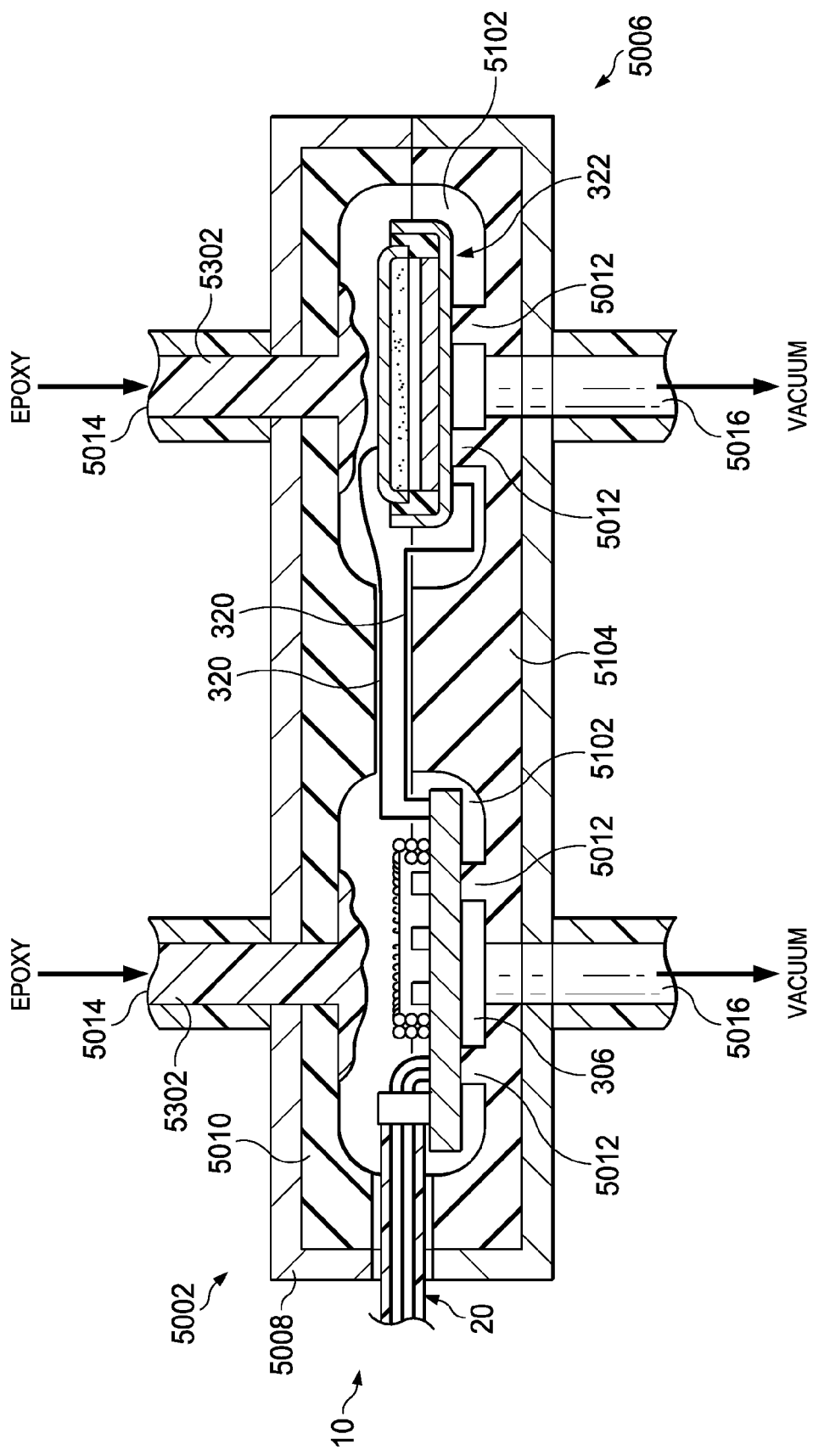
FIG. 53 illustrates a cross-sectional side veiw of the step of injecting epoxy into a mold for applying an epoxy coating to an IPG.

Turning now to FIG. 53, there is illustrated a cross-sectional side view of the next step in applying the epoxy coating 324. In this step, after a vacuum has been applied to the vacuum ports 5016 for a predetermined amount of time, epoxy 5302 is injected into the cavities via the epoxy ports 5014. The fact that there is a vacuum within the cavities 5102 helps the epoxy 5302 flow into the cavities. As the epoxy 5302 flows into the cavities 5102, it begins fill the cavities 5102 and to flow around and coat the ASIC body 306 and battery body 322 to form the epoxy coatings 324.

Figure 54:
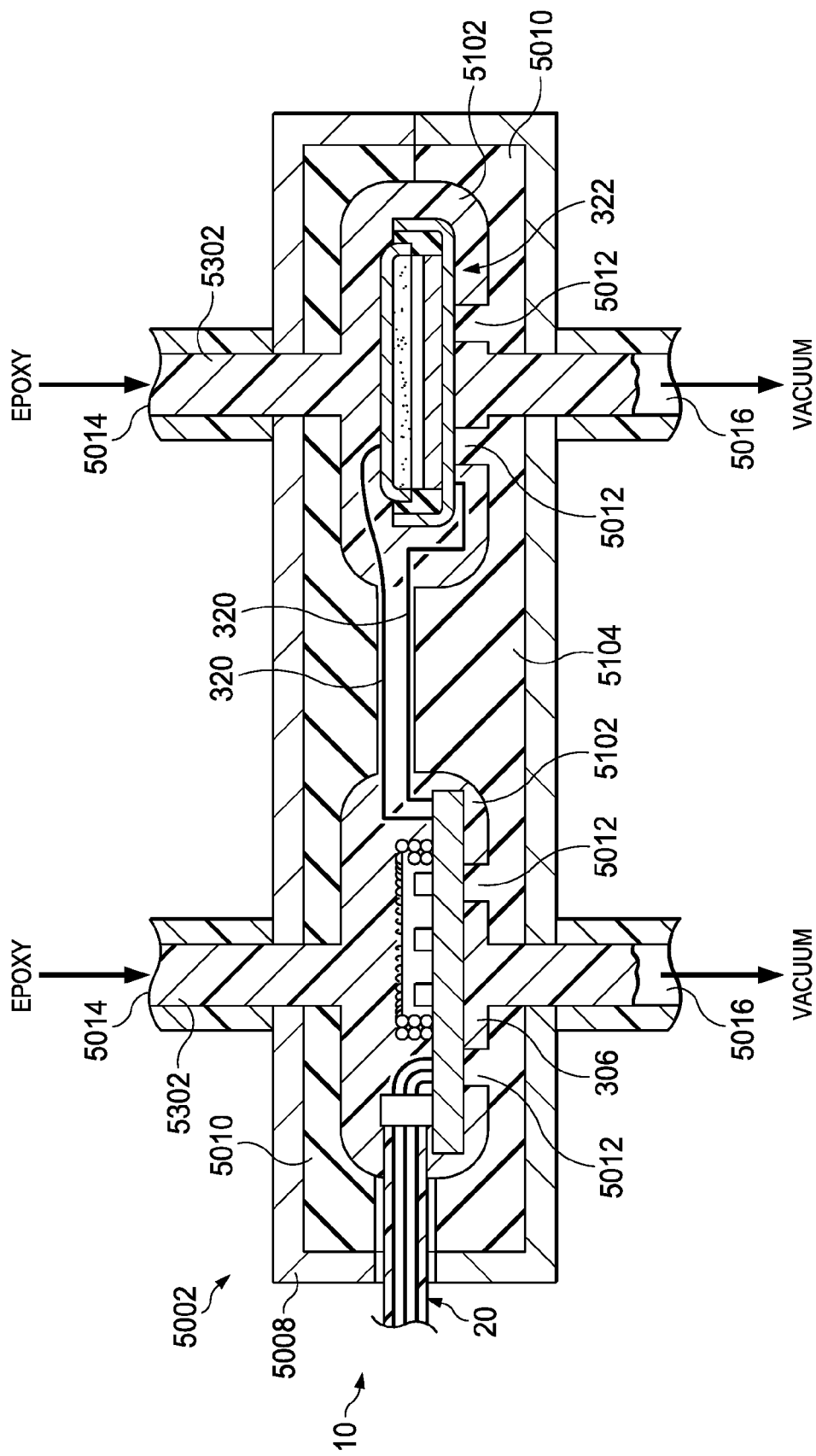
FIG. 54 illustrates a cross-sectional side view of another step of applying an epoxy coating to an IPG.

Turning now to FIG. 54, there is illustrated a cross-sectional side view of the next step in applying the epoxy coating 324. As the epoxy 5302 continues to be injected into the cavities 5102, it continues to fill the cavities and cover the ASIC body 306 and battery body 322 until it completely covers them and completely fills both cavities. At this point, the epoxy 5302 ceases to be injected into the epoxy ports 5014. The epoxy 5302 is allowed to cure and harden into the epoxy coatings 324.

Figure 55:
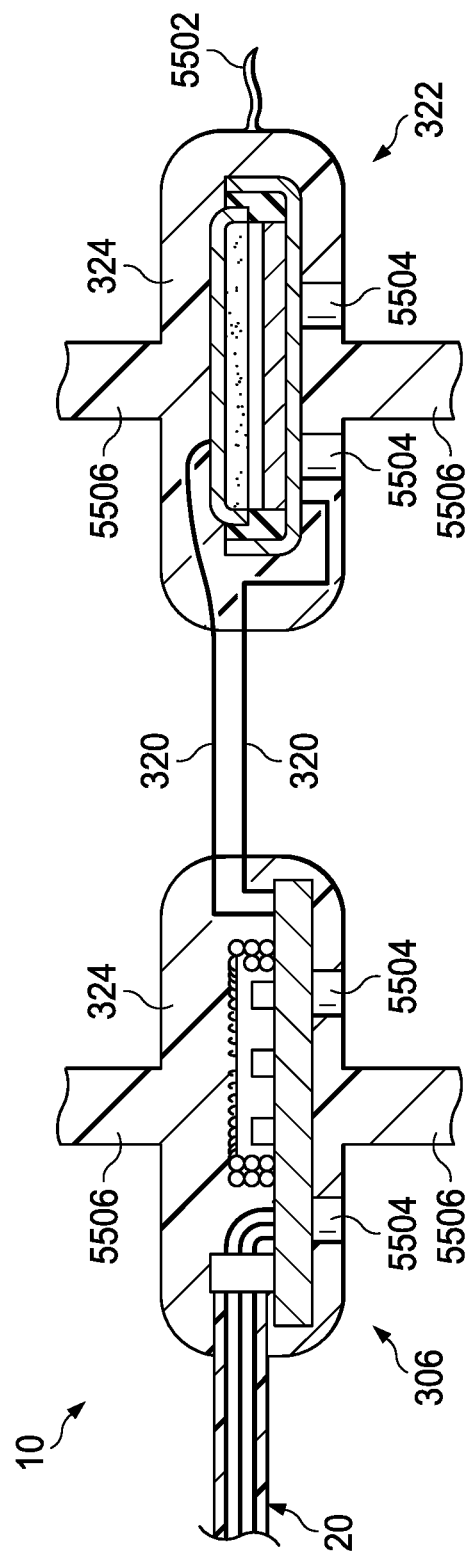
FIG. 55 illustrates a cross-sectional side view of an IPG with a nearly complete epoxy coating.

Turning now to FIG. 55, there is illustrated a cross-section side view of the next step. After the epoxy 5302 hardens and cures into epoxy coatings 324, the top mold half 5004 and the bottom mold half 5006 are removed from the IPG 10. Pieces of flash 5502 may exist at different points on the surface of the newly formed epoxy coating 324 where the top mold half 5004 and the bottom mold half 5006 fit together imperfectly. Sprues 5506 of epoxy may exist at the points where the epoxy ports 5014 and vacuum ports 5016 were. These bits of excess epoxy are simply cut or ground off. Also, small voids 5504 in the epoxy coatings 324 will have been created by the pedestals 5012, since epoxy would not have been able to fill those areas. The voids are simply filled with epoxy 5302 to complete the epoxy coatings 324.

Figure 56:
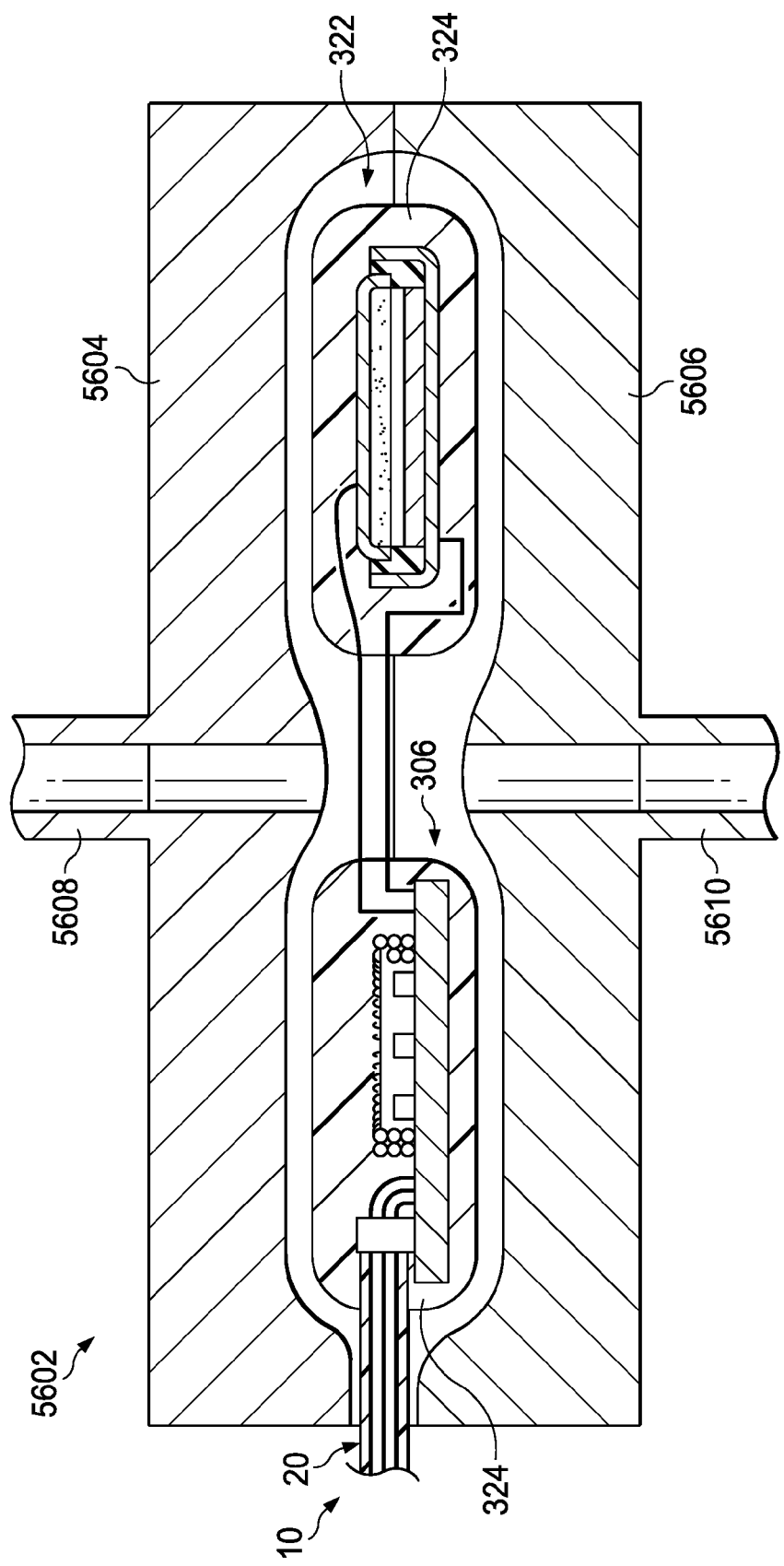
FIG. 56 illustrates a cross-sectional side view of an IPG placed inside a mold for applying a silicone coating.

Turning next to FIG. 56, there is illustrated a cross-sectional side view of the first step in applying a silicone coating 326 for embodiments which include such a coating. The process of applying a silicone coating 326 is very similar to the process of applying epoxy coatings 324, as described hereinabove with respect to FIGS. 50-55. A mold 5602 which includes a silicone mold top half 5604 and a silicone mold bottom half 5606 is placed around the IPG 10 (or the IPG 10 is placed within the silicone mold 5602). In the embodiment shown, the IPG 10 includes epoxy coatings 324, but the process would be identical for embodiments which include a silicone coating 326 but no epoxy coatings 324. The silicone mold 5602 is made of aluminum, steel, or any other material suitable for molding silicone. The silicone mold top half 5604 includes a silicone injection port 5608. The silicone mold bottom half 5606 includes a vacuum port 5610.

Figure 57:
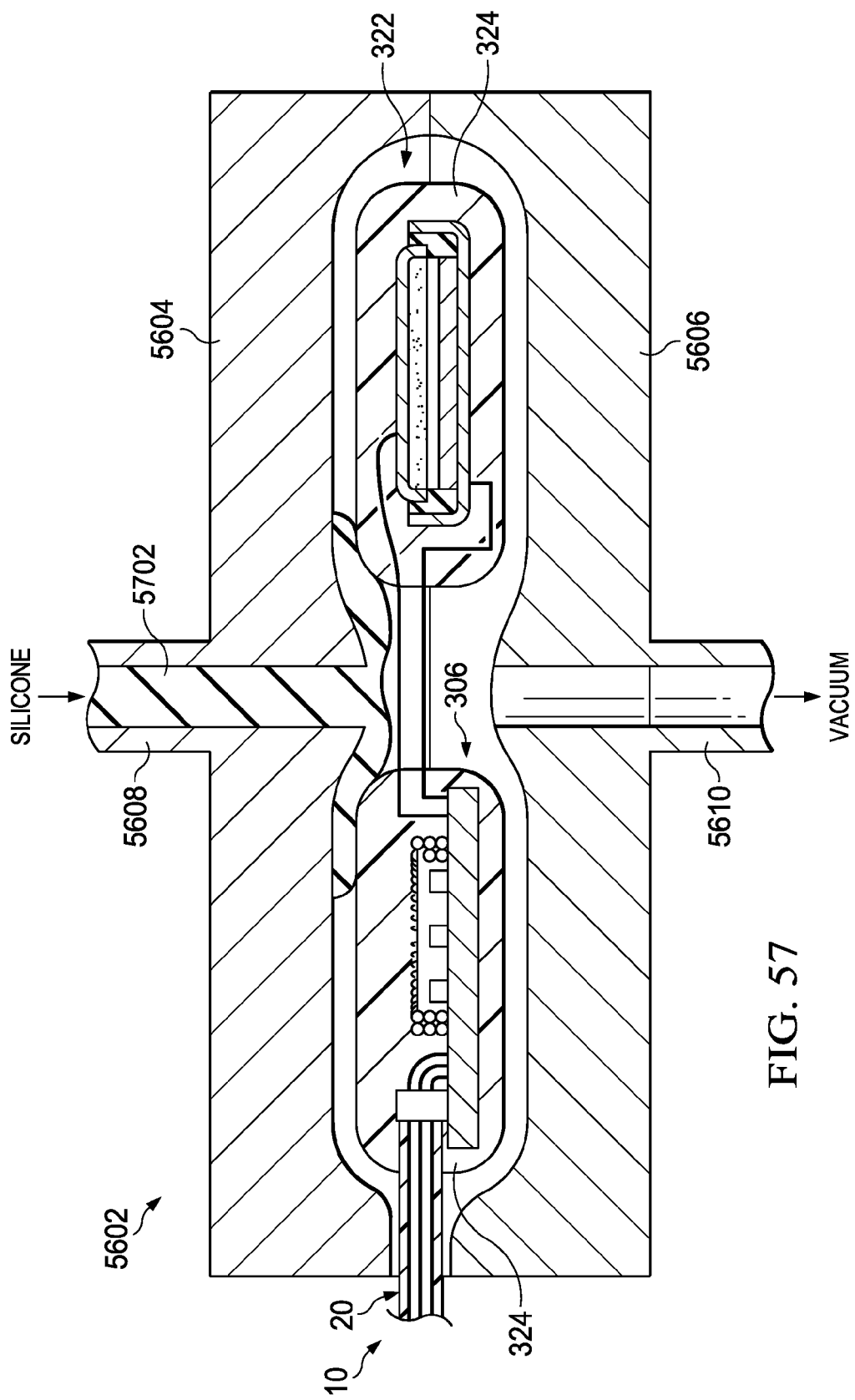
FIG. 57 illustrates a cross-sectional side view of a step of injecting silicone into a mold for applying a silicone coating to an IPG.

Turning now to FIG. 57, there is illustrated a cross-sectional side view of the next step in applying a silicone coating 326. In this step, the air within the silicone mold 5602 is sucked out of the vacuum port 5610 to create a vacuum within the silicone mold and around the IPG 10. At the same time, silicone 5702 is injected into the silicone injection port 5608 and begins to fill the silicone mold 5602 and flow around the ASIC body 306 and the battery body 322.

Figure 58:
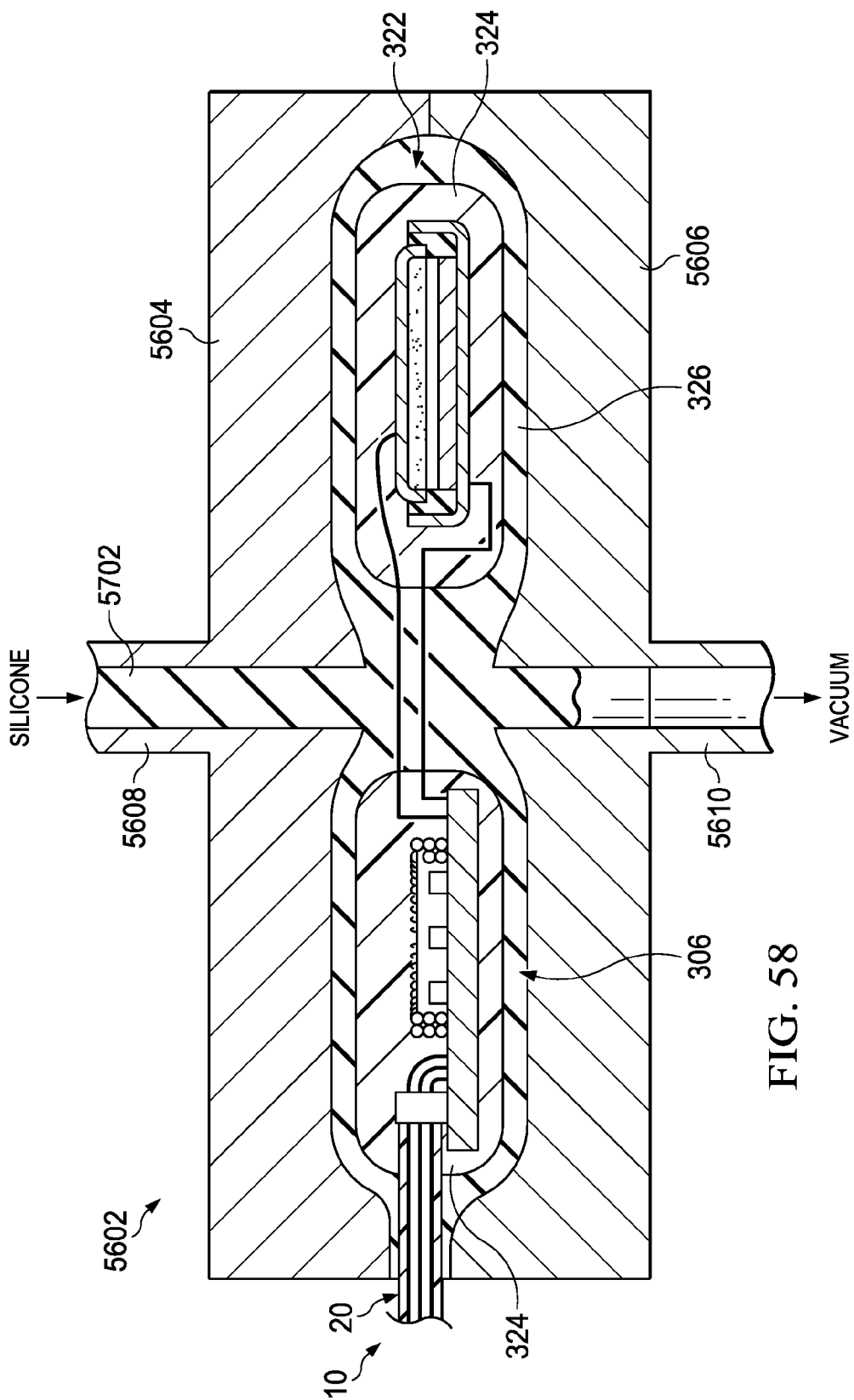
FIG. 58 illustrates a cross-sectional side view of another step in applying a silicone coating to an IPG.

Turning now to FIG. 58, there is illustrated a cross-sectional side view of the next step in applying a silicone coating 326. The silicone 5702 continues to be injected into the silicone mold 5602 until the silicone completely coats the ASIC body 306 and the battery body 322 to form the silicone coating 326. At this point, the injection of the silicone 5702 into the silicone mold 5602 ceases.

Figure 59:
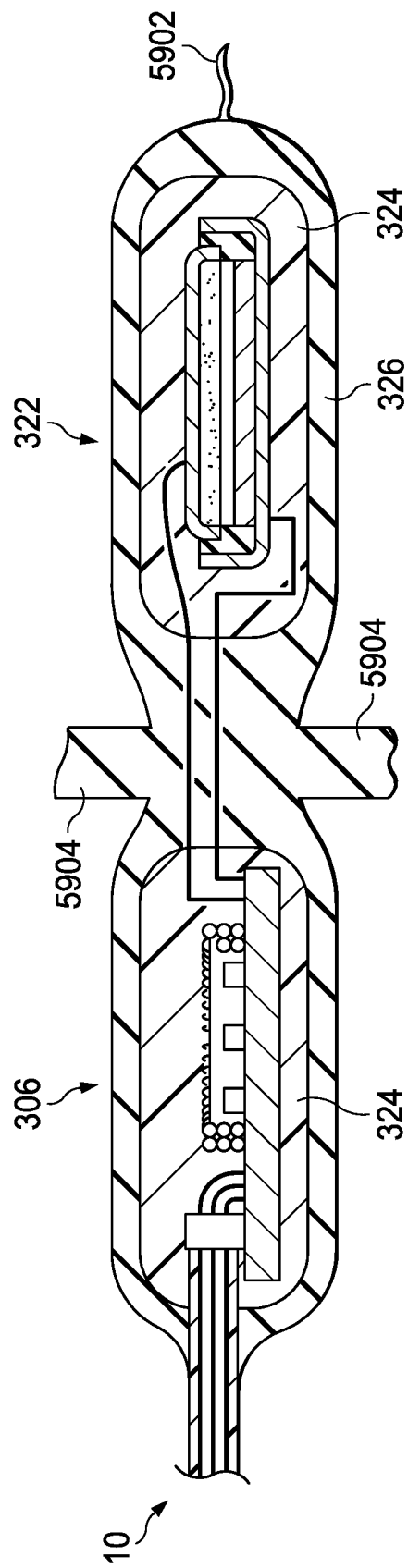
FIG. 59 illustrates a cross-sectional side view of a nearly complete silicone coating on an IPG.

Turning now to FIG. 59, there is illustrated a cross-sectional side view of the next step in applying the silicone coating 326. Once the injected silicone 5702 cools and hardens, the silicone mold 5602 is removed from the IPG 10. At this point, there may be bits of silicone flash 5902 at points where the silicone mold halves 5604, 5606 did not fit together enough to form a perfect seal. There may also be silicone sprues 5904 where the silicone injection port 5608 and the vacuum port 5610 were. These bits of excess silicone 5702 are simply trimmed off to complete the application of the silicone coating 326.

It should be noted that, while the embodiment of the IPG 10 depicted in FIGS. 56-59 include an epoxy coating 324, some embodiments include a silicone coating 326 but not an epoxy coating. The steps involved in applying a silicone coating 326 to an IPG 10 without an epoxy coating 324 are substantially similar to the steps described hereinabove with respect to FIGS. 56-59.

It will be appreciated by those skilled in the art having the benefit of this disclosure that this implantable head mounted neurostimulation system for head pain provides a unibody construction with implanted leads to cover the frontal, parietal, and occipital regions of the head. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A method for treating patients with migraine headaches, comprising the steps of:
subcutaneously implanting at least one neurostimulator control system through an incision in the cranial region, which neurostimulator control system includes a main body disposed proximate the incision having a processor disposed therein and an interface interfacing to a first, second, and third lead of at least three integrated stimulating leads, and each of the at least three integrated stimulating leads having:
a proximal end connected to the interface, and
an array of electrodes disposed along the length of the integrated stimulating lead proximate a distal end thereof and interfaced through internal wires to the processor through the interface;

extending the distal end of the first lead subcutaneously from the neurostimulator control system to the frontal cranial region so that at least one of the electrodes of the first integrated stimulating lead is proximate and over at least one nerve selected from at least one of the body, branches, and roots of at least one supraorbital nerve;

extending the distal end of the second integrated stimulating lead subcutaneously from the neurostimulator control system to the infraorbital cranial region so that at least one of the electrodes of the second lead is proximate and over at least one nerve selected from at least one of the body, branches, and roots of at least one infraorbital nerve;

extending the distal end of the third integrated stimulating lead subcutaneously from the neurostimulator control system to the occipital cranial region so that at least one of the electrodes of the third lead is proximate and over at least one nerve selected from at least one of the body, branches, and roots of at least one occipital nerve; and applying, after the extension of the first, second, and third integrated stimulating leads, at least one stimulating signal by the processor in the main body through the internal wires in the at least three integrated stimulating leads to the electrodes proximate the at least three nerves, thereby at least in part alleviating pain associated with migraine headaches.

2. The method of claim 1, wherein the incision is made proximate the parietal bone.

3. The method of claim 2, wherein the incision is distal and above the pinna.

4. The method of claim 1, wherein a subcutaneous pocket is created through the incision to contain the neurostimulator control system.

5. The method of claim 1, wherein the neurostimulator control system includes a power source and an internal communication system.

6. The method of claim 5, and further comprising interfacing an external communication system with the internal communication system to transmit signals thereto, wherein the transmission of signals to the internal communication system causes the processor to apply the at least one stimulating signal.

7. The method of claim 1, wherein the interface interfaces to a fourth integrated stimulating lead, and the fourth integrated stimulating lead having a proximal end connected to the interface and an array of electrodes disposed along the length of the fourth integrated stimulating lead proximate the distal end thereof and interfaced through internal wires to the processor through the interface, and further comprising the step of extending the distal end of the fourth integrated stimulating lead subcutaneously from the neurostimulator control system to the mandibular region so that at least one of the electrodes of the fourth integrated stimulating lead is proximate and over a nerve selected from at least one of the body, branches and roots of at least one of the mental nerves.

8. The method of claim 1, wherein the incision is closed prior to the step of applying the at least one stimulating signal.

9. The method of claim 1, wherein at least one of the at least three integrated stimulating leads includes a second array of electrodes with at least one of the electrodes in the second array disposed over at least one nerve which is selected from at least one of the body, branches and roots of at least one of the auriculo-temporal nerves.

10. A method for subcutaneously treating pain in a patient, comprising the steps of:
providing a neurostimulator with an implantable pulse generator (IPG) body and at least a primary integral lead, a secondary integral lead, and a tertiary integral lead, each lead with electrodes disposed thereon;
opening a primary incision to expose the subcutaneous region below the dermis in a selected portion of the body;
opening a pocket for the IPG through the primary incision;
inserting the primary integral lead through the primary incision and routing it subcutaneously to a first desired nerve region along a first desired path;
inserting the secondary integral lead through the primary incision and routing it subcutaneously to a second desired nerve region different than the first desired nerve region along a second desired path;
inserting the tertiary integral lead through the primary incision and routing it subcutaneously to a third desired nerve region different than the first and second desired nerve regions along a third desired path;
disposing the IPG in the pocket through the primary incision;
closing the primary incision; and
activating the IPG and the electrodes to provide localized stimulation to the desired nerve regions and at least one of the nerves associated with each of the desired nerve regions to achieve a desired pain reduction response from the patient.

11. The method of claim 10, wherein the neurostimulator further includes a quaternary integral lead, and further comprises:
inserting the quaternary integral lead through the primary incision and routing it subcutaneously to a fourth desired nerve region different than the first, second, and third desired nerve regions along a fourth desired path.

12. The method of claim 11, wherein the second desired nerve region is diametrically opposite the primary incision from the first desired nerve region.

13. The method of claim 10, wherein the selected portion of the body is the head.

14. The method of claim 13, wherein the incision is disposed proximate to and above the pinna.

15. The method of claim 10, wherein the selected portion of the body includes at least one nerve in the cranium and the primary integral lead is disposed so that at least one of the electrodes thereon is disposed above at least one nerve in the first desired nerve region.

16. The method of claim 15, wherein the at least one nerve is at least one of the body, branches and roots selected from the group consisting of the supraorbital nerves, the auriculotemporal nerves and the occipital nerves.

17. The method of claim 10, wherein
the step of opening the primary incision includes:
the step of opening a secondary incision along the first desired path and disposed away from the primary incision, and
the step of opening a tertiary incision along the third desired path and disposed away from the primary incision;
wherein the step of inserting the primary integral lead comprises:
inserting the primary integral lead through the primary incision and routing it subcutaneously to the secondary incision along the first desired path and extending through the secondary incision, and inserting the primary integral lead back through the secondary incision and routing it subcutaneously to the first desired nerve region along the first desired path;

wherein the step of inserting the tertiary lead comprises:

inserting the tertiary integral lead through the primary incision and routing it subcutaneously to the tertiary incision along the third desired path and extending through the tertiary incision, and inserting the tertiary integral lead back through the tertiary incision and routing it subcutaneously to the third desired nerve region along the third desired path; and wherein the step of closing the primary incision includes a step of closing the secondary and tertiary incisions.

18. The method of claim 17 wherein the desired pain reduction response is to reduce pain from headaches selected from the group consisting of migraine headaches, tension type headaches, cluster headaches, chronic daily headaches, hemicranias continua headaches, cervicogenic headaches, and secondary musculoskeletal headaches.

19. The method of claim 17, wherein the desired pain reduction response is to reduce pain from the type selected from the group consisting of neuropathic head pain, neuropathic face pain, nociceptive head pain, nociceptive face pain, sympathetic related head pain, and sympathetic related face pain.

20. The method of claim 17, wherein the desired pain reduction response is to reduce pain from neuralgia selected from the group consisting of greater occipital neuralgia, supraorbital neuralgia, auriculo-temporal neuralgia, infraorbital neuralgia, and trigeminal neuralgia.

* * * * *